US009244082B2

(12) United States Patent
Mei et al.

(10) Patent No.: US 9,244,082 B2
(45) Date of Patent: Jan. 26, 2016

(54) DETECTION AND TREATMENT OF LRP4-ASSOCIATED NEUROTRANSMISSION DISORDERS

(75) Inventors: Lin Mei, Evans, GA (US); Wen-Cheng Xiong, Evans, GA (US); Bin Zhang, Evans, GA (US); Chengyong Shen, Augusta, GA (US)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 13/452,018

(22) Filed: Apr. 20, 2012

(65) Prior Publication Data
US 2013/0108616 A1    May 2, 2013

Related U.S. Application Data

(63) Continuation-in-part of application No. PCT/US2010/053483, filed on Oct. 21, 2010.

(60) Provisional application No. 61/253,610, filed on Oct. 21, 2009.

(51) Int. Cl.

| *A61K 39/395* | (2006.01) |
|---|---|
| *A61K 38/00* | (2006.01) |
| *C07K 1/00* | (2006.01) |
| *G01N 33/68* | (2006.01) |
| *C12Q 1/68* | (2006.01) |
| *G01N 33/564* | (2006.01) |
| *G01N 33/92* | (2006.01) |

(52) U.S. Cl.
CPC .......... *G01N 33/6893* (2013.01); *C12Q 1/6883* (2013.01); *G01N 33/564* (2013.01); *G01N 33/92* (2013.01); *C12Q 2600/106* (2013.01); *C12Q 2600/136* (2013.01); *C12Q 2600/156* (2013.01); *C12Q 2600/158* (2013.01); *C12Q 2600/178* (2013.01); *G01N 2800/28* (2013.01); *G01N 2800/38* (2013.01)

(58) Field of Classification Search
None
See application file for complete search history.

(56) References Cited

U.S. PATENT DOCUMENTS 7,267,820 B2    9/2007    Vincent et al.

FOREIGN PATENT DOCUMENTS

| GB | 2381 790 A | * | 5/2003 | ........... C07K 14/705 |
| GB | 2381 790 A | * | 5/2003 | ........... C07K 14/705 |
| WO | WO 97/21811 A2 | | 6/1997 | |
| WO | WO 97/21811 A3 | | 8/1997 | |
| WO | WO 2011/050134 A2 | | 4/2011 | |
| WO | WO 2011/050134 A3 | | 9/2011 | |

OTHER PUBLICATIONS

Böse et al., "Agrin controls synaptic differentiation in hippocampal neurons," Dec. 15, 2000, *J Neurosci*; 20:9086-9095.
Cadigan and Liu, "Wnt signaling• complexity at the surface," Feb. 1, 2006, *J Cell Sci*; 119:395-402.
Campanelli et al., "Alternative RNA splicing that determines agrin activity regulates binding to heparin and alpha-dystroglycan," May 1996, *Development*; 122:1663-1672.
Cheusova et al., "Casein kinase 2-dependent serine phosphorylation of MuSK regulates acetylcholine receptor aggregation at the neuromuscular junction," Jul. 1, 2006, *Genes Dev*; 20: 1800-1816.
Clevers, "Wnt/beta-catenin signaling in development and disease," Nov. 3, 2006, *Cell*; 127:469-480.
Cole et al., "Patient autoantibodies deplete postsynaptic muscle-specific kinase leading to disassembly of the ACh receptor scaffold and myasthenia gravis in mice," Sep. 1, 2010 *J Physiol.*; 588(Pt 17):3217-3229. Available online on Jul. 5, 2010.
Di Castro et al., "Pathogenic point mutations in a transmembrane domain of the [epsilon] subunit increase the $Ca^{2+}$ permeability of the human endplate ACh receptor," Mar. 15, 2007, *J Physiol*; 579(Pt 3):671-7. Available online on Feb. 1, 2007.
Ding et al., "Caprin-2 enhances canonical Wnt signaling through regulating LRP5/6 phosphorylation," Sep. 18, 2008, *J Cell Biol*; 182:865-872. Available online on Sep. 1, 2008.
Ferns et al, "Agrin-induced acetylcholine receptor clustering in mammalian muscle requires tyrosine phosphorylation," Mar. 1, 1996, *J Cell Biol*; 132:937-944.
Ferreira, "Abnormal synapse formation in agrin-depleted hippocampal neurons," Dec. 1999, *J Cell Sci*; 112(Pt 24):4729-4738.
Flanagan et al., "Alkaline phosphatase fusion proteins for molecular characterization and cloning of receptors and their ligands," 2000, *Methods Enzymol*; 327:198-210.
Fuhrer et al., "Association of muscle-specific kinase MuSK with the acetylcholine receptor in mammalian muscle," Aug. 15, 1997, *EMBO J*;.16:4951-4960.
Gesemann et al., "Acetylcholine receptor-aggregating activity of agrin isoforms and mapping of the active site," Feb. 1995, *J Cell Biol*; 128:625-636.
Gesemann et al., "Alternative splicing of agrin alters its binding to heparin, dystroglycan, and the putative agrin receptor," Apr. 1996, *Neuron* (USA); 16:755-767.
Glass et al., "Agrin acts via a MuSK receptor complex," May 17, 1996, *Cell*; 85:513-523.

(Continued)

Primary Examiner — Olga N Chernyshev
(74) Attorney, Agent, or Firm — Mueting, Raasch & Gebhardt, P.A.

(57) ABSTRACT

The present invention includes methods for the detection of neurotransmission or developmental disorders, including, but not limited to, myasthenia gravis that is seronegative for autoantibodies to the acetylcholine receptor (AChR) and/or muscle specific tyrosine kinase (MuSK), the method including detecting autoantibodies that bind to LRP4, or an epitope thereof. Also included are methods for the treatment of an individual suffering from a neurotransmission disorder, the method including detecting in a bodily fluid of the individual autoantibodies that bind to LRP4, or an epitope thereof, and administering to the patient an effective amount an immunosuppressant and/or another appropriate therapeutic modality. Also included are antibodies that bind to autoantibodies to LRP4 and kits for the detection of neurotransmission or developmental disorders.

20 Claims, 16 Drawing Sheets

(56) References Cited

OTHER PUBLICATIONS

Glass et al., "Kinase domain of the muscle-specific receptor tyrosine kinase (MuSK) is sufficient for phosphorylation but not clustering of acetylcholine receptors: required role for the MuSK ectodomain?"Aug. 5, 1997, *Prot Natl Acad Sci* USA; 94:8848-8853.
Hall et al., "Axonal remodeling and synaptic differentiation in the cerebellum is regulated by WNT-7a signaling," Mar. 3, 2000, *Cell*; 100:525-535.
He et al., "LDL receptor-related proteins 5 and 6 in Wnt/beta-catenin signaling: arrows point the way," Apr. 2004, *Development*; 131:1663-1677.
Herbst and Burden, "The juxtamembrane region of MuSK has a critical role in agrin-mediated signaling," Jan. 4, 2000, *EMBO J*; 19:67-77.
Higuchi et al., "Autoantibodies to low-density lipoprotein receptor-related protein 4 in myasthenia gravis," Feb. 2011 *Ann Neurol*.;69(2):418-422.
Hilgenberg et al., "$\alpha 3 Na^+/K^+$-ATPase is a neuronal receptor for agrin," Apr. 21, 2006, *Cell*; 125:359-369.
Hopf and Hoch, "Agrin binding to $\alpha$-dystroglycan. Domains of agrin necessary to induce acetylcholine receptor clustering are overlapping but not identical to the alpha-dystroglycan-binding region," Mar. 1, 1996, *J Biol Chem*; 271:5231-5236.
Hopf and Hoch, "Dimerization of the muscle-specific kinase induces tyrosine phosphorylation of acetylcholine receptors and their aggregation on the surface of myotubes," Mar. 13, 1998 *J Biol Chem*.; 273(11):6467-6473.
Johnson et al., "Abnormal development of the apical ectodermal ridge and polysyndactyly in Megf7-deficient mice," Nov. 15, 2005 *Hum Mol Genet*.; 14(22):3523-3538. Available online on Oct. 5, 2005.
Kao and Drachman, "Myasthenic immunoglobulin accelerates acetylcholine receptor degradation," Apr. 29, 1977 *Science*; 196(4289):527-529.
Kim et al. "Lrp4 is a receptor for Agrin and forms a complex with MuSK" Oct. 17, 2008 *Cell*; 135(2):334-342.
Klassen and Shen, "Wnt signaling positions neuromuscular connectivity by inhibiting synapse formation in *C. elegans*," Aug. 24, 2007, *Cell*; 130:704-716.
Lavrnic et al., "The features of myasthenia gravis with autoantibodies to MuSK," Aug. 2005 *J Neurol Neurosurg Psychiatry*.; 76(8):1099-1102.
Leite et al., "IgG1 antibodies to acetylcholine receptors in 'seronegative' myasthenia gravis," Jul. 2008 *Brain*; 131(Pt 7):1940-1952. Available online on May 31, 2008.
Lennon et al., "Role of complement in the pathogenesis of experimental autoimmune myasthenia gravis," Apr. 1, 1978 *J Exp Med*.;147(4):973-983.
Li et al., "Retrograde regulation of motoneuron differentiation by muscle $\beta$-catenin," Mar. 2008, *Nat Neurosci*; 11:262-268. Available online on Feb. 17, 2008.
Littleton et al., "Immunocapture and identification of cell membrane protein antigenic targets of serum autoantibodies," Jul. 2009 *Mol Cell Proteomics*; 8(7):1688-96. Available online on Mar. 29, 2009.
Lu et al., "A role for LRP4 in neuronal cell viability is related to apoE-binding," Oct. 26, 2007, *Brain Res*; 1177:19-28. Available online on Aug. 25, 2007.
Luo et al., "Regulation of AChR clustering by Dishevelled interacting with MuSK and PAK1," Aug. 1, 2002, *Neuron*; 35:489-505.
Luo et al., "Implication of geranylgeranyltransferase I in synapse formation," Nov. 13, 2003, *Neuron*; 40:703-717.
Luo et al., "HSP90 beta regulates rapsyn turnover and subsequent AChR cluster formation and maintenance," Oct. 9, 2008 *Neuron*; 60(1):97-110.
Mathew et al., "Wingless signaling at synapses is through cleavage and nuclear import of receptor DFrizzled2," Nov. 25, 2005, *Science*; 310:1344-1347.

Mittaud et al., "Agrin-induced activation of acetylcholine receptor-bound Src family kinases requires Rapsyn and correlates with acetylcholine receptor clustering," Apr. 27, 2001, *J Biol Chem*; 276:14505-14513. Available online on Jan. 31, 2001.
Mohamed et al., "Src-class kinases act within the agrin/MuSK pathway to regulate acetylcholine receptor phosphorylation, cytoskeletal anchoring, and clustering," Jun. 1, 2001, *J Neurosci*; 21:3806-3818.
Nemoto et al., "Patterns and severity of neuromuscular transmission failure in seronegative myasthenia gravis," May 2005, *J Neural Neurosurg Psychiatry*; 76(5):714-8.
Obermoeller-McCormick et al., "Dissection of receptor folding and ligand-binding property with functional minireceptors of LDL receptor-related protein," Mar. 2001, *J Cell Sci*; 114:899-908.
O'Connor et al., "Localization and alternative splicing of agrin mRNA in adult rat brain: transcripts encoding isoforms that aggregate acetylcholine receptors are not restricted to cholinergic regions," Mar. 1994, *J Neurosci*; 14:1141-1152.
Okada et al., "The muscle protein Dok-7 is essential for neuromuscular synaptogenesis," Jun. 23, 2006, *Science*; 312:1802-1805.
Packard et al., "The *Drosophila* Wnt, wingless, provides an essential signal for pre- and postsynaptic differentiation," Nov. 1, 2002, *Cell*; 111:319-330.
Patrick and Lindstrom, "Autoimmune response to acetylcholine receptor," May 25, 1973 *Science*; 180(88):871-872.
Pevzner et al., "Anti-LRP4 autoantibodies in AChR- and MuSK-antibody-negative myasthenia gravis," Mar. 2012 *J Neurol* 258(3):427-35. Available online on Aug. 5, 2011.
Pittock et al., "Neuromyelitis optica and non-organ-specific autoimmunity," Jan. 2008 *Arch Neurol*.; 65(1):78-83.
Qu and Huganir, "Comparison of innervation and agrin-induced tyrosine phosphorylation of the nicotinic acetylcholine receptor," Nov. 1994, *J Neurosci*; 14:6834-6841.
Schulte and Bryja, "The Frizzled family of unconventional G-protein-coupled receptors," Oct. 2007, *Trends Pharmacal Sci*; 28:518-525. Available online on Sep. 17, 2007.
Semenov et al., "Head inducer Dickkopf-1 is a ligand for Wnt coreceptor LRP6," Jun. 26, 2001, *Curr Biol*; 11:951-961.
Shen et al., "Congenital myasthenia-related AChR delta subunit mutation interferes with intersubunit communication essential for channel gating," May 2008, *J Clin Invest*; 118(5):1867-76.
Shigemoto et al., "Induction of myasthenia by immunization against muscle-specific kinase," Apr. 2006 *J Clin Invest*.; 116(4):1016-1024. Available online on Mar. 23, 2006.
Si et al., "Induction of acetylcholine receptor gene expression by ARIA requires activation of mitogen-activated protein kinase," Aug. 16, 1996, *J Biol Chem*; 271:19752-19759.
Simon-Chazottes et al., "Mutations in the gene encoding the low-density lipoprotein receptor LRP4 cause abnormal limb development in the mouse," 2006 *Genomics* 87:673-677. Available online on Mar. 6, 2006.
Song and Balice-Gordon, "New dogs in the dogma: Lrp4 and Tid1 in neuromuscular synapse formation," Nov. 26, 2008 *Neuron* 60:526-8.
Spaargaren et al., "Antibody-induced dimerization activates the epidermal growth factor receptor tyrosine kinase," Jan. 25, 1991 *J Biol Chem*.; 266(3):1733-1739.
ter Beek et al., "The effect of plasma from muscle-specific tyrosine kinase myasthenia patients on regenerating endplates," Oct. 2009 *Am J Pathol*.; 175(4):1536-1544. Available online on Sep. 10, 2009.
Valenzuela et al., "Receptor tyrosine kinase specific for the skeletal muscle lineage: expression in embryonic muscle, at the neuromuscular junction, and after injury," Sep. 1995, *Neuron*; 15:573-584.
Wang et al., "The Ig1/2 domain of MuSK binds to muscle surface and is involved in acetylcholine receptor clustering," 2008, *Neurosignals*; 16:246-253. Available online on Feb. 5, 2008.
Weatherbee et al., "LDL-receptor-related protein 4 is crucial for formation of the neuromuscular junction," Dec. 2006 *Development*; 133(24):4993-5000.
Weston et al., "Agrin-induced acetylcholine receptor clustering is mediated by the small guanosine triphosphatases Rac and Cdc42," Jul. 10, 2000, *J Cell Biol*; 150:205-212.

(56) References Cited

OTHER PUBLICATIONS

Weston et al., "Cooperative regulation by Rac and Rho of agrin-induced acetylcholine receptor clustering in muscle cells," Feb. 21, 2003, *J Biol Chem*; 278:6450-6455. Available online on Dec. 6, 2002.
Wiedemann, "Synapse formation: the missing link," Dec. 2008 *Nature Rev. Neurosci*. 11(9):608.
Wu et al., "To build a synapse: signaling pathways in neuromuscular junction assembly," Apr. 2010 *Development*; 137(7):1017-1033.
Zhang et al., "β-catenin regulates acetylcholine receptor clustering in muscle cells through interaction with rapsyn," Apr. 11, 2007 *J Neurosci*.; 27(15):3968-3973.
Zhang et al., "LRP4 serves as a coreceptor of agrin," Oct. 23, 2008 *Neuron*; 60(2):285-297. Available online on Oct. 22, 2008.
Zhou et al., "Distinct domains of MuSK mediate its abilities to induce and to associate with postsynaptic specializations," Sep. 6, 1999, *J Cell Biol*; 146:1133-1146.
Zhu et al., "Muscle-specific receptor tyrosine kinase endocytosis in acetylcholine receptor clustering in response to agrin," Feb. 13, 2008, *J Neurosci*; 28:1688-1696.
Aharonov et al., "Humoral antibodies to acetylcholine receptor in patients with myasthenia gravis." Aug. 23, 1975 *Lancet* 2(7930):340-342.
Beeson et al., "Congenital myasthenic syndromes and the formation of the neuromuscular junction," Jun. 2008, *Ann N Y Acad Sci*; 1132:99-103. Available online on Jun. 28, 2008.
Cole et al., "Anti-MuSK patient antibodies disrupt the mouse neuromuscular junction," Jun. 2008 *Ann Neurol*.; 63(6):782-789. Available online on Apr. 2, 2008.
Deymeer et al., "Clinical comparison of anti-MuSK- vs anti-AChR-positive and seronegative myasthenia gravis," Feb. 20, 2007, *Neurology*; 68(8):609-11.
Engel, "Congenital myasthenic syndromes," 2008, *Handb Clin Neurol*; 91:285-331.
Engel et al., "What have we learned from the congenital myasthenic syndromes," Jan. 2010, *J Mol Neurosci*; 40(1-2):143-53. Available online on Aug. 18, 2009.
Farrugia et al., "Single-fiber electromyography in limb and facial muscles in muscle-specific kinase antibody and acetylcholine receptor antibody myasthenia gravis," Apr. 2006, *Muscle Nerve*; 33(4):568-70.
Farrugia et al., "Effect of sera from AChR-antibody negative myasthenia gravis patients on AChR and MuSK in cell cultures," Apr. 2007, *J Neuroimmunol*; 185(1-2):136-44. Available online on Mar. 1, 2007.
Farrugia et al., "Quantitative EMG of facial muscles in myasthenia patients with MuSK antibodies," Feb. 2007, *Clin Neurophysiol*; 118(2):269-77. Available online on Dec. 8, 2006.
Guptill et al., "Anti-musk antibody myasthenia gravis: Clinical findings and response to treatment in two large cohorts," Jul. 2011 *Muscle Nerve*.;44(1):36-40.
Hamnik et al., "Neuromyelitis optica (NMO) antibody positivity in patients with transverse myelitis and no visual manifestations," May-Jun. 2008 *Semin Ophthalmol*.; 23(3):191-200.
Hoch et al., "Auto-antibodies to the receptor tyrosine kinase MuSK in patients with myasthenia gravis without acetylcholine receptor antibodies," Mar. 2001 *Nat Med*.; 7(3):365-368.
Ip et al., "Cloning and characterization of muscle-specific kinase in chicken," Nov. 2000, *Mol Cell Neurosci*; 16:661-673.
Jha et al., "Myasthenia gravis induced in mice by immunization with the recombinant extracellular domain of rat muscle-specific kinase (MuSK)," Jun. 2006 *J Neuroimmunol*.; 175(1-2):107-117. Available online on May 11, 2006.
Lang and Vincent, "Autoimmune disorders of the neuromuscular junction," Jun. 2009, *Curr Opin Pharmacol*; 9(3):336-401. Available online on May 8, 2009.
Leite et al., "Fewer thymic changes in MuSK antibody-positive than in MuSK antibody-negative MG," Mar. 2005 *Ann Neurol*.; 57(3):444-448.

Lindstrom et al., "Antibody to acetylcholine receptor in myasthenia gravis. Prevalence, clinical correlates, and diagnostic value," Nov. 1976 *Neurology*; 26(11):1054-1059.
Lindstrom et al., "Production and assay of antibodies to acetylcholine receptors," 1981 *Methods Enzymol*.; 74(Pt C):432-460.
Liyanage et al., "The agrin/muscle-specific kinase pathway: new targets for autoimmune and genetic disorders at the neuromuscular junction," Jan. 2002, *Muscle Nerve*; 25(1):4-16.
Matthews et al., "Muscle-specific receptor tyrosine kinase autoantibodies—a new immunoprecipitation assay," Oct. 2004 *Clin Chim Acta*.; 348(1-2):95-99.
McConville and Vincent, "Diseases of the neuromuscular junction," Jun. 2002, *Curr Opin Pharmacal*; 2(3):296-301.
McConville et al., "Detection and characterization of MuSK antibodies in seronegative myasthenia gravis," Apr. 2004 *Ann Neurol*.; 55(4):580-584.
McKeon et al., "Coexistence of myasthenia gravis and serological markers of neurological autoimmunity in neuromyelitis optica," Jan. 2009 *Muscle Nerve*; 39(1):87-90.
Meriggioli and Sanders, "Autoimmune myasthenia gravis: emerging clinical and biological heterogeneity," May 2009 *Lancet Neurol*.;8(5):47 5-490.
Punga et al., "Muscle-selective synaptic disassembly and reorganization in MuSK antibody positive MG mice," Aug. 2011 *Exp Neurol*.; 230(2):207-217. Available online on Apr. 30, 2011.
Sanders et al., "Clinical aspects of MuSK antibody positive seronegative MG," Jun. 24, 2003 *Neurology*; 60(12):1978-1980.
Selcen et al., "Dok-7 myasthenia: phenotypic and molecular genetic studies in 16 patients," Jul. 2008, *Ann Neurol*; 64(1):71-87.
Shigemoto et al., "Myasthenia gravis experimentally induced with muscle-specific kinase," 2008 *Ann NY Acad Sci*.; 1132:93-98. Available online on Dec. 20, 2007.
Shiraishi et al., "Acetylcholine receptors loss and postsynaptic damage in MuSK antibody-positive myasthenia gravis," Feb. 2005, *Ann Neural*; 57(2):289-93.
Strochlic et al., "The synaptic muscle-specific kinase (MuSK) complex: new partners, new functions," Nov. 2005, *Bioessays*; 27:1129-1135.
Suhail et al., "Serological and clinical features of patients with myasthenia gravis in north Indian population," Feb. 2010 *Int J Neurosci*.; 120(2):115-119.
Tian et al., "Interaction of LDL receptor-related protein 4 (LRP4) with postsynaptic scaffold proteins via its C-terminal PDZ domain-binding motif, and its regulation by Ca/calmodulin-dependent protein kinase II," Jun. 2006 *Eur J Neurosci*.; 23(11):2864-2876.
Toyka et al., "Myasthenia gravis. Study of humoral immune mechanisms by passive transfer to mice," Jan. 20, 1977 *N Engl J Med*.; 296(3):125-131.
Tronconi et al., "Antibody-induced degradation of acetylcholine receptor in myasthenia gravis: clinical correlates and pathogenetic significance," Nov. 1981 *Neurology*; 31(11):1440-1444.
Tsiamalos et al., "Epidemiological and immunological profile of muscle-specific kinase myasthenia gravis in Greece," Aug. 2009 *Eur J Neurol*.; 16(8):925-930. Available online on Apr. 3, 2009.
Tzartos et al., "Role of the main immunogenic region of acetylcholine receptor in myasthenia gravis. An Fab monoclonal antibody protects against antigenic modulation by human sera," Apr. 1985 *J Immunol*.; 134(4):2343-2349.
Vincent et al., "Seronegative generalised myasthenia gravis: clinical features, antibodies, and their targets," Feb. 2003, *Lancet Neurol*; 2(2):99-106.
Vincent et al., "Antibodies in myasthenia gravis and related disorders," Sep. 2003, *Ann N Y Acad Sci*; 998:324-35.
Vincent et al., "Seronegative myasthenia gravis," Mar. 2004, *Semin Neural*; 24(1): 125-33.
Vincent and Rothwell, "Myasthenia gravis," Jun. 2004, *Autoimmunity*; 37(4):317-9.
Vincent et al., "Is 'seronegative' MG explained by autoantibodies to MuSK?" Jan. 25, 2005, *Neurology*; 64(2):399; author reply 399.
Vincent and Leite, "Neuromuscular junction autoimmune disease: muscle specific kinase antibodies and treatments for myasthenia gravis," Oct. 2005, *Curr Opin Neurol*; 18(5):519-25.

(56) References Cited

OTHER PUBLICATIONS

Vincent, "Immunology of disorders of neuromuscular transmission," 2006, *Acta Neurol Scand Suppl*; 183:1-7.
Vincent et al., "Myasthenia gravis seronegative for acetylcholine receptor antibodies," 2008, *Ann NY Acad Sci*; 1132:84-92.
Wandinger et al., "New serological markers for the differential diagnosis of autoimmune limbic encephalitis," Nov. 2011, *J Lab Med*; 35(6):329-342. English language abstract only; available online at: <degruyter.com/view/j/labm.2011.35.issue-6/jlm.2011.059et/jlm.2011.059et.xml?format=INT&print>; 1 page.
Zhou et al., "Clinical comparison of muscle-specific tyrosine kinase (MuSK) antibody-positive and -negative myasthenic patients," Jul. 2004 *Muscle Nerve*; 30(1):55-60.
Jarius et al., "Standardized method for the detection of antibodies to aquaporin-4 based on a highly sensitive immunofluorescence assay employing recombinant target antigen," 2010 *J. Neurolog. Sci.* 291(2010):52-56. Available online on Feb. 1, 2010.
Losen et al., "Treatment of Myasthenia Gravis by Preventing Acetylcholine Receptor Modulation," 2008 *Ann. NY Acad. Sci.* 1132:174-179.
Richman, "Antibodies to Low Density Lipoprotein Receptor-Related Protein 4 in Seronegative Myasthenia Gravis," 2011 *Archive Neurol.* doi:10.1001/archneurol.2011.2855; E1-E2. Available online on Dec. 12, 2011.
Wandinger et al., "Anti-NMDA-receptor encephalitis: A severe, multistage, treatable disorder presenting with psychosis," Feb. 2011 *J. Neuroimmunol.* 231(1-2):86-91. Available online on Oct. 15, 2010.
Vincent and Drachman, "Myasthenia Gravis," Chapter 11 in *Neuromuscular Disorders*, Rahman (Ed.); Lippincott Williams & Wilkins: Philadelphia, PA; 2001. pp. 159-188.
Zhang et al., "Autoantibodies to Lipoprotein-Related Protein 4 in Patients With Double-Seronegative Myasthenia Gravis," 2011 *Archive Neurol.* doi:10.1001/archneurol.2011.2393; E1-E7. Available online on Dec. 12, 2011.
Supplemental European Search Report and European Search Opinion issued on Jun. 28, 2013, in connection with European Patent Application No. 10825651.2, having an international filed of Oct. 21, 2010.
Bryant, *Laboratory Immunology & Serology Third Edition*, W.B. Saunders Company: Philadelphia, PA; Copyright 1992. Cover page, publisher's page, and p. 366.
"Lrp4," Mouse Genome Informatics, The Jackson Laboratory, [online]. Last modified on Apr. 16, 2013. Bethesda, MD [retrieved on May 13, 2013]. Retrieved from the Internet at informatics.jax.org/marker/MGI:2442252; 2 pgs.
"LRP4," National Center for Biotechnology Information, National Library of Medicine, National Institutes of Health, GenBank Locus NM_002334, Accession No. NM_002334 XM_035037, Version NM_002334.3 GI:296923822, "*Homo sapiens* low density lipoprotein receptor-related protein 4 (LRP4), mRNA," [online]. Last modified on Apr. 17, 2013. Bethesda, MD [retrieved on May 13, 2013]. Retrieved from the Internet: at ncbi.nlm.nih.gov/nuccore/NM_002334.3; 10 pgs.
"Lrp4," Rat Genome Database, Rat Genome Database [online]. Last updated on May 1, 2013. Medical College of Wisconsin, Milwaukee, Wisconsin, [retrieved on May 13, 2013]. Retrieved from the Internet at rgd.mcw.edu/rgdweb/report/gene/main.html?id=%20619731; 2 pgs.
"LRP4," Universal Protein Resource (UniProt), UniProt Knowledgebase (UniProtKB), Accession No. O75096, Version 113, "LRP4_Human," [online]. Last modified May 1, 2013. Geneva, Switzerland [retrieved on May 13, 2013]. Retrieved from the Internet at uniprot.org/uniprot/O75096; 15 pgs.
Playfair and Lydyard, *Medical Immunology Made Memorable Second Edition*, Harcourt Publishers Limited: London, England; Copyright 2000. Cover page, publisher's page, and p. 98.
Zane, "Types of Antigens," in *Immunology: Theoretical & Practical Concepts in Laboratory Medicine*, Allen et al. (Eds.). W.B. Saunders Company: Philadelphia, PA; Copyright 2001. Cover page, publisher's page, and pp. 40-41.
Zisimopoulou et al. "A comprehensive analysis of the epidemiology and clinical characteristics of anti-LRP4 in myasthenia gravis". 2014. *Journal of Autoimmunity*. 52:139-145.

\* cited by examiner

Figure 7
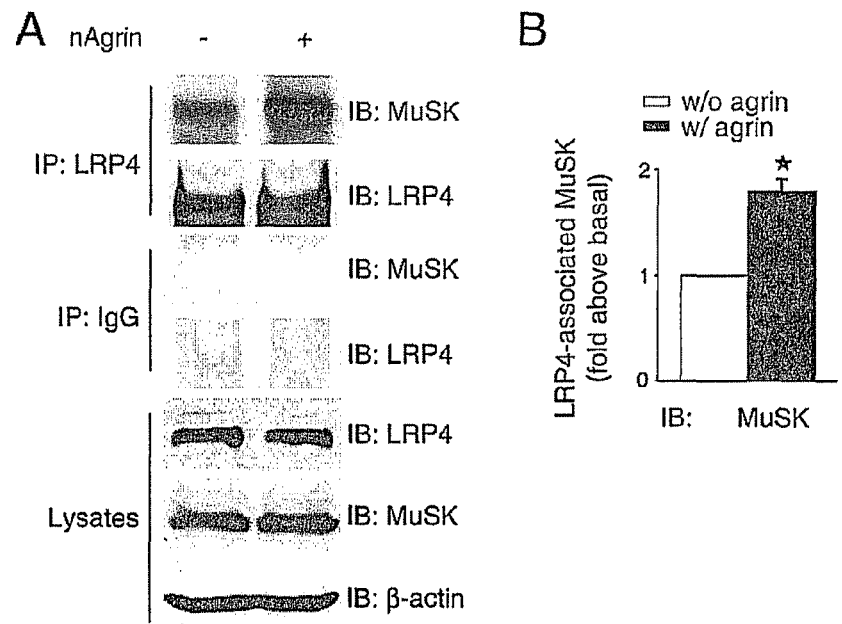
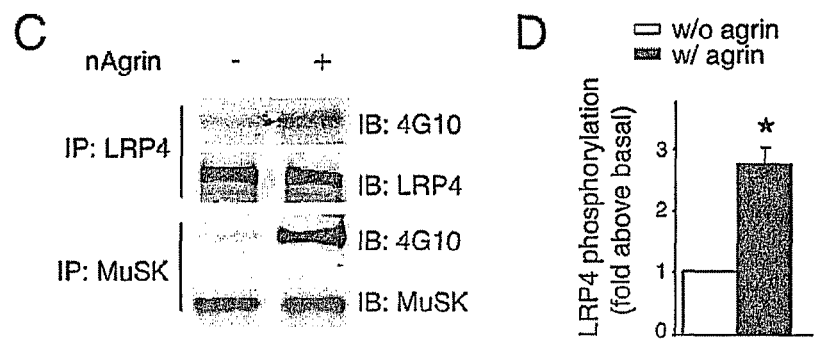
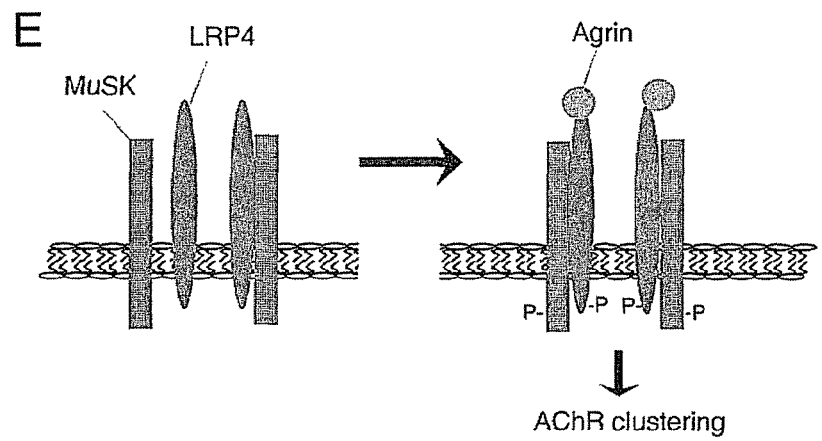

Figure 9-1

```
         10         20         30         40         50         60
MRRQWGALLL GALLCAHGLA SSPECACGRS HFTCAVSALG ECTCIPAQWQ CDGDNDCGDH 70         80         90        100        110        120
SDEDGCILPT CSPLDFHCDN GKCIRRSWVC DGDNDCEDDS DEQDCPPREC EEDEFPCQNG 130        140        150        160        170        180
YCIRSLWHCD GDNDCGDNSD EQCDMRKCSD KEFRCSDGSC IAEHWYCDGD TDCKDGSDEE 190        200        210        220        230        240
NCPSAVPAPP CNLEEFQCAY GRCILDIYHC DGDDDCGDWS DESDCSSHQP CRSGEFMCDS 250        260        270        280        290        300
GLCINAGWRC DGDADCDDQS DERNCTTSMC TAEQFRCHSG RCVRLSWRCD GEDDCADNSD 310        320        330        340        350        360
EENCENTGSP QCALDQFLCW NGRCIGQRKL CNGVNDCGDN SDESPQQNCR PRTGEENCNV 370        380        390        400        410        420
NNGGCAQKCQ MVRGAVQCTC HTGYRLTEDG HTCQDVNECA EEGYCSQGCT NSEGAFQCWC 430        440        450        460        470        480
ETGYELRPDR RSCKALGPEP VLLFANRIDI RQVLPHRSEY TLLLNNLENA IALDFHHRRE 490        500        510        520        530        540
LVFWSDVTLD RILRANLNGS NVEEVVSTGL ESPGGLAVDW VHDKLYWTDS GTSRIEVANL 550        560        570        580        590        600
DGAHRKVLLW QNLEKPRAIA LHPMEGTIYW TDWGNTPRIE ASSMDGSGRR IIADTHLFWP 610        620        630        640        650        660
NGLTIDYAGR RMYWVDAKHH VIERANLDGS HRKAVISQGL PHPFAITVFE DSLYWTDWHT
```

Figure 9-2

```
            670        680        690        700        710        720
       KSINSANKFT GKNQEIIRNK LHFPMDIHTL HPQRQPAGKN RCGDNNGGCT HLCLPSGQNY 730        740        750        760        770        780
       TCACPTGFRK ISSHACAQSL DKFLLFARRM DIRRISFDTE DLSDDVIPLA DVRSAVALDW 790        800        810        820        830        840
       DSRDDHVYWT DVSTDTISRA KWDGTGQEVV VDTSLESPAG LAIDWVTNKL YWTDAGTDRI 850        860        870        880        890        900
       EVANTDGSMR TVLIWENLDR PRDIVVEPMG GYMYWTDWGA SPKIERAGMD ASGRQVIISS 910        920        930        940        950        960
       NLTWPNGLAI DYGSQRLYWA DAGMKTIEFA GLDGSKRKVL IGSQLPHPFG LTLYGERIYW 970        980        990       1000       1010       1020
       TDWQTKSIQS ADRLTGLDRE TLQENLENLM DIHVFHRRRP PVSTPCAMEN GGCSHLCLRS 1030       1040       1050       1060       1070       1080
       PNPSGFSCTC PTGINLLSDG KTCSPGMNSF LIFARRIDIR MVSLDIPYFA DVVVPINITM 1090       1100       1110       1120       1130       1140
       KNTIAIGVDP QEGKVYWSDS TLHRISRANL DGSQHEDIIT TGLQTTDGLA VDAIGRKVYW 1150       1160       1170       1180       1190       1200
       TDTGTNRIEV GNLDGSMRKV LVWQNLDSPR AIVLYHEMGF MYWTDWGENA KLERSGMDGS 1210       1220       1230       1240       1250       1260
       DRAVLINNNL GWPNGLTVDK ASSQLLWADA HTERIEAADL NGANRHTLVS PVQHPYGLTL 1270       1280       1290       1300       1310       1320
       LDSYIYWTDW QTRSIHRADK GTGSNVILVR SNLPGLMDMQ AVDRAQPLGF NKCGSRNGGC
```

Figure 9-3

```
         1330       1340       1350       1360       1370       1380
    SHLCLPRPSG FSCACPTGIQ LKGDGKTCDP SPETYLLFSS RGSIRRISLD TSDHTDVHVP 1390       1400       1410       1420       1430       1440
    VPELNNVISL DYDSVDGKVY YTDVFLDVIR RADLNGSNME TVIGRGLKTT DGLAVDWVAR 1450       1460       1470       1480       1490       1500
    NLYWTDTGRN TIEASRLDGS CRKVLINNSL DEPRAIAVFP RKGYLFWTDW GHIAKIERAN 1510       1520       1530       1540       1550       1560
    LDGSERKVLI NTDLGWPNGL TLDYDTRRIY WVDAHLDRIE SADLNGKLRQ VLVSHVSHPF 1570       1580       1590       1600       1610       1620
    ALTQQDRWIY WTDWQTKSIQ RVDKYSGRNK ETVLANVEGL MDIIVVSPQR QTGTNACGVN 1630       1640       1650       1660       1670       1680
    NGGCTHLCFA RASDFVCACP DEPDSRPCSL VPGLVPPAPR ATGMSEKSPV LPNTPPTTLY 1690       1700       1710       1720       1730       1740
    SSTTRTRTSL EEVEGRCSER DARLGLCARS NDAVPAAPGE GLHISYAIGG LLSILLILVV 1750       1760       1770       1780       1790       1800
    IAALMLYRHK KSKFTDPGMG NLTYSNPSYR TSTQEVKIEA IPKPAMYNQL CYKKEGGPDH 1810       1820       1830       1840       1850       1860
    NYTKEKIKIV EGICLLSGDD AEWDDLKQLR SSRGGLLRDH VCMKTDTVSI QASSGSLDDT 1870       1880       1890       1900
    ETEQLLQEEQ SECSSVHTAA TPERRGSLPD TGWKHERKLS SESQV
```

DETECTION AND TREATMENT OF LRP4-ASSOCIATED NEUROTRANSMISSION DISORDERS

CONTINUING APPLICATION DATA

This application is a continuation-in-part of International Application No. PCT/US2010/053483, filed Oct. 21, 2010, which claims the benefit of U.S. Provisional Application Ser. No. 61/253,610, filed Oct. 21, 2009; each of which is incorporated herein by reference in its entirety.

BACKGROUND

Myasthenia gravis is an autoimmune disease that causes dysfunction of the neuromuscular synapses. Seventy percent of patients with myasthenia gravis carry autoantibodies to the acetylcholine receptor (AChR) and a separate 10% carry autoantibodies to muscle specific tyrosine kinase (MuSK) (Vincent and Leite, 2005, Curr Opin Neurol; 18(5):519-25). However, twenty percent of patients with myasthenia gravis are seronegative for autoantibodies to AChR and MuSK. Thus, there is a need for improved diagnostic and treatment methods for neuromuscular disorders such as myasthenia gravis.

SUMMARY OF THE INVENTION

The present invention includes a method for diagnosing a neurotransmission or developmental disorder in a mammal, the method including detecting in a bodily fluid of the mammal autoantibodies that bind to the low density lipoprotein receptor-related protein 4 (LRP4), or an epitope thereof.

The present invention includes a method for diagnosing a neurotransmission or developmental disorder associated with interference of agrin/MuSKJLRP4/AChR neuromuscular junction formation or function in a mammal, the method including detecting in a bodily fluid of the mammal autoantibodies to an epitope of low density lipoprotein receptor-related protein 4 (LRP4), or an epitope thereof.

The present invention includes a method for diagnosing congenital and acquired muscle disorders associated with interference of agrin/MuSK/LRP4/AChR neuromuscular junction formation of functioning in a mammal, the method including detecting in a bodily fluid of the mammal autoantibodies to an epitope of low density lipoprotein receptor-related protein 4 (LRP4), or an epitope thereof.

The present invention includes a method of diagnosing myasthenia gravis in a mammal, the method including detecting autoantibodies to an epitope of the low density lipoprotein receptor-related protein 4 (LRP4) in a bodily fluid of the mammal. In some aspects, the myasthenia gravis is seronegative for autoantibodies to the acetylcholine receptor (AChR) and/or muscle specific tyrosine kinase (MuSK).

In some aspects, the detection methods of the present invention include contacting the bodily fluid with a LRP4 polypeptide or antigenic determinant thereof, and detecting any antibody-antigen complexes formed between said LRP4 polypeptide or antigenic fragment thereof and antibodies present in the bodily fluid; wherein the presence of antibody-antigen complexes is indicative of said mammal suffering from a neurotransmission or developmental disorder. In some aspects, the antibody-antigen complex is detected using a LRP4, epitope, or antigenic determinant thereof tagged or labeled with a reporter molecule. In some aspects, the antibody-antigen complex is detected using an anti-IgG antibody tagged or labeled with a reporter molecule. In some aspects, the reporter molecule may include any of a heavy metal, a fluorescent or luminescent molecule, radioactive or enzymatic tag. In some aspects, the enzymatic tag may include horseradish peroxidase-protein A. In some aspects, the reporter molecule may be a radioactive label. In some aspects, the label may be $^{125}$I.

The present invention includes an assay kit for diagnosing a neurotransmission disorder in a mammal, the kit including a LRP4 polypeptide or an epitope thereof. In some aspects of the assay kit, the LRP4 polypeptide or epitope thereof is immobilized on a solid surface. In some aspects of the assay kit, the LRP4 polypeptide or epitope thereof is recombinantly expressed by a transfected cell. In some aspects, the assay kit may further include a means for contacting said LRP4 polypeptide or epitope thereof with a bodily fluid of said mammal. In some aspects, the assay kit may further include an acetylcholine receptor polypeptide, or fragment thereof, and/or a muscle specific tyrosine kinase (MuSK) polypeptide, or fragment thereof. In some aspects of the assay kit, the assay kit further includes a secondary anti-human immunoglobulin antibody. In some aspects, the LRP4 polypeptide or epitope thereof has a detectable label thereon. In some aspects of the assay kit, the detectable label is $^{125}$I. In some aspects, the assay kit may detect myasthenia gravis, muscular dystrophy, or a congenital myasthenic syndrome. In some aspects the assay kit further includes a negative control and/or a positive control.

The present invention includes an isolated or purified antibody specific for an anti-LRP4 autoantibody from a bodily fluid of a mammal. In some aspects, the antibody inhibits the binding of an anti-LRP4 autoantibody to LRP4. In some aspects, the antibody may be conjugated to a reporter molecule. The present invention includes compositions including one or more such antibodies and a pharmaceutically acceptable carrier, diluent or excipient therefor. The present invention includes methods of treating a patient suffering from a neurotransmission disorder including administering to the patient an effective amount of such an antibody. The present invention includes diagnostic kits for detecting a neurotransmission disorder in a mammal, the diagnostic kit including one or more such antibodies. In some aspects, the diagnostic kit may further including a means for contacting the antibody with a bodily fluid of the mammal.

The present invention includes a method of identifying compounds capable of alleviating or treating a neurotransmission disorder, the method including contacting a candidate compound in the presence of LRP4 or an epitope thereof and an antibody capable of binding LRP4, wherein a compound that prevents binding of the antibody to LRP4 or an epitope thereof is a candidate for treating a neurotransmission disorder. The present invention includes compounds identified by such a method and methods of treating a patient suffering from a neurotransmission disorder including administering to said patient an effective amount of one or more such compounds. In some aspects, the neurotransmission disorder is myasthenia gravis, muscular dystrophy, or a congenital myasthenic syndrome. In some aspects, the neurotransmission disorder is seronegative for autoantibodies to the acetylcholine receptor (AChR) and/or muscle specific tyrosine kinase (MuSK).

The present invention includes a method of treating an individual suffering from a neurotransmission disorder, the method including detecting in a bodily fluid of the individual autoantibodies that bind to the low density lipoprotein receptor-related protein 4 (LRP4), or an epitope thereof, and administering to the patient an effective amount an immunosuppressant and/or another appropriate therapeutic modality.

The present invention includes a method for diagnosing a neurotransmission or developmental disorder in a mammal, the method including detecting a genetic mutation in the low density lipoprotein receptor-related protein 4 (LRP4) gene. In some aspects of the method, the genetic mutation may be an intronic mutation, an exonic mutation, a splice junction mutation, a point mutation, a missense mutation, an insertion mutation, a deletion mutation, an insertion-deletion mutation, alters one or more amino acids, a read through mutation, a frameshift mutation, affects mRNA splicing, introduces a stop codon, affects mRNA half life, affects mRNA transcription, affects mRNA translation, reduces LRP4 mRNA and/or protein expression, and/or prevents LRP4 mRNA and/or protein expression.

In some aspects of the methods for diagnosing a neurotransmission or developmental disorder, the method may further include providing a report or print out summarizing the binding of autoantibodies to the low density lipoprotein receptor-related protein 4 (LRP4), or an epitope thereof.

The present invention includes a method of treating an individual suffering from a neurotransmission disorder, the method including detecting a genetic mutation in the low density lipoprotein receptor-related protein 4 (LRP4) gene and administering to the patient an effective amount an immunosuppressant and/or another appropriate therapeutic modality.

In some aspects of the methods or kits of the present invention, the neurotransmission disorder is myasthenia gravis, muscular dystrophy, or a congenital myasthenic syndrome. In some aspects of the methods or kits of the present invention, the developmental disorder is muscle paralysis and/or fixed joints in newborn offspring due to maternal antibodies to LRP4. In some aspects of the methods or kits of the present invention, the neurotransmission or developmental disorder is seronegative for autoantibodies to the acetylcholine receptor (AChR) and/or muscle specific tyrosine kinase (MuSK).

In some aspects of the methods or kits of the present invention, a bodily fluid may include plasma, serum, whole blood, urine, sweat, lymph, feces, cerebrospinal fluid and nipple aspirate.

The present invention includes a model system for seronegative myasthenia gravis, the model system including a non-human mammal immunized with low density lipoprotein receptor-related protein 4 (LRP4), or an antigenic fragment thereof.

The present invention also includes a model system for seronegative myasthenia gravis, the model system including a non-human mammal passively immunized with serum from a seronegative myasthenia gravis subject, wherein a seronegative myasthenia gravis subject is seronegative for autoantibodies to the acetylcholine receptor (AChR) and/or muscle specific tyrosine kinase (MuSK).

BRIEF DESCRIPTION OF THE FIGURES

FIG. 1A shows the temporal expression pattern of LRP4 during muscle differentiation. C2C12 myoblasts were switched to the differentiation medium. Muscle cells were collected at indicated times and lyzed. Lysates (30 μg of protein) were resolved by SDS-PAGE and visualized by immunoblotting using indicated antibodies. FIG. 1B shows colocalization of LRP4 with R-BTX in muscle sections. Diaphragm sections were incubated with polyclonal antibodies against LRP4 or MuSK, which was visualized by Alexa Fluor 488-conjugated anti-rabbit antibody. R-BTX was included in the reaction to label postsynaptic AChRs. Arrows indicate co-localization of LRP4 or MuSK with AchR5. FIG. 1C shows enrichment of LRP4 in synaptic regions of muscles. Synaptic (S) and non-synaptic (NS) regions of hemidiaphragms were isolated and homogenized. Homogenates (30 μg of protein) were analyzed for LRP4 or AChR (as control) using specific antibodies. Samples were also probed for β-actin to indicate equal loading.

FIGS. 2A-2C show interaction of LRP4 and neuronal agrin in solution. Beads were conjugated with Flag-nAgrin, which were subsequently incubated with condition media of HEK293 cells expressing LRP4N-Myc (FIG. 2A), MuSKect-Myc (FIG. 2B), LRP6N-Myc (FIG. 2C), or empty vector (control). Bound proteins were isolated by bead precipitation, resolved by SDS-PAGE and visualized by immunoblotting with anti-Myc antibody. Flag-nAgrin interacted with LRP4N-Myc (FIG. 2A), but not MuSKect-Myc (FIG. 2B) or LRP6N-Myc (FIG. 2C). FIG. 2D shows interaction of Wnt-1 and LRP6N. Beads were conjugated with Wnt-1-HA, which were subsequently incubated with LRP6N-Myc. Bound LRP6N-Myc was revealed by immunoblotting. FIG. 2E demonstrates no interaction between Wnt-1 and LRP4N. Beads were conjugated with Wnt-1-HA, which were subsequently incubated with LRP4N-Myc. Bound LRP4N-Myc was revealed by immunoblotting.

FIG. 3A presents schematic diagrams of AP constructs. Neuronal or muscle agrin was fused to AP in pAPtag-5. The fusion proteins contain a signal peptide (SS) in the N-tenninus, and two additional tags (Myc and H is) in the C-terminus. Neuronal agrin contains 4- and 8-amino acid residue inserts at the Y and Z sites, respectively. FIG. 3B presents functional characterization of agrin-AP recombinant proteins. C2C12 myotubes were stimulated with AP alone, mAgrin-AP or nAgrin-AP for 18 hours (hr). AChR clusters were assayed as described in Experimental Procedures of Example 1. Data shown were mean±SEM. n=4; *, P<0.05 in comparison with AP or mAgrin-AP. FIG. 3C presents differential binding activities of mAgrin-AP and nAgrin-AP to myoblasts and myotubes. C2C12 myoblasts and myotubes were incubated AP alone, mAgrin-AP or nAgrin-AP for 90 minutes (min) at room temperature. Endogenous AP was inactivated by heating and bound AP was assayed by staining with BCIP/NBT. Data shown were mean±SEM. n=6; *, P<0.05. FIG. 3D shows direct interaction between LRP4 and neuronal agrin. LRP4-Myc was purified and coated on Maxi-Sorp Immuno Plates, which were incubated with nAgrin-AP or mAgrin-AP. AP activity was measured with pNPP as substrate. Control, condition medium of HEK293 cells transfected with the empty pAPtag-5. Data shown were mean±SEM. n=3; *, P<0.05 in comparison with AP or mAgrin-AP. FIG. 3E presents dose-dependent interaction between LRP4 and neuronal Agrin. Purified LRP4-Myc was coated on Maxi-Sorp Immuno Plates, which were incubated with nAgrin-AP or mAgrin-AP. AP activity was measured with pNPP as substrate. Data shown were mean±SEM. n=4; *, P<0.05. FIG. 3F is a Scatchard plot of data in FIG. 3E. Y axis represents the ratio of bound to free nAgrin-AP whereas X axis represents the concentration of bound nAgrin-AP.

FIG. 4A shows neuronal, but not muscle, agrin bound to intact C2C12 myoblasts transfected with LRP4. C2C12 myoblasts were transfected by empty vector (control), LRP4 and/or Flag-MuSK. 36 hr after transfection, myoblasts were incubated with AP alone, mAgrin-AP or nAgrin-AP for 90 min at room temperature. Endogenous AP was inactivated by heating and bound AP was visualized in cells by staining with BCIP/NBT. FIG. 4B is a quantification of data in FIG. 4A. Data shown were mean±SEM. n=6; *, P<0.05 in comparison with mAgrin-AP of the same group or nAgrin-AP in the control group. FIGS. 4C and 4D show nAgrin-AP bound to HEK293 cells expressing LRP4, but not those expressing LRP5. HEK293 cells were transfected without (control) or with LRP4-Myc (FIG. 4C) or LRP5-Myc (FIG. 4D). 36 hr after transfection, transfected cells were incubated with nAgrin-AP or mAgrin-AP. In some experiments, control cells were incubated with nAgrin-AP. After heat inactivation of endogenous AP, lysates were assayed for transfected AP using pNPP as substrate. Lysates were also subjected to immunoblotting to reveal the expression of different amounts of LRP4-Myc (FIG. 4C) and LRP5-Myc (FIG. 4D). Data shown were mean±SEM. n=6. FIGS. 4E and 4F show LRP4 expression enabled MuSK and Abl activation by agrin in HEK293 cells. Cells were transfected with LRP4 and/or Flag-MuSK (FIG. 4E) or Flag-Abl (FIG. 4F). 36 hr after transfection, cells were treated without or with neuronal agrin for 1 hr and were then lyzed. In FIG. 4E, lysates were incubated with anti-Flag antibody, and resulting immunocomplex was analyzed with anti-phosphotyrosine antibody 4G10. In FIG. 4F, active Abl was revealed by immunoblotting with specific phospho-Abl antibody. Lysates were also blotted for Flag and/or Myc, LRP4, or β-actin to indicate equal amounts of proteins. FIG. 4G is a quantitative analysis of data in E and F. MuSK and Abl phosphorylation was quantified by using the ImageJ software. Data shown were mean±SEM. n=3; *, P<0.05 in comparison with control.

FIG. 5A is a characterization of LRP4-miRNA constructs. HEK293 cells were transfected with LRP4 and LRP4-miLRP4 constructs or control miRNA that encoded scrambled sequence. Cell lysates were analyzed for LRP4 expression by immunoblotting with anti-LRP4 antibody. β-Actin was used as loading control. miLRN4-1062 was most potent in inhibiting LRP4 expression. FIG. 5B shows repression of LRP4 expression reduced neuronal agrin binding to myotube surface. C2C12 myotubes were transfected with control (scramble) miRNA or miLRP4-1062. Cells were incubated with AP, mAgrin-AP or nAgrin-AP, which was visualized in cell as described in FIG. 3A. FIG. 5C is a quantitative analysis of data in FIG. 5B. Data shown were mean±SEM. n=6; *, p<0.05 in comparison nAgrin-AP with control. FIG. 5D shows MuSK activation by neuronal agrin was diminished in C2C12 myotubes transfected with rniLRP4-1062. C2C12 myotubes were transfected with control miRNA or miLRP4-1062. 36 hr later, myotubes were treated without or with agrin for 1 hr and cells were then lyzed. MuSK was isolated by immunoprecipitation and blotted with the anti-phosphotyrosine antibody 4G10. Lysates were also blotted for MuSK, LRP4, GFP (encoded by miRNA constructs), and β-actin to indicate equal amounts of proteins. FIG. 5E is a quantitative analysis of data in D by ImageJ software (mean±SEM, n=3; *, P<0.05 in comparison with control). FIG. 5F shows neuronal agrin-induced clustering of AChRs was inhibited in C2C12 myotubes transfected with miLRP4-1062. C2C12 myotubes were transfected by control miRNA, miLRP4-1062, miMuSK-1161, or miLRP5-1490. AChR clusters were induced by neuronal agrin and quantified as described in Experimental Procedures (mean±SEM, n=5; *, p<0.05 in comparison with control). miMuSK1161 and miLRP5-1490 were able to suppress expression of respective proteins in transfected cells.

FIG. 6A shows increased LRP4-MuSK interaction in the presence of neuronal agrin. Flag-MuSKect immobilized on beads were incubated with condition media of cells expressing the extracellular domains of LRP4 (LRP4N-Myc) or the empty vector (control) in the presence or absence of neuronal agrin. Precipitated LRP4 was analyzed by immunoblot with anti-Myc antibody. Reaction mixtures were also blotted directly for Flag and Myc to demonstrate equal amounts of proteins. FIG. 6B is a quantitative analysis of LRP4N-Myc and Flag-MuSK. Data shown were mean±SEM, n=3; *, p<0.05 in comparison with the no-agrin group. FIG. 6C shows a dose-dependent interaction between LRP4 and MuSK. Purified LRP4-Myc was coated on Maxi-Sorp Immuno Plates, which were incubated with MuSK-AP. Bound AP was measured with pNPP as substrate. Data shown were mean±SEM. n=4. FIG. 6D is a Scatchard plot of data in FIG. 6C. Y axis represents the ratio of bound to free MuSK-AP whereas X axis represents the concentration of bound MuSK-AP. FIG. 6E shows no interaction of LRP6 and MuSK extracellular domains. Experiments were done as in FIG. 6A except condition medium of cells expressing the extracellular domain of LRP6 was used. FIG. 6F shows co-immunoprecipitation of LRP4 and MuSK. HEK293 cells were transfected with LRP4 and/or Flag-MuSK. Lysates were incubated with anti-Flag antibody, and resulting immunocomplex was analyzed for LRP4 and Flag. Lysates were also probed to indicate equal amounts of indicated proteins. FIG. 6G shows interaction of LRP4 with MuSK in mouse muscles. Mouse muscles of indicated ages were homogenized, and homogenates were incubated with rabbit anti-LRP4 antibody or rabbit normal IgG. Precipitates were probed for MuSK and LRP4. Homogenates were also probed directly for MuSK, LRP4, and β-actin (bottom panels).

FIG. 7. Agrin stimulates the LRP4-MuSK interaction and LRP4 tyrosine phosphorylation. FIG. 7A shows agrin stimulated the interaction between endogenous LRP4 and MuSK. C2C12 myotubes were stimulated without or with neuronal agrin. Lysates were subjected to immunoprecipitation with rabbit anti-LRP4 antibody (top panels) or rabbit normal IgG (middle panels). Resulting precipitates were probed for MuSK or LRP4. Lysates were also probed with antibodies against LRP4, MuSK, or β-actin to demonstrate equal amounts (bottom panels). FIG. 7B is a quantitative analysis of data in FIG. 7A by using the ImageJ software (mean±SEM, n=3; *, P<0.05 in comparison with the no-agrin group). FIG. 7C shows agrin stimulated tyrosine phosphorylation of LRP4 in muscle cells. C2C12 myotubes were treated without or with agrin for 1 hr. Lysates were subjected to immunoprecipitation with antibodies against LRP4 and MuSK, respectively. Resulting precipitates were probed with anti-phospho-tyrosine antibody 4G10, or antibodies against LRP4 and MuSK, respectively, to indicate equal amounts of precipitated proteins. FIG. 7D is a quantitative analysis of data in FIG. 7C. Data shown were mean±SEM, n=3; *, p<0.05 in comparison with no-nAgrin. FIG. 7E presents a working model. In the absence of neuronal agrin, LRP4 could interact with MuSK and this interaction is increased by agrin stimulation. Such interaction is necessary for MuSK activation and downstream signaling that leads to AChR clustering. P, phosphorylation.

FIG. 8A shows attenuation of agrin-induced AChR clustering by the extracellular domain of LRP4. C2C12 myotubes were treated without (control) or with neuronal agrin (nAgrin) or nAgrin that was pre-incubated with LRP4N-Myc immobilized on beads for 18 hr. Representative myotubes were shown. FIG. 8B is a quantitative analysis of data in FIG. 8A. Data shown were mean±SEM, n=5; *, p<0.05 in comparison with nAgrin. FIG. 8C shows inhibition of MuSK phosphorylation by the extracellular domain of LRP4. C2C12 myotubes were treated as in FIG. 8A, except for 1 hr. Lysates were subjected to immunoprecipitation with rabbit anti-MuSK antibody. Resulting precipitates were probed with the anti-phospho-tyrosine antibody 4G10. Precipitates were also probed with anti-MuSK antibody to demonstrate equal amounts. FIG. 8D is a quantitative analysis of data in FIG. 8C. Data shown were mean±SEM, n=3; *, p<0.05 in comparison with the no-agrin group.

FIG. 9. Amino acid sequence of human low density lipoprotein receptor-related protein 4 (LRP4) precursor (SEQ ID NO:11).

FIG. 10A shows structures of LRP4 and C-terminus-tagged ecto-LRP4. FIG. 10B shows preparation of ecto-LRP4. Ecto-LRP4 was purified from transfected HEK293 cells by affinity chromatography and subjected to western blotting by anti-Myc antibody. Arrow indicates LRP4.

FIG. 16A shows reduced body weight in ecto-LRP4-injected mice (p=0.02). FIG. 16B shows reduced grip strength in ecto-LRP4-injected mice (p=0.004). FIG. 16C shows one mouse, representative of most severely affected LRP4 EAMG mice, with chin down and flaccid tail. FIG. 16D shows LRP4 immunoreactivity in LRP4-injected mice was increased.

DETAILED DESCRIPTION OF ILLUSTRATIVE EMBODIMENTS OF THE PRESENT INVENTION

Figure 1:
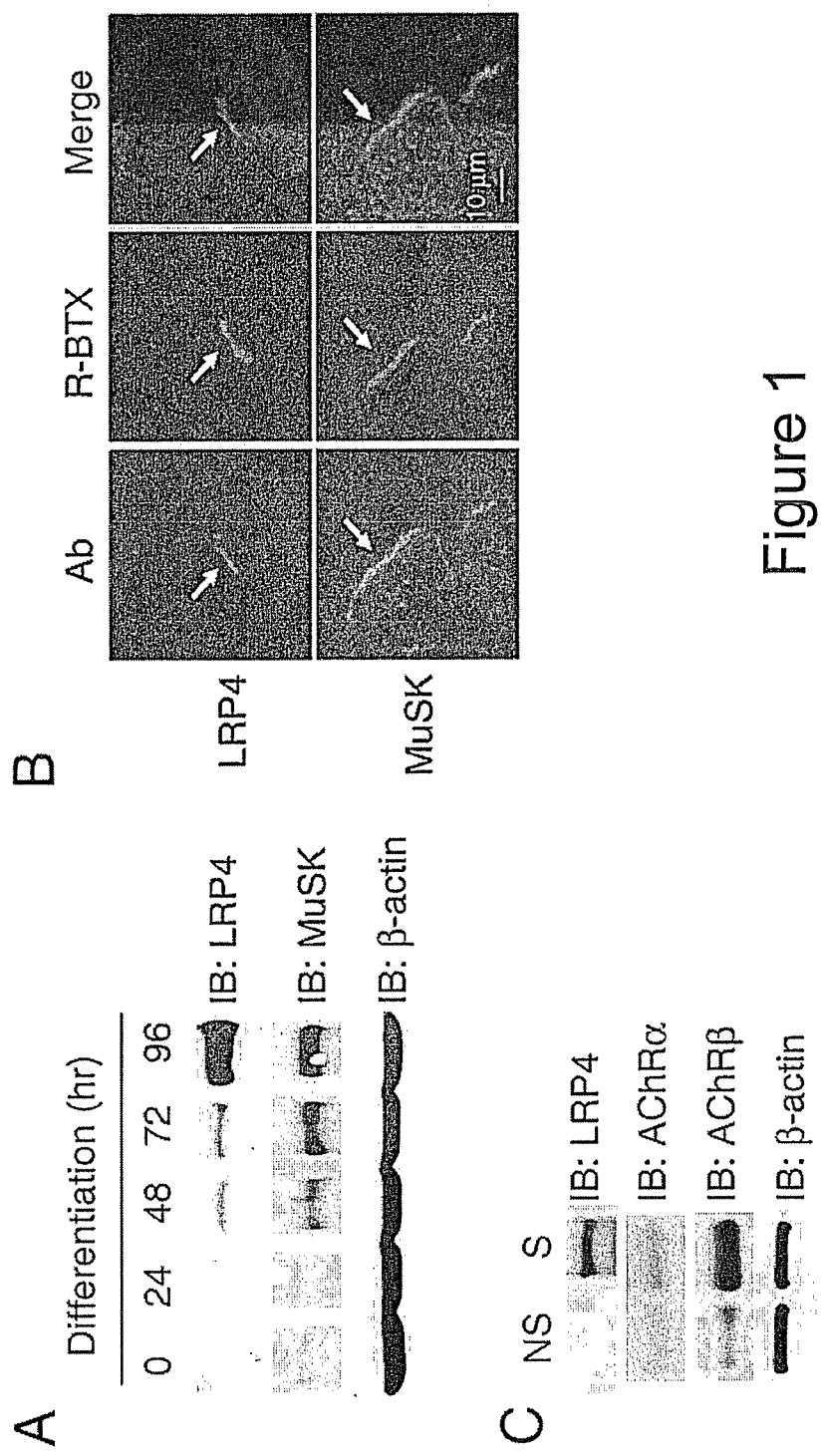
FIG. 1. LRP4 is specifically expressed in myotubes and concentrated at the NMJ.

The present invention identifies the low density lipoprotein receptor-related protein 4 (LRP4) as the postsynaptic receptor for agrin, demonstrates that LRP4 and muscle specific tyrosine kinase (MuSK) associate, and provides the first demonstration of the association of autoantibodies to LRP4 with a subset of seronegative myasthenia gravis (MG). Included in the present invention are methods for diagnosing a neurotransmission or developmental disorder in a subject by detecting autoantibodies that bind to the low density lipoprotein receptor-related protein 4 (LRP4), or an antigenic epitope thereof, in a sample obtained from the individual. Such a neurotransmission or developmental disorder may be associated with interference of agrin/MuSK/LRP4/AChR neuromuscular junction formation or function in a mammal. A neurotransmission or developmental disorder may be a congenital or acquired muscle disorder associated with interference of agrin/MuSK/LRP4/AChR neuromuscular junction formation or functioning.

Neurotransmission disorders include, but are not limited to, myasthenia gravis, muscular dystrophy, and congenital myasthenic syndrome (CMS). Congenital myasthenic syndromes are heterogeneous disorders in which neuromuscular transmission is compromised by one or more specific mechanisms. See, for example, Engel, 2008, *Handb Clin Neural;* 91:285-331. A developmental disorder includes, but is not limited to, muscle paralysis and/or fixed joints in newborn offspring due to maternal antibodies to LRP4.

Myasthenia gravis (MG) is an autoimmune disease that causes dysfunction of the neuromuscular synapses. Seventy percent of patients with myasthenia gravis carry autoantibodies to the acetylcholine receptor (AChR) and a separate 10% carry autoantibodies to muscle specific tyrosine kinase (MuSK). However, twenty percent of patients with myasthenia gravis are seronegative for autoantibodies to AChR and MuSK. A neurotransmission disorder may be seronegative for autoantibodies to the AChR, including myasthenia gravis in patients who are anti-AChR autoantibody negative (AAAN). A neurotransmission disorder may be seronegative for autoantibodies to MuSK, including myasthenia gravis in patients who are anti-MuSK autoantibody negative. The MuSK protein has been sequenced and the protein characterized recently by Valenzuela et al. (PCT/US96/20696, published as WO97/21811). It is a receptor tyrosine kinase (RTK) located on the cell surface of muscle cells at the neuromuscular junction. Methods of detecting autoantibodies to the MuSK protein for the diagnosis of neuromuscular disorders are described, for example, in U.S. Pat. No. 7,267,820. A neurotransmission disorder may be seronegative for autoantibodies to both the AChR and MuSK, including myasthenia gravis in patients who are anti-AChR autoantibody negative (AAAN) and anti-MuSK auto antibody negative. Such a neurotransmission disorder may be moderate or severe generalized MG in which a standard radio-immunoprecipitation assay for anti-AChR antibodies and/or anti-MuSK antibodies is negative on several occasions.

A neurotransmission disorder, such as MG, may be characterized by fatigable muscle weakness and may be confirmed, for example, by electromyographic evidence of a defect in neuromuscular transmission (for example, a decrement of more than about 10% in the amplitude of the compound muscle action potential on repetitive nerve stimulation at 3 Hz and/or an increase in jitter on single fiber studies), or by a positive response to anticholinesterase medication (edrophonium or pyridostigmine).

LRP4 (or MEGF7, for multiple epidermal growth factor (EGF)-like domain 7) is a member of the LDLR family, and contains a large extracellular N-terminal region that possesses multiple EGF repeats and LDLR repeats, a transmembrane domain and a short C-terminal region without an identifiable catalytic motif (Johnson et al., 2005, *Hum Mol Genet;* 14:3523-3538; Lu et al., 2007, *Brain Res;* 1177:19-28; Tian et al., 2006, *Eur J Neurosci;* 23:2864-2876; Yamaguchi et al., 2006, *Gene Expr Patterns;* 6:607-612). It was identified by a motif trap screen of genes encoding proteins with multiple EGF domains (Nakayama et al., 1998, *Genomics;* 51:27-34).

With the methods, antibodies, and kits of the present invention, a LRP4 polypeptide may be from a mammal, including, for example, human, mouse, or rat. A fragment of a LRP polypeptide may include an antigenic epitope and be bound by an antibody. A fragment may include the extracellular domain. A fragment may include the intracellular domain. A fragment thereof may include one or more EGF repeats and/or one or more LDLR repeats of the LRP4 polypeptide. LRP4 genomic and amino acid sequences are available for a variety of mammals, including, but not limited to mouse (see, for example, informatics.jax.org/searches/accession_report.cgi?id=MGI:2442252 on the worldwide web), rat (see, for example, RGD ID 619731; and rgd.mcw.eduitools/genes/genes_view.cgi?id=619731 on the worldwide web), and human (see, for example, Naayama et al., Genomics 1998, 51(1):27-34; GENBANK Accession No. NM_002334; and UniProtKB/Swiss-Prot 075096). Human lipoprotein receptor-related protein 4 (LRP4) polypeptide includes, but is not limited to, the LRP4 polypeptide produced from the amino acid sequence shown in FIG. 9.

The present invention includes methods for diagnosing a neurotransmission or developmental disorder in a subject by detecting in a bodily fluid obtained from the individual autoantibodies that bind to the low density lipoprotein receptor-related protein 4 (LRP4), or an antigenic fragment thereof (also referred to herein as "antigenic determinant" or "epitope thereof"). Such methods may include a determination of binding, or lack of binding to, a acetylcholine receptor polypeptide, or fragment thereof, and/or a muscle specific tyrosine kinase (MuSK) polypeptide, or fragment thereof. Such methods may further include a determination of binding, or lack of binding to, any of a variety of other cell determinant, including, but not limited to, any of those described by Wandinger et al., 2012, *J Lab Med* (Article in Press) ("New serological markers for the differential diagnosis of autoimmune limbic encephalitis;" K. Wandinger, C. Klingbeil, C. Gneiss, P. Waters, J. Dalmau, S. Saschenbrecker, K. Borowski, F. Deisenhammer, A. Vincent, C. Probst, and W. Stöcker, 2012; original German online version available on the worldwide web at: degruyter.com/view/j/labm.2011.35.issue-6/issue-files/labm.2011.35.issue-6.xml).

Autoantibodies may be detected by any of a variety of methods, including, but not limited to, any of those described herein, any of those described, for example by Jurius et al. 2010, *J Neurol Sci* 291(1-2):52-6; Wandinger et al., 2011, *J Neuroimmunol;* 231(1-2):86-91; and Wandinger et al., 2012, *J Lab Med* (Article in Press) ("New serological markers for the differential diagnosis of autoimmune limbic encephalitis;" K. Wandinger, C. Klingbeil, C. Gneiss, P. Waters, J. Dalmau, S. Saschenbrecker, K. Borowski, F. Deisenhammer, A. Vincent, C. Probst, and W. Stöcker, 2012; original German online version available on the worldwide web at: degruyter.com/view/j/labm.2011.35.issue-6/issue-files/labm.2011.35.issue-6.xml), and any suitable method available to the skilled artisan.

Immunoassays that can be used include, but are not limited to, competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), immunoprecipitation assays (IPA), immunohistochemistry (IHC) assays, recombinant immunofluorescence assays (rIFA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, cell based assays, biochip assays, and multiplex assays, to name but a few. Such assays are routine and well known in the art. Such assays may or may not include the preabsorption of sera. With any of the methods of the present invention, the intensity of a signal from an anti-human immunoglobulin autoantibody may be indicative of the relative amount of the anti-LRP4 autoantibody in the bodily fluid when compared to a positive and negative control reading.

With any of the methods of the present invention, an antibody-antigen complex may be detected for example, by using a LRP4, or antigenic determinant thereof tagged or labeled with a reporter molecule or an anti-immunoglobulin antibody tagged or labeled with a reporter molecule. An anti-immunoglobulin antibody may include, but is not limited to, an anti-IgG, an anti-IgM, an anti-IgG1, or and anti-IgG4 antibodies. A reporter molecule may be, for example, a heavy metal, a fluorescent or luminescent molecule, a radioactive tag (such as, for example, said label is $^{125}$I), and an enzymatic tag (such as, for example, horseradish peroxidase-protein A followed by reaction with o-phenylenediamine for subsequent measurement at $A^{492}$)

The actual steps of detecting autoantibodies in a sample of bodily fluids may be performed in accordance with immunological assay techniques known in the art. An assay may use an antigen which may be immobilized on a solid support. In some embodiments, cells recombinantly expressing LRP4, or antigenic determinant thereof (such as, for example, an extracellular region of LRP4), may be immobilized on a solid support. In some embodiments, such cells may be fixed, such as, for example, fixed with formaldehyde.

A sample to be tested may be brought into contact with the antigen or a cell expressing the antigen and if autoantibodies specific to the protein are present in a sample they will immunologically react with the antigen to form autoantibody-antigen complexes which may then be detected or quantitatively measured. Detection of autoantibody-antigen complexes may be carried out using a secondary anti-human immunoglobulin antibody, for example, anti-IgG or anti-human IgM, which recognizes general features common to all human IgGs or IgMs, respectively. A secondary antibody may be conjugated to an enzyme such as, for example, horseradish peroxidase (HRP) so that detecting of autoantibody/antigen/secondary antibody complexes is achieved by addition of an enzyme substrate and subsequent calorimetric, chemiluminescent or fluorescent detection of the enzymatic reaction products.

Thus, in one embodiment the antibody/antigen complex may be detected by a further antibody, such as an anti-IgG antibody. Complexes may alternatively be viewed by microscopy. Other labels or reporter molecules which may be used in a method according to the invention. A reporter molecule or label may include any of a heavy metal, a fluorescent or luminescent molecule, radioactive or enzymatic tag. The label or reporter molecule may be such that the intensity of the signal from the anti-human IgG antibody is indicative of the relative amount of the anti-LRP4 autoantibody in the bodily fluid when compared to a positive and negative control reading.

An alternative method of detecting autoantibodies for LRP4 or an epitope thereof relies upon the binding of LRP4 or its epitope, together with a revealing label, to the autoantibodies in the serum or bodily fluid. This method may include contacting LRP4 or an epitope or antigenic determinant thereof having a suitable label thereon, with a bodily fluid, immunoprecipitating any antibodies from the bodily fluid and monitoring for label on any of the antibodies, wherein the presence of label may be indicative of a mammal suffering from a neurotransmission or developmental disorder. The label may be a radioactive label, such as for example, $^{125}$I, or the like. Iodination and immunoprecipitation are standard techniques in the art.

Any of the diagnostic methods described herein may include the additional step of providing a report or print out summarizing the binding of autoantibodies in a sample to the low density lipoprotein receptor-related protein 4 (LRP4), or an epitope thereof. For any method disclosed herein that includes discrete steps, the steps may be conducted in any feasible order. And, as appropriate, any combination of two or more steps may be conducted simultaneously.

Any of the diagnostic methods described herein may include providing the subject with an effective amount an immunomodulatory therapy and/or another appropriate therapeutic modality. Immunomodulatory therapy may be immunosuppressive and may include, for example, steroids, splenectomy, plasmapheresis, intravenous immunoglobulin (such as, for example, antithymocyte globulin (ATG) or anti-lymphocyte globulin (ALG)), monoclonal antibodies, radiation, and/or any of a wide variety of immunosuppressive drugs (including, but not limited to, cyclophosphamide, methotrexate, azathioprine, mercaptopurine, cyclosporine, tacrolimis, sirolimus, TNF binding agents, and IL-2 receptor binding agents).

The present invention includes assay kits for diagnosing a neurotransmission disorder in a mammal. Such kits may include a LRP4 polypeptide or an epitope thereof. The LRP4 polypeptide or fragment thereof may be immobilized on a solid surface. Such kits may include a cell expressing a LRP4 polypeptide or an epitope thereof. Such expression may be natural or recombinant. The LRP4 polypeptide, fragment thereof, or cell may be immobilized on a solid surface. Such kits may further include means for contacting the substrate with a bodily fluid from a mammal. Thus, an assay system for detecting neurotransmission disorders, including myasthenia gravis in patients who are anti-AChR autoantibody negative (AAAN) and anti-MuSK auto antibody negative is provided. Prior to the present invention there was no basis for providing an immediate clinical diagnosis for such patients.

Such kits may further include a acetylcholine receptor polypeptide, or fragment thereof, and/or a muscle specific tyrosine kinase (MuSK) polypeptide, or fragment thereof. Such kits may further cells expressing a acetylcholine receptor polypeptide, or fragment thereof, and/or expressing a muscle specific tyrosine kinase (MuSK) polypeptide, or fragment thereof. Such expression may be natural or recombinant. Such polypeptides, fragments thereof, or cells may be immobilized on a solid surface. Such kits may further include further markers, including, but not limited to, any of those described in Wandinger et al., 2012, *J Lab Med* (Article in Press) ("New serological markers for the differential diagnosis of autoimmune limbic encephalitis;" K. Wandinger, C. Klingbeil, C. Gneiss, P. Waters, J. Dalmau, S. Saschenbrecker, K. Borowski, F. Deisenhammer, A. Vincent, C. Probst, and W. Stöcker, 2012; original German online version available on the worldwide web at: degruyter.com/view/j/labm.2011.35.issue-6/issue-files/labm.2011.35.issue-6.xml.

In some embodiments of kits and methods of the present invention, LRP4, AchR, MuSK polypeptides, and/or other polypeptides, fragments thereof or cells expressing such polypeptides or fragments thereof, may have a detectable label thereon, including, but not limited to, $^{125}$I. In some embodiments of kits and methods of the present invention, binding of an autoantibody may be detected by a secondary antibody. Thus, a kit may further include one or more secondary anti-human immunoglobulin antibodies. The assay kits and methods of the present invention may also include appropriate negative controls and/or a positive controls. Kits of the present invention may include other reagents such as buffers and solutions needed to practice the invention are also included. Optionally associated with such container(s) can be a notice or printed. instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

Also provided by the invention is an isolated or purified autoantibody specific for LRP4. Such an antibody can be detected in bodily fluids of mammals and isolated or purified therefrom using techniques which would be known to the skilled practitioner, such as, immunoabsorption, or immunoaffinity chromatography or high pressure chromatography.

The present invention includes isolated or purified antibodies that specifically bind an anti-LRP4 autoantibody from a bodily fluid of a mammal. Such an antibody may inhibit the binding of an anti-LRP4 autoantibody to LRP4. Such an antibody may be conjugated to a reporter molecule. The present invention includes diagnostic kit for detecting neurotransmission disorders including one or more such antibodies. The present invention includes methods of treating an individual suffering from a neurotransmission disorder by administering an effective amount of an antibody antibodies specific for an anti-LRP4 autoantibody.

As used herein, specific binding means binding that is measurably different from a non-specific interaction. Specific binding can be measured, for example, by determining binding of a molecule compared to binding of a control molecule, which generally is a molecule of similar structure that does not have binding activity, for example, an antibody that binds a distinct epitope or antigen. Specificity of binding also can be determined, for example, by competition with a control molecule, for example, competition with an excess of the same molecule. In this case, specific binding is indicated if the binding of a molecule is competitively inhibited by itself. Thus, specific binding between an antibody and antigen is measurably different from a non-specific interaction and occurs via the antigen binding site of the antibody.

An antibody may be an intact antibody, an antibody binding fragment, or a chimeric antibody. A chimeric antibody may include both human and non-human portions. An antibody may be a polyclonal or a moncoclonal antibody. An antibody may be a derived from a wide variety of species, including, but not limited to mouse and human. An antibody may be a humanized antibody. An antibody may be linked to another functional molecule, for example, another peptide or protein, a toxin, a radioisotope, a cytotoxic agent, cytostatic agent, a polymer, such as, for example, polyethylene glycol, polypropylene glycol or polyoxyalkenes. The antibodies of the present invention include various antibody fragments, also referred to as antigen binding fragments, which include only a portion of an intact antibody, generally including an antigen binding site of the intact antibody and thus retaining the ability to bind antigen. Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s).

Antibodies include, but are not limited to, polyclonal antibodies, affinity-purified polyclonal antibodies, monoclonal antibodies, human antibodies, humanized antibodies, chimeric antibodies, anti-idiotypic antibodies, multispecific antibodies, single chain antibodies, single-chain Fvs (scFv), disulfide-linked Fvs (sdFv), Fab fragments, F(ab') fragments, F(ab')2 fragments, Fv fragments, diabodies, linear antibodies fragments produced by a Fab expression library, fragments comprising either a VL or VH domain, intracellularly-made antibodies (i.e., intrabodies), and antigen-binding antibody fragments thereof.

An antibody of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

An antibody of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

The term "polyclonal antibody" refers to an antibody produced from more than a single clone of plasma cells. In contrast "monoclonal antibody" refers to an antibody produced from a single clone of plasma cells. The preparation of polyclonal antibodies is well known. Polyclonal antibodies may be obtained by immunizing a variety of warm-blooded animals such as horses, cows, goats, sheep, dogs, chickens, rabbits, mice, hamsters, guinea pigs and rats as well as transgenic animals such as transgenic sheep, cows, goats or pigs, with an immunogen. The resulting antibodies may be isolated from other proteins by using an affinity column having an Fc binding moiety, such as protein A, or the like.

Monoclonal antibodies can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

A therapeutically useful antibody may be derived from a "humanized" monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. The constant region of a humanized monoclonal antibody of the present invention can be that from human immunoglobulin belonging to any isotype. It may be, for example, the constant region of human IgG.

An antibody which is specific for anti-LRP4 autoantibodies may be used in an immunoadsorption therapy for the treatment of a neurotransmission disorder, including, but not limited to, seronegative myasthenia gravis.

An antibody which is specific for anti-LRP4 autoantibodies may be used in a diagnostic kit for detecting neurotransmission disorders, including, but not limited to, seronegative myasthenia gravis. Such a kit may include one or more isolated or purified antibodies specific for anti-LRP4 autoantibody. Such a kit may further include a means for contacting the antibody with a bodily fluid.

In accordance with the present invention a bodily fluid may be, for example, plasma, serum, whole blood, urine, sweat, lymph, feces, cerebrospinal fluid or nipple aspirate. In some embodiments, the methods of the invention will be performed on samples of serum or plasma.

The present invention includes methods of identifying compounds capable of alleviating or treating a neurotransmission disorder. Such methods include contacting an anti-LRP4 antibody and a LRP4 polypeptide, or fragment thereof, in the presence a candidate compound and determining the amount of antibody-LRP4 polypeptide binding, and identifying compounds that prevent or inhibit the binding of the anti-LRP4 antibody to the LRP4 polypeptide or fragment thereof. The present invention includes compounds identified by such methods.

Such methods of identifying compounds capable of alleviating or treating neurotransmission disorders may include the steps of contacting a candidate compound in the presence of LRP4, or an epitope thereof, and an antibody capable of binding LRP4, wherein a compound that prevents binding of the antibody to LRP4 or an epitope thereof is a candidate for treating neurotransmission disorders. Such compounds may also be used in treating neurotransmission or developmental disorders or in the manufacture of a medicament for treating such disorders. The compounds identified may also, as would be appreciated by those of skill in the art, serve as lead compounds for the development of analogue compounds. The analogues should have a stabilized electronic configuration and molecular conformation that allows key functional groups to be presented to the polypeptides of the invention in substantially the same way as the lead compound. In particular, the analogue compounds have spatial electronic properties which are comparable to the binding region, but can be smaller molecules than the lead compound, frequently having a molecular weight below about 2 kilodaltons (kD) and preferably below about 1 kD. Identification of analogue compounds can be through the use of techniques such as, for example, self-consistent field (SCF) analysis, configuration interaction (CI) analysis, and normal mode dynamics analysis. Computer programs for implementing these techniques are available; e.g., Rein, Computer-Assisted Modelling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, derivatives and analogues can be tested for their effects according to methods known in the art. Furthermore, peptidomimetics and/or computer aided design of appropriate derivatives and analogues can be used.

The present invention includes methods of treating a subject suffering from a neurotransmission disorder, the method including first determining that a bodily fluid of the individual contains autoantibodies that bind to the low density lipoprotein receptor-related protein 4 (LRP4), or an epitope thereof, followed by providing one or more appropriate therapeutic modalities to the individual. The method may include additional steps determining whether or not the bodily fluid contains autoantibodies that bind to the AchR, determining whether or not the bodily fluid contains autoantibodies that bind to MuSK, and/or determining whether or not the bodily fluid contains autoantibodies to additional cell determinants. Treatment may include, but is not limited to, administering an effective amount of one or more immunosuppressant agents, plasma exchange, antigen-specific immunoadsorption, and additional appropriate therapeutic modalities. This aspect of the invention is particularly advantageous because the identification of this new subclass or subtype of MG patients will allow for more accurate and speedy diagnosis of individuals by medical practitioners. The method according to this aspect of the invention will allow for detection of neurotransmission abnormalities that are either congenital or acquired, for example, postnatally or prenatally from transmission from the mother to the fetus.

Autoimmune myasthenia gravis (MG) is the most common disorder of the neuromuscular synapse, affecting 10 to 20 per 100,000 people. MG involves a fatiguing weakness of the voluntary muscles with a characteristic decrement in the compound muscle action potential (CMAP) on repetitive stimulation of the motor nerve. In approximately 80% of patients, auto-antibodies to the muscle nicotinic acetylcholine receptor (AChR) are present. These antibodies cause loss of AChR numbers and function, and lead to failure of neuromuscular transmission with muscle weakness. Although most cases of MG are caused by autoantibodies against AChR, about 20% of cases display no anti-AChR antibodies. In 2001, antibodies against MuSK (muscle specific tyrosine kinase) were identified in a proportion of patients with generalized MG (Hoch et al., 2001, *Nat Med;* 7(3):365-8). MuSK is a key organizer of NMJ formation. MuSK is required for clustering of AChR during the formation of NMJ and is expressed predominantly at the postsynaptic membrane in mature NMJ. In MuSK knockout mice, muscle fibers do not form aneural clusters or "prepattern" prior to innervation and do not form the NMJ, and AChRs fail to cluster opposite to growing motoneuron terminals on the surfaces of myotubes, suggesting a critical role of MuSK for both muscle fiber prepatterning and nerve-induced AChR clusters. Additionally, a case of heteroalleric MuSK mutations that caused the reduction of MuSK expression has been associated with congenital myasthenic syndrome (CMS).

Recent studies by Vincent and others showed that the frequency of MuSK antibodies in MG patients who were AChR seronegative (that is, lacked autoantibodies to the AchR) varied from 4 to 50%. MuSK antibodies interfere with the agrin/MuSK/AChR clustering in myotubes and alter MuSK function at the adult NMJ. The observation that rabbits immunized with the MuSK ectodomain manifested muscular weakness typical of MG and diminished AChR clustering at the NMJ provided a direct proof for the pathogenic role of anti-MuSK antibodies. See, for example, ter Beek et al., 2009, *Am J Pathol*; October; 175(4):1536-44 (Epub 2009 Sep. 10); Lang and Vincent, 2009, *Curr Opin Pharmacol*; June; 9(3):336-40 (Epub 2009 May 8); Littleton et al., 2009, *Mol Cell Proteomics*; July; 8(7):1688-96 (Epub 2009 Mar. 29); Beeson et al., 2008, *Ann NY Acad Sci;* 1132:99-103; Vincent et al., 2008, *Ann NY Acad Sci;* 1132:84-92; Leite et al., 2008, *Brain;* 131(Pt 7):1940-52; Farrugia et al., 2007, *J Neuroimmunol;* 185(1-2):136-44; Deymeer et al., 2007, *Neurology;* 68(8):609-11; Farrugia et al., 2007, *Clin Neurophysiol;* 118(2):269-77; Vincent, 2006, *Acta Neurol Scand Suppl;* 183:1-7; Farrugia et al., 2006, *Muscle Nerve;* 33(4):568-70; Benveniste et al., 2005, *J Neuroimmunol;* 170(1-2):41-8; Vincent and Leite, 2005, *Curr Opin Neurol;* 18(5):519-25; Nemoto et al., 2005, *J Neurol Neurosurg Psychiatry;* 76(5):714-8; Shiraishi et al., 2005, *Ann Neurol;* 57(2):289-93; Vincent et al., 2005, *Neurology;* 64(2):399; Vincent and Rothwell, 2004, *Autoimmunity;* 37(4):317-9; Vincent et al., 2004, *Semin Neurol;* 24(1):125-33; Zhou et al., 2004, *Muscle Nerve;* 30(1):55-60; McConville et al., 2004, *Ann Neurol;* 55(4):580-4; Vincent et al., 2003, *Ann NY Acad Sci;* 998:324-35; Vincent et al., 2003, *Lancet Neurol;* 2(2):99-106; Sanders et al., 2003, *Neurology;* 60(12):1978-80; McConville and Vincent, 2002, *Curr Opin Pharmacol;* 2(3):296-301; Liyanage et al., 2002, *Muscle Nerve;* 25(1):4-16; and Hoch et al., 2001, *Nat Med;* 7(3):365-8.

Although a number of studies have documented that AChR or MuSK antibodies cause structural and functional damage to the NMJ of MG patients, the identity of autoantigen(s) in the more than 10% of MG patients without such antibodies to AChR or MuSK remain unknown. The present invention demonstrates that a subset of AchR/MuSK-antibody-seronegative MG patients have serum autoantibodies against LRP4. The LRP4 antibodies were specific for the extracellular domains of LRP4 expressed in transfected HEK293 cells and strongly inhibited LRP4 function in cultured myotubes, indicating involvement of LRP4 antibodies in the pathogenesis of AchR/MuSK-antibodies-seronegative MG and defining a novel immunological form of the disease. Measurement of LRP4 antibodies will aid diagnosis and clinical management in MG patients.

The present invention also includes model systems for seronegative myasthenia gravis. Such model systems include a non-human mammal immunized with low density lipoprotein receptor-related protein 4 (LRP4), or an antigenic fragment thereof. Such model systems include a non-human mammal passively immunized with antibodies with a specificity for the low density lipoprotein receptor-related protein 4 (LRP4), or an antigenic fragment thereof. Such antibodies include, but are not limited to, those found in a bodily fluid of a subject, such as a serum or cerebrospinal sample, an isolated or purified autoantibody, a polyclonal antibody, or a monoclonal, antibody. Such a bodily fluid may be from a seronegative myasthenia gravis subject, wherein a seronegative myasthenia gravis subject is seronegative for autoantibodies to the acetylcholine receptor (AChR) and/or muscle specific tyrosine kinase (MuSK). A non-human mammal includes, but is no limited to mice, rats, and non-human primates.

The present invention includes methods for diagnosing neurotransmission or developmental disorders by detecting a genetic mutation in one or more alleles of the low density lipoprotein receptor-related protein 4 (LRP4) gene. A genetic mutation includes, but is not limited to, an intronic mutation, an exonic mutation, a mutation in a coding sequence, a mutation in a regulatory sequence, a splice junction mutation, a point mutation, a missense mutation, an insertion mutation, a deletion mutation, an insertion-deletion mutation, a mutation altering one or more amino acids, a read through mutation, a frameshift mutation, a mutation affecting mRNA splicing, a mutation introducing a stop codon, a mutation affecting mRNA half life, a mutation affecting mRNA transcription, a mutation affecting mRNA translation, a mutation reducing LRP4 mRNA and/or protein expression, and a mutation preventing LRP4 mRNA and/or protein expression. The present invention includes assay kits that include one or more polynucleotide sequences for identifying such mutations. Such mutations may be identified using LRP4 genomic or RNA sequences, or primers derived from such sequences in methods including, but not limited to, those described in Engel et al., 2009, *J Mol Neurosci;* 40(1-2):143-53; Selcen et al., 2008, *Ann Neurol;* 64(1):71-87; Shen et al., 2008, *J Clin Invest;* 118(5):1867-76; Di Castro et al., 2007, *J Physiol;* 579(Pt 3):671-7; and Ohno and Engel, 2005, *Acta Myol;* 24(2):50-4.

The present invention includes compositions with one or more of the antibodies and/or compounds described herein. A composition may also include, for example, buffering agents to help to maintain the pH in an acceptable range or preservatives to retard microbial growth. Such compositions may also include a pharmaceutically acceptable carrier. As used herein, the term "pharmaceutically acceptable carrier" refers to one or more compatible solid or liquid filler, diluents or encapsulating substances which are suitable for administration to a human or other vertebrate animal. The compositions of the present invention are formulated in pharmaceutical preparations in a variety of forms adapted to the chosen route of administration. Such compositions may be administered in an effective amount to a subject for the treatment of a neurotransmission or developmental disorder.

The present invention also includes pharmaceutically acceptable salts of inhibitors. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods.

The agents of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical, or injection into or around the tumor.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants.

Therapeutically effective concentrations and amounts may be determined for each application herein empirically by testing the compounds in known in vitro and in vivo systems, such as those described herein, dosages for humans or other animals may then be extrapolated therefrom. The efficacy of the administration of one or more agents may be assessed by any of a variety of parameters well known in the art.

In some therapeutic embodiments, an "effective amount" of an agent is an amount that results in a reduction of at least one pathological parameter. Thus, for example, in some aspects of the present invention, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

An agent or antibody of the present invention may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

As used herein, the term "subject" includes, but is not limited to, humans and non-human vertebrates. In preferred embodiments, a subject is a mammal, particularly a human. A subject may be an individual. A subject may be a patient. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

The methods of the present invention include in vivo and in vitro methods. As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The present invention is illustrated by the following examples. It is to be understood that the particular examples, materials, amounts, and procedures are to be interpreted broadly in accordance with the scope and spirit of the invention as set forth herein.

Example 1

LRP4 Serves as a Co-Receptor of Agrin

Formation of the neuromuscular junction (MJ) requires agrin, a factor released from motoneurons, and MuSK, a transmembrane tyrosine kinase that is activated by agrin. However, how signal is transduced from agrin to MuSK remains unclear. This example demonstrates that LRP4, a low-density lipoprotein receptor (LDLR)-related protein functions as a co-receptor of agrin. LRP4 is specifically expressed in myotubes and is concentrated at the NMJ. The extracellular domain of LRP4 interacts with neuronal, but not muscle, agrin. Expression of LRP4 enables agrin binding activity and MuSK signaling in cells that otherwise does not respond to agrin. Suppression of LRP4 expression attenuates agrin binding activity, agrin-induced MuSK tyrosine phosphorylation and AChR clustering in muscle cells. LRP4 also interacts with MuSK in a manner that is stimulated by agrin. Finally, this example showed that LRP4 becomes tyrosine-phosphorylated in agrin-stimulated muscle cells. These observations identify LRP4 as a functional co-receptor of agrin that is necessary for agrin-induced MuSK signaling and AChR clustering.
Experimental Procedures Reagents and antibodies. Taq DNA polymerase, T4 DNA ligase, and restriction enzymes were purchased from Promega. Horseradish peroxidase conjugated goat anti-mouse and goat anti-rabbit antibodies and enhanced chemifluoresent (ECL) reagents for Western blotting were from Amersham. Rhodamine-aBTX (R-BTX) was from Molecular Probes. Oligonucleotides were synthesized by Operon Biotechnologies. Unless otherwise specified, all chemicals were from Sigma-Aldrich. Antibodies were purchased from Sigma (Flag M2, F3165); Torrey Pines Biolabs (GFP, TP401); Upstate Biotechnology (4G10, 05-1050); Cell Signaling (Phospho-c-Abl, 2861); Novus (β-actin, NB600-501). Rabbit anti-MuSK antibodies were described previously (Luo et al., 2002, Neuron; 35:489-505). Rabbit anti-LRP4 antibody was described previously (Lu et al., 2007, Brain Res; 1177:19-28). Rat anti-AChR α-subunit antibody was mAb35 and rat anti-AChR β-subunit antibody was mAb124.

Constructs. Agrin-AP constructs were generated by fusing neuronal and muscle agrin (aa 1145-1940) (Ferns et al., 1993, Neuron (USA); 11:491-502) with AP in pAPtag-5. To generate Flag-MuSK, the MuSK DNA was generated by PCR and subcloned in EcoRI/XbaI sites in pFlag-CMV1 downstream of an artificial signal peptide sequence and a Flag epitope. LRP4-Myc was generated by subcloning the full length LRP4 DNA into NheI and HindIIIa sites in pcDNA3.1-MycHis (Invitrogen) with 3 alanine insert after amino acid 1746. LRP4N-Myc was generated by subcloning LRP4 extracellular domain DNA into NheI and NotI sites in pcDNA3.1-MycHis. LRP5 DNA was amplified with pCMV-Sports6-LRP5 (Open Biosystems) as template and subcloned into XbaI and NotI sites in pcDNA3.1-MycHis to generate LRP5-Myc. LRP4-, LRP5- and MuSK-miRNA constructs were generated using the BLOCK-iT Pol II miR RNAi Expression Vector Kit (Invitrogene, K4936-00). Oligonucleotide sequences for miRNA constructs were as follows:

```
For mi-MuSK-1161:
                                          (SEQ ID NO: 1)
5'-TGCTG TAACA CAGCA GAGCC TCAGC AGTTT TGGCC

ACTGA CTGAC TGCTG AGGCT GCTGT GTTA-3' (sense)
and
                                          (SEQ ID NO: 2)
5'-CTGTA ACACA GCAGC CTCAG CAGTC AGTCA GTGGC CAAAA CTGCT GAGGC TCTGC TGTGT TAC-3' (antisense);

For mi-LRP5-1490:
                                          (SEQ ID NO: 3)
5'-TGCTG ATCAC AGGGT GCAAC ACAAT GGTTT TGGCC

ACTGA CTGAC CATTG TGTCA CCCTG TGAT-3' (sense)
and
                                          (SEQ ID NO: 4)
5'-CCTGA TCACA GGGTG ACACA ATGGT CAGTC AGTGG CCAAA ACCAT TGTGT TGCAC CCTGT GATC-3' (antisense);

For mi-LRP4-1062:
                                          (SEQ ID NO: 5)
5'-TGCTG TTAAC ATTGC AGTTC TCCTC AGTTT TGGCC ACTGA

CTGAC TGAGG AGATG CAATG TTAA-3' (sense)
and
                                          (SEQ ID NO: 6)
5'-CCTGT TAACA TTGCA TCTCC TCAGT CAGTC AGTGG CCAAA ACTGA GGAGA ACTGC AATGT TAAC-3' (antisense);

For mi-LRP4-2603:
                                          (SEQ ID NO: 7)
5'-TGCTG AATAC ATGTA CCCGC CCATG GGTTT TGGCC ACTGA

CTGAC CCATG GGCGT ACATG TATT-3'(sense)
and
                                          (SEQ ID NO: 8)
5'-CCTGA ATACA TGTAC GCCCA TGGGT CAGTC AGTGG CCAAA ACCCA TGGGC GGGTA CATGT ATTC-3' (antisense);

For mi-LRP4-5355:
                                          (SEQ ID NO: 9)
5'-GCTGT AGCAC AGCTG ATTAT ACACG GTTTT GGCCA CTGAC

TGACC GTGTA TACAG CTGTG CTA-3'(sense)
and
                                          (SEQ ID NO: 10)
5'-CCTGT AGCAC AGCTG TATAC ACGGT CAGTC AGTGG CCAAA ACCGT GTATA ATCAG CTGTG CTAC-3' (antisense).
```

The authenticity of all constructs was verified by DNA sequencing. The following constructs were described previously: MuSK-AP (Wang et al., 2008, Neurosignals; 16:246-253); pcDNA-LRP4 (Lu et al., 2007, Brain Res; 1177:19-28);

Wnt1-HA (Zhang et al., 2007, *J Neurosci;* 27:3968-3973); and Wnt1-Myc, LRP6—N-Myc, and mfz8CRD-IgG (Tamai et al., 2000, *Nature;* 407:530-535).

Cell culture and transfection. HEK293 cells and mouse C2C12 muscle cells were maintained and transfected as previously described (Zhang et al., 2007, JNeurosci; 27:3968-3973). In some experiments, myotubes were transfected with lipofectamine 2000 (Invitrogen, 11668-019). The cells were incubated with a mixture of DNA, lipofectamine and serum-free medium for 8 hours before being switched to the fusion medium. The DNA:lipofectamine ratio in the mixture was 1 µg:2 µl. The optimal volume of the mixture for 24-well dishes was 200 µl per well with 2 µg plasmid DNA.

Recombinant protein production and purification. To produce recombinant proteins, HEK293 were transfected with respective plasmids. Twenty-four hours after transfection, cells were switched to Dulbecco's Modified Eagle Medium supplemented with reduced concentration (0.05%) of fetal bovine serum, and secreted proteins were harvested 24 hr later. nAgrin-AP, mAgrin-AP, or MuSK-AP recombinant proteins, which contained 6-His-tags that were encoded by pAPtag-5, were purified by affinity chromatography using TALON Resins (BD Biosciences).

Solution binding assay. Flag-nAgrin was immobilized to protein A Sepharose beads (that were preabsorbed with anti-Flag antibody), which were incubated with 1 ml (0.5 nM) of LRP4N-Myc, MuSKect-Myc, or LRP6N-Myc condition medium, and Flag-nAgrin-bound proteins were isolated by bead precipitation and resolved by SDS-PAGE and visualized by immunoblot with anti-Myc antibody. In some experiments, LRP4N-Myc, LRP6N-Myc or MuSKect-Myc was incubated with Wnt-1-HA immobilized on beads. LRP4 and LRP6 that were co-precipitated with Wnt-1 were analyzed by immunoblot with anti-Myc antibody.

Solid phase binding assay. Maxi-Sorp Immuno Plates (Nunc) were coated with purified LRP4-Myc at 4° C. overnight, and then incubated with 1% BSA in PBS to block non-specific binding. Coated wells were incubated with purified AP fusion proteins and the AP activity was measured using pNPP as substrate.

Intact cell binding assays. Live C2C12 myoblasts or myotubes in 15-mm dishes were incubated at room temperature for 90 min with 500 µl of 5 nM nAgrin-AP, mAgrin-AP or AP. Cells were washed three times with the HASH buffer (0.5 mg/ml bovine serum albumin, 0.1% NaN$_3$, 20 mM HEPES, pH 7.0 in Hank's balanced salt solution) and fixed in 60% acetone, 3% formaldehyde in 20 mM HEPES (pH 7.0) for 15 sec. Fixed cells were washed once in 20 mM HEPES (pH 7.0), 150 mM NaCl, incubated at 65° C. for 100 mM to inactivate endogenous AP, washed again in the AP buffer (0.1 M Tris-HCl, pH 9.4/0.1 M NaCl/5 mM MgCl2) and stained at room temperature overnight with 5-bromo-4-chloro-3-indolyl-phosphate (BCIP) (165 µg/ml)/nitroblue tetrazolium (NBT) (330 µg/ml) in the AP buffer. Digital photographs of stained cells were analyzed by using the NIH ImageJ software. In some experiments, Agrin-AP-bound cells were lyzed in the lysis buffer (1% Triton-X100, 10 mM Tris, pH 8.0). After the inactivation of the endogenous AP, lysates were assayed for AP activity using p-nitrophenyl phosphate (pNPP) as substrate.

Immunoprecipitation, immunoblotting, and AChR clustering assays. These assays were performed as previously described (Luo et al., 2002, *Neuron;* 35:489-505; Zhang et al., 2007, *J Neurosci;* 27:3968-3973; Zhu et al., 2008, *J Neurosci;* 28:1688-1696). Unless otherwise indicated, the final concentration of recombinant neuronal agrin was 1 nM to stimulate muscle cells. Band intensity of immunoblot was analyzed by using the ImageJ software.

Statistical Analysis. Data of multiple groups was analyzed by ANOVA, followed by a student-Newman-Keuls test. Two-tailed Student's t test was used to compare data between two groups. Differences were considered significant at $P<0.05$. Values and error bars in figures denote mean±SEM.

Results

LRP4 is expressed specifically in myotubes and concentrated at the NMJ Because neuronal agrin binds only to myotubes, but not myoblasts (Glass et al., 1996, *Cold Spring Harb Symp Quant Biol;* 61:435-444), the expression of LRP4 in developing myotubes was characterized. C2C12 myoblasts were switched fusion medium to induce muscle differentiation. Under these conditions, myotubes began to form 48 hr after medium switch (Luo et al., 2002, *Neuron;* 35:489-505; Luo et al., 2003, *Neuron;* 40:703-717; Si et al., 1996, *J Biol Chem;* 271:19752-19759). Developing myotubes were collected and LRP4 expressed analyzed by immunoblotting with anti-LRP4 antibody. As shown in FIG. 1A, LRP4 was barely detectable in myoblasts, but its expression gradually increased as myotubes matured.

As control, expression of MuSK was examined in same preparations, whose expression was known to be regulated by muscle differentiation (Glass et al., 1996, *Cell;* 85:513-523; Ip et al., 2000, *Mol Cell Neurosci;* 16:661-673; Valenzuela et al., 1995, *Neuron (USA);* 15:573-584) (FIG. 1A). These results indicate that LRP4, like MuSK, is expressed in well differentiated myotubes, but not myoblasts. Next, LRP4 distribution in vivo was investigated by staining muscle sections with anti-LRP4 antibody. The immunoreactivity of LRP4, as well as MuSK, showed a pattern of labeling similar to that of rhodamine-conjugated a-bungarotoxin (R-BTX) that labels AChRs (FIG. 1B), suggesting that LRP4, like MuSK, is enriched at the NMJ. This notion was supported by results from immunoblot analysis of LRP4 expression of muscles. Hemi-diaphragms were divided into three regions: the central, narrow region, where NMJs are enriched, as synaptic region; the region close to ligaments to the ribs as non-synaptic region; and the middle in between. The AChR was enriched in the synaptic, but not non-synaptic, region (FIG. 1C). In agreement with results of immunostaining, LRP4 was readily detectable in the synaptic region where AChRs were enriched. However, little, if any, LRP4 was found in the non-synaptic region. Together these results demonstrated that LRP4 is specifically expression in myotubes and is enriched at the NMJ, suggesting a role of LRP4 in NMJ formation.

The LRP4 extracellular domain binds to neuronal agrin. Next, it was determined whether agrin binds to LRP4. A secreted form of neuronal agrin, Flag-nAgrin, was generated that comprised the C-terminus of neuronal agrin fused with the Flag epitope, and a secreted form of LRP4 (i.e., LRP4N-Myc), which consisted of the LRP4 extracellular domain tagged by the Myc epitope. Flag-nAgrin was immobilized on beads and incubated with LRP4N-Myc. As shown in FIG. 2A, LRP4N-Myc was precipitated with neuronal agrin, suggesting that the two proteins interact in solution.

Figure 8:
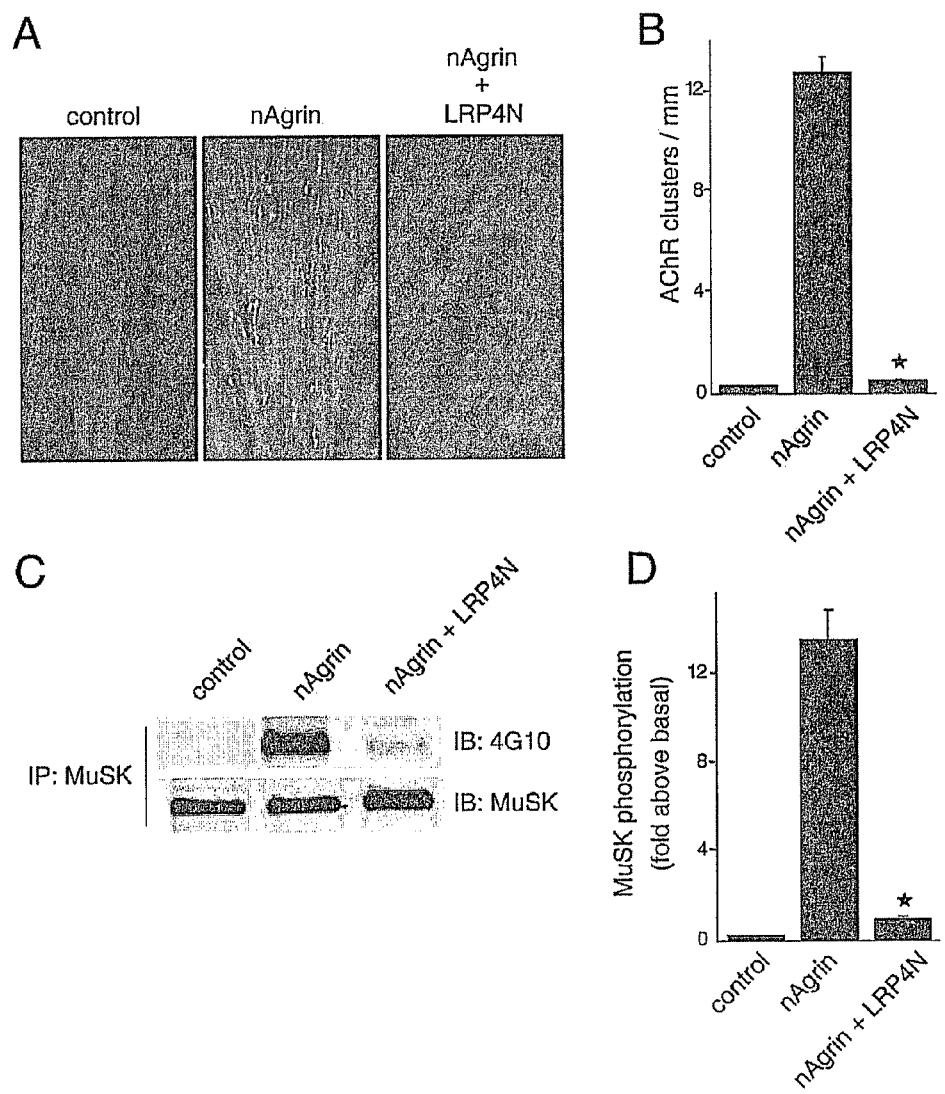
FIG. 8. Attenuation of agrin function by LRP4 extracellular domain.

In contrast, Flag-nAgrin did not precipitate MuSKect-Myc, which consisted of the extracellular region of the kinase (FIG. 2B), in agreement with previous findings that agrin and MuSK do not directly bind to each other (Glass et al., 1996, *Cold Spring Harb Symp Quant Biol;* 61:435-444). Moreover, Flag-nAgrin did not interact with LRP6N-Myc, which comprised Myc-tagged extracellular domain of LRP6, a homologous member of the LRP family whose extracellular structural organization resembles that of LRP4 (FIG. 2C). As control, LRP6N-Myc was able to interact with Wnt-1-HA when the two proteins were incubated together (FIG. 2D), indicating proper folding and specific binding of LRP6N-Myc. Furthermore, LRP4N-Myc did not co-precipitate with Wnt-1-HA (FIG. 2E), suggesting that the two proteins do not interact. These results demonstrate that agrin binds specifically to the extracellular domain of LRP4, but not that of MuSK, or LRP6 and on the other hand, Wnt-1 interacts with LRP6, but not LRP4. In support of this notion, the extracellular domain of LRP4 was able to neutralize neuronal agrin and thus prevented it from stimulating MuSK tyrosine phosphorylation and AChR clustering (FIG. 8).

To determine whether the interaction is direct, the recombinant agrins nAgrin-AP and mAgrin-AP were produced, which contained the C-terminal region of neuronal and muscle agrin, respectively. They were fused with the heat-insensitive human placental isozyme of alkaline phosphatase (AP) (Flanagan et al., 2000, *Methods Enzymol;* 327:198-210) (FIG. 3A). The activity of the AP recombinant proteins was tested in AChR cluster assays. As shown in FIG. 3B, nAgrin-AP was able to stimulate AChR clustering in C2C12 myotubes, indicating proper folding of the recombinant neuronal agrin protein. In contrast, mAgrin-AP or AP alone had little effect on AChR clustering.

Next, the binding activity of the AP proteins to muscle cells was characterized by in-cell assays, as described in Experimental Procedures. AP binding to myoblasts or myotubes was minimal (FIG. 3C). mAgrin-AP binding to myoblasts was higher than that of AP alone, presumably because myoblasts express alpha-dystroglycan to which muscle agrin is known to interact (Bowe et al., 1994, *Neuron (USA);* 12:1173-1180; Campanelli et al., 1996, *Development;* 122:1663-1672; Campanelli et al., 1994, *Cell;* 77:663-674; Gee et al., 1994, *Cell;* 77:675-686; Gesemann et al., 1996, *Neuron (USA);* 16:755-767; Hopf and Hoch, 1996, *J Biol Chem;* 271:5231-5236; Sugiyama et al., 1994, *Neuron (USA);* 13:103-115). The mAgrin-AP binding to myotubes was higher in comparison with that in myoblasts because alpha-dystroglycan expression was increased during muscle differentiation. nAgrin-AP binding to myoblasts was similar to that of mAgrin-AP (FIG. 3C). However, nAgrin-AP binding was significantly higher in myotubes than in myoblasts (FIG. 3C), in agreement with earlier reports (Glass et al., 1996, *Cell;* 85:513-523) and the LRP4 expression pattern in developing muscle cells (FIG. 1).

These results demonstrate differential ability of recombinant muscle and neuronal agrins in binding to myotubes. Having established that nAgrin-AP was able to bind to myotubes and stimulate AChR clustering, the interaction between LRP4 and nAgrin-AP was characterized. LRPN4-Myc was purified and immobilized on plates and incubated with purified nAgrin-AP. After wash, the AP activity bound to immobilized LRPN4-Myc was assayed by a modified ELISA (enzyme-linked immunosorbent assay). In comparison with control (AP alone), there was a significant increase in AP activity when nAgrin-AP were incubated with LRP4N-Myc (FIG. 3D), suggesting direct interaction between the two proteins, i.e., independent of a third protein. Quantitatively, the interaction between neuronal agrin and LRP4 was dose-dependent, saturable, and of high affinity (Kd values of 0.5±0.053 nM) (FIGS. 3E and 3F). This affinity is comparable to that (0.1-0.5 nM) of LRP6 for Dkk1 and Dkk2 (Bafico et al., 2001, *Nat Cell Biol;* 3:683-686; Mao et al., 2001, *Nature;* 411:321-325; Semenov et al., 2001, *Curr Biol;* 11:951-961). In contrast, muscle agrin, which lacks four and eight amino acid inserts at the Y and Z sites, respectively (FIG. 3A) and is 1000 times less potent than neuronal agrin in stimulating AChR clusters (Gesemann et al., 1995, *J Cell Biol;* 128:625-636; Reist et al., 1992, *Neuron (USA);* 8:865-868), did not appear to bind to LRP4 (FIG. 3D). The binding of LRP4N-Myc to muscle agrin was minimal even at high concentrations (FIG. 3E). Together, these results suggest LRP4 binds specifically to neuronal agrin with high affinity. These results indicate that LRP4 binds to neuronal, but not muscle, agrin in a manner that is concentration-dependent, saturable and of high affinity.

Reconstitution of neuronal agrin binding and signaling in transfected cells. To determine whether agrin binds to LRP4 in vivo, exogenous LRP4 was expressed in C2C12 myoblasts that, unlike myotubes, do not bind neuronal agrin (Glass et al., 1996, *Cell;* 85:513-523) (FIG. 3C). Myoblasts were transfected with full length LRP4 or the empty vector (as control). Intact transfected myoblasts were incubated with AP alone, nAgrin-AP or mAgrin-AP. The AP activity bound to cell surface was measured in situ after heat inactivation of endogenous AP. As shown in FIGS. 4A and 4B, when incubated with AP alone, control and LRP4-transfected myoblasts show no difference in AP activity. However, nAgrin-AP binding was significantly higher to LRP4-transfected myoblasts in comparison with control, indicating that LRP4 enables myoblasts to interact with neuronal agrin. By contrast, transfection of MuSK had no consistent effect on binding to nAgrin-AP, in agreement with earlier observations that agrin does not bind to MuSK (Glass et al., 1996, *Cell;* 85:513-523) (FIG. 2B). In addition to myoblasts, HEK293 cells were able to bind to nAgrin-AP after LRP4 transfection (FIG. 4C).

The in situ binding activity generated by transfected LRP4 had the following characters. First, it was dose-dependent. Increase in LRP4 expression in transfected HEK293 cells led to higher nAgrin-AP binding activity (FIG. 4C). Probably due to rate-limiting surface integration of overexpressed LRP4, nAgrin-AP binding was not further increased in cells transfected with 2 μg of DNA. Earlier studies have reported that overexpressed LRP4 is retained in the endoplasmic reticulum (Lu et al., 2007, *Brain Res;* 1177:19-28; Obermoeller-McCormick et al., 2001, *J Cell Sci;* 114:899-908). Notice that the blot reveals total, but not surface, LRP4 (FIG. 4C). Second, LRP4 binding was specific for neuronal agrin because the amount of mAgrin-AP bound to transfected myoblasts and HEK293 cells was minimal, and not concentration-dependent (FIGS. 4A to 4C). Notice that mAgrin-AP, like nAgrin-AP, also contained the AP and the Myc and His tags. Inability of mAgrin-AP to bind to LRP4-transfected cells indicate that binding to LRP4 does not involve the AP or tags. Third, the binding activity was LRP4 specific. Expression of LRP5, another member of the LRP family (Herz and Bock, 2002, *Ann Rev Biochem;* 71:405-434), did not increase agrin binding in transfected cells (FIG. 4D). Last, nAgrin-AP binding was similar between cells transfected with LRP4 alone and those co-transfected with LRP4 and MuSK (FIGS. 4A and 4B), indicating that the neuronal agrin binding activity is mainly contributed by LRP4 although LRP4 and MuSK could interact in muscle cells (see below). Taken together, these results demonstrate the ability of LRP4 to reconstitute agrin binding in cells that otherwise do not interact with agrin.

Next, it was determined if LRP4 was able to reconstitute MuSK signaling in cells that do not respond to agrin. MuSK is a receptor tyrosine kinase whose activation has been shown to be upstream of all known agrin signaling cascades (Fuhrer et al., 1997, *Embo J;* 16:4951-4960; Glass et al., 1997, *Proc Natl Acad Sci USA;* 94:8848-8853; Glass et al., 1996, *Cell;* 85:513-523; Herbst and Burden, 2000, *Embo J;* 19:67-77; Luo et al., 2002, *Neuron;* 35:489-505; Strochlic et al., 2005, *Bioessays;* 27:1129-1135; Wang et al., 2008, *Neurosignals;* 16:246-253; Zhou et al., 1999, *J Cell Biol;* 146:1133-1146).

Therefore we first examined whether LRP4 expression enables MuSK activation by agrin in HEK293 cells that do not express LRP4 (FIG. 4E). Flag-MuSK was transfected into HEK293 cells with or without LRP4 and transfected cells were stimulated with neuronal agrin. As shown in FIGS. 4E and 4G, agrin was unable to elicit MuSK tyrosine phosphorylation in HEK293 cells transfected with MuSK alone. Intriguingly, LRP4 co-expression enabled agrin to activate MuSK, indicating that LRP4 could be an agrin receptor able to stimulate MuSK. Basal tyrosine phosphorylation of MuSK, i.e., in the absence of agrin, was increased by LRP4, which could suggest a role of LRP4 in MuSK auto-activation, presumably by its direct interaction with the kinase (see below). Agrin-induced AChR clustering requires the intracellular tyrosine kinase Abl (Finn et al., 2003, *Nat Neurosci;* 6:717-723). To further investigate the role of LRP4, Abl activation was examined by anti-phospho-Abl antibody in cells co-expressing LRP4 and MuSK. As shown in FIGS. 4F and 4G, active Abl was barely detectable in cells transfected with Myc-MuSK alone, regardless of agrin stimulation. In contrast, agrin elicited a significant increase in phospho-Abl in cells co-expressing LRP4 and Myc-MuSK. Together, these results indicate that LRP4 expression enables binding activity for neuronal agrin, MuSK activation, and initiation of intracellular signaling in cells that otherwise do not respond to agrin. Decrease of LRP4 levels attenuates neuronal agrin binding, MuSK activation, and induced AChR clustering in muscle cells.

It was next determined if LRP4 is necessary for agrin/MuSK signaling by a loss-of-function approach. To this end, we generated several microRNA constructs of LRP4. As shown in FIG. 5A, miLRP4-1062 was most potent in inhibiting LRP4 expression. First, it was determined if repression of LRP4 affects agrin binding to intact muscle cells. C2C12 myoblasts were transfected with miLRP4-1062 or the control miRNA that encoded scramble sequence, and resulting myotubes were incubated with AP, mAgrin-AP or nAgrin-AP and assayed for AP activity by in-cell staining. In comparison with control miRNA, miLRP4-1062 did not appear to alter binding activity of AP and mAgrin-AP to myotubes (FIGS. 5B and 5C). However, myotubes transfected with miLRP4-1062 had lower levels of nAgrin-AP staining in comparison with those transfected with the control vector (FIGS. 5B and 5C), indicating a necessary role of endogenous LRP4 for neuronal agrin binding. Second, it was tested whether LRP4 is required for agrin to stimulate tyrosine phosphorylation of MuSK. MuSK was precipitated from myotubes transfected with control mmRNA or miLRP4-1062 and assayed for tyrosine phosphorylation. Expression of miRNA constructs was indicated by the presence of GFP that was encoded by the parental vector. As shown in FIG. 5D, transfection of miLRP4-1062 reduced expression of endogenous LRP4, but not MuSK or β-actin. Remarkably, agrin-induced MuSK tyrosine phosphorylation was attenuated in myotubes transfected with miLRP4-1062 in comparison with control miRNA (FIG. 5E). These results suggest that MuSK activation is impaired when LRP4 levels were reduced.

Finally, whether LRP4 is necessary for agrin-induced AChR clustering was investigated. Myoblasts were transfected with control miRNA or miLRP4-1062, or miRNA constructs against MuSK and LRP5 that reduced expression of MuSK and LRP5, respectively. Transfected myotubes were stimulated without or with agrin and AChR clusters in GFP-expressing myotubes scored as described previously (Zhang et al., 2007, *J Neurosci;* 27:3968-3973). Expression of these miRNA constructs did not appear to alter basal AChR clusters. However, the number of agrin-induced AChR clusters was reduced in myotubes transfected with miLRP4-1062 (FIG. 5F), suggesting a necessary role of LRP4 in agrin-induced clustering. Similar reduction was observed in myotubes expressing miMuSK-1161, as expected. Transfection with miLRP5-1490, however, had no effect on agrin-induced AChR clustering, in agreement with the observation that LRP5 does not bind to neuronal agrin (FIG. 4D). Interaction between LRP4 and MuSK.

In a working model, LRP4 serves as a co-receptor that binds to agrin and, together with MuSK, stimulates AChR clustering. To examine the relationship among agrin, LRP4 and MuSK, it was determined whether LRP4 interacts with MuSK and if so, if the interaction is regulated by agrin. Secreted Flag-MuSKect, which comprised the entire extracellular region of MuSK fused with the Flag epitope, was incubated with LRP4N-Myc in the absence or presence of agrin. Flag-MuSKect alone was able to co-precipitate with LRP4N-Myc (FIGS. 6A and 6B), indicative of direct binding between the extracellular domains of MuSK and LRP4. Quantitatively, the interaction between MuSK and LRP4 was dose-dependent and saturable, and of high affinity (Kd values of 0.45±0.041 nM, FIGS. 6C and 6D). Interestingly, the amount of LRP4 co-precipitated with Flag-MuSKect was increased by agrin (FIGS. 6A and 6B). In contrast, as control, LRP6N-Myc failed to co-precipitate with Flag-MuSKect regardless of the presence or absence of agrin (FIG. 6E).

These observations suggest that LRP4 and MuSK form a complex in the absence of the ligand agrin; however, agrin, via binding to LRP4, enhances the LRP4-MuSK interaction. To test this hypothesis further, we examined if full length MuSK and LRP4 interact with each other in cells. LRP4 and Flag-MuSK were co-transfected into HEK293 cells. MuSK was precipitated from cell lysates by a Flag antibody and the resulting immunocomplex was analyzed for LRP4. As shown in FIG. 6F, LRP4 co-precipitated with MuSK in transfected cells, in support of the notion that the two proteins interact in transfected cells. Moreover, the LRP4-MuSK association was detectable in mouse muscle homogenates (FIG. 6G), suggesting in vivo interaction of the two proteins.

Neuronal agrin stimulates LRP4 interaction with MuSK and tyrosine phosphorylation. To further investigator the role of LRP4 in agrin signaling, whether the LRP4-MuSK interaction in muscle cells is regulated by neuronal agrin was examined. C2C12 myotubes were treated without or with agrin for one hour. Myotubes were subjected to immunoprecipitation with anti-LRP4 antibody and resulting precipitates were probed for MuSK. As shown in FIG. 7A, MuSK co-precipitated with LRP4 from cells in the absence of agrin, suggesting basal interaction of the two proteins and in agreement with in vitro binding results (FIG. 6A-D). The co-precipitation was increased in agrin-stimulated myotubes (FIGS. 7A and 7B). These observations indicate that LRP4 and MuSK form a complex in a manner that is up-regulated by agrin. LRP4 has a large intracellular domain containing six tyrosine residues.

Recent evidence indicates that LRP4, immunopurified from the brain, could be phosphorylated on serine residues presumably by CaMK II (Tian et al., 2006, *Eur J Neurosci;* 23:2864-2876). Other members of the LRP family, LRP5 and LRP6, become phosphorylated upon activation of the Wnt canonical pathway (Ding et al., 2008, *J Cell Biol;* 182:865-872). Unlike LRP5 and LRP6, LPR4 has a NPXY motif in the intracellular region that may be phosphorylated by a tyrosine kinase (Herz and Bock, 2002, *Ann Rev Biochem;* 71:405-434). Having demonstrated that LRP4 interacts with MuSK and the interaction is enhanced by agrin, we determined whether LRP4 itself becomes phosphorylated on tyrosine residues. C2C12 myotubes were stimulated with neuronal agrin for one hour and lysates were subjected immunoprecipitation of LRP4 and MuSK, respectively. Resulting precipitates were probed with the anti-phospho-tyrosine antibody 4G10. As shown in FIGS. 7C and 7D, LRP4 as well as MuSK became tyrosine-phosphorylated in agrin-stimulated myotubes. This result suggests a role of LRP4 in agrin signaling.

Discussion

Figure 2:
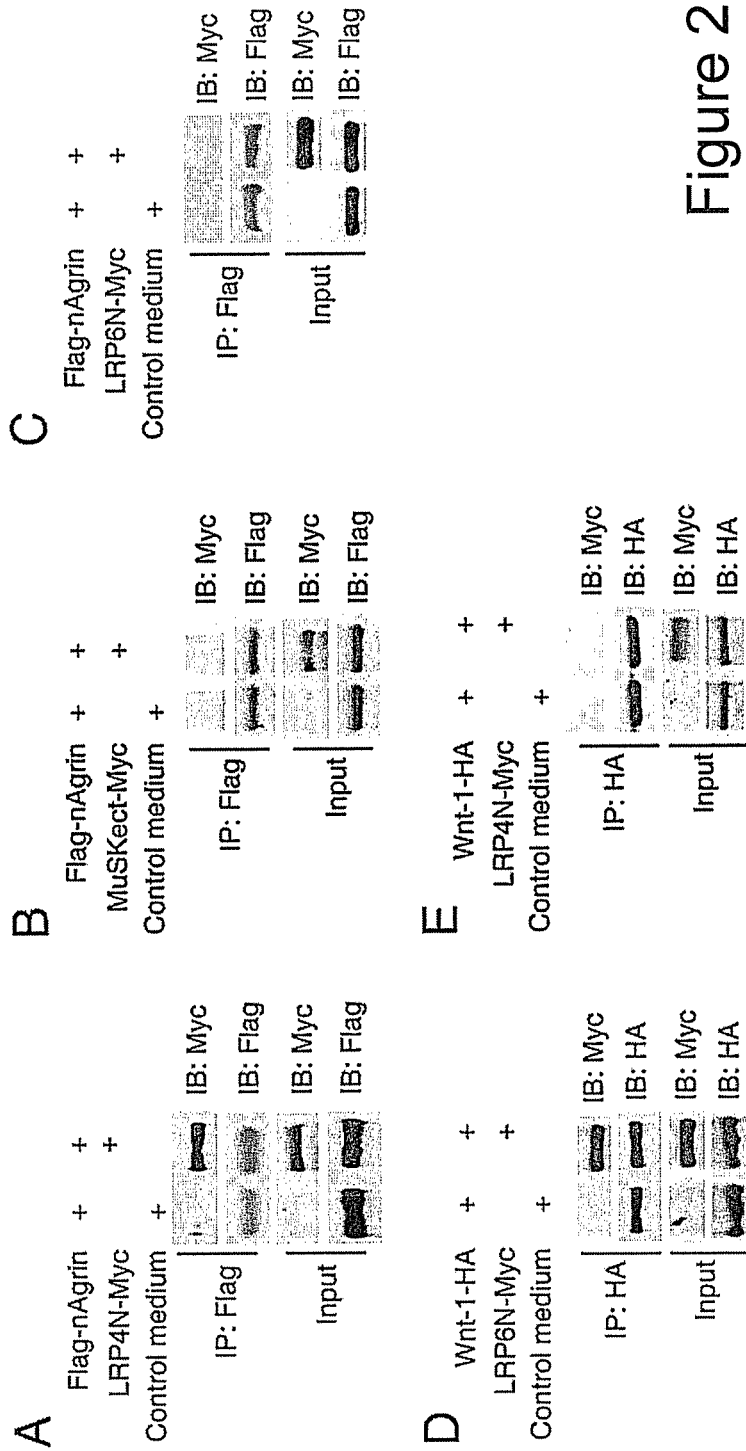
FIG. 2. The LRP4 extracellular domain interacts with neuronal agrin.
Figure 3:
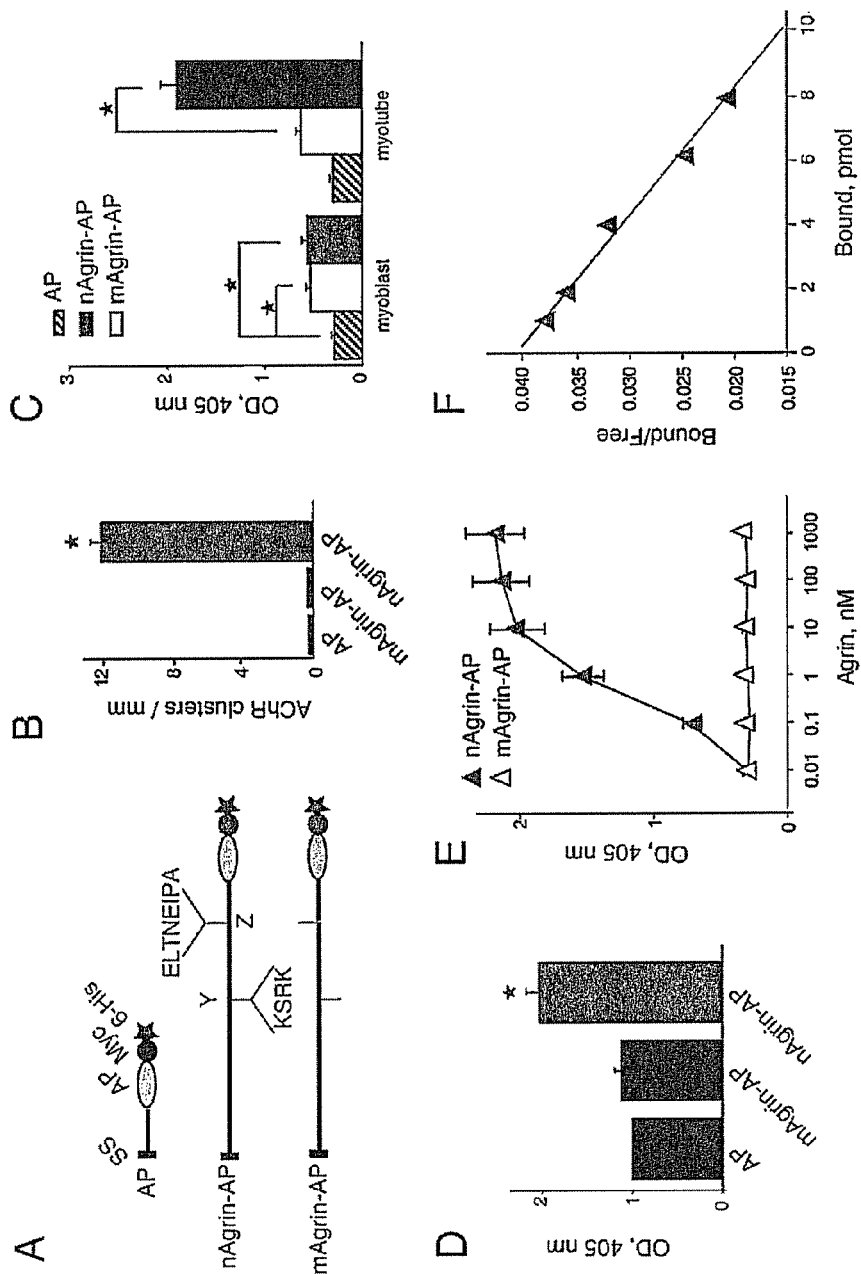
FIG. 3. High-affinity and specific interaction between of LRP4-neuronal agrin.
Figure 4:
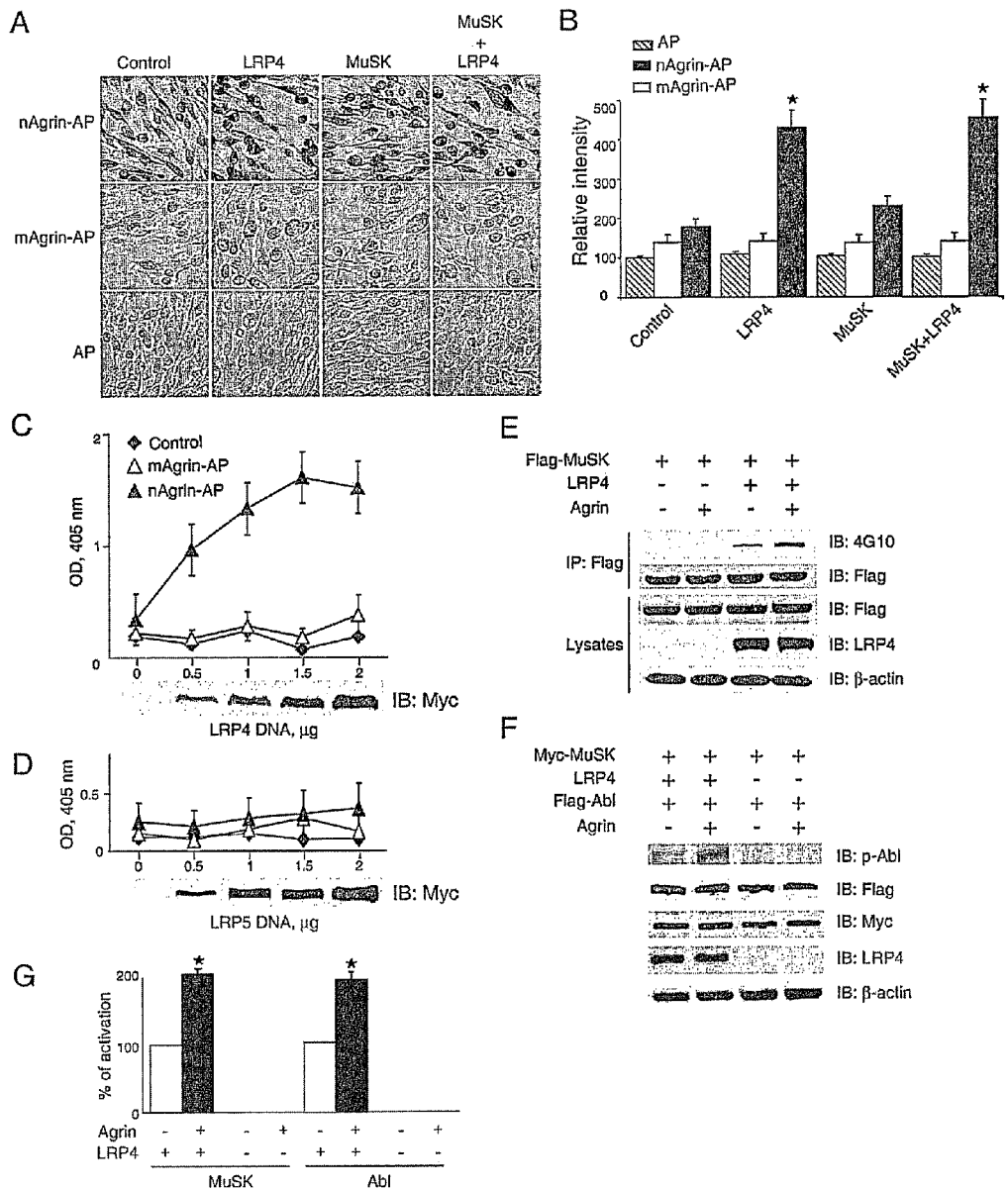
FIG. 4. Expression of LRP4 enables binding activity for neuronal agrin and MuSK signaling.
Figure 5:
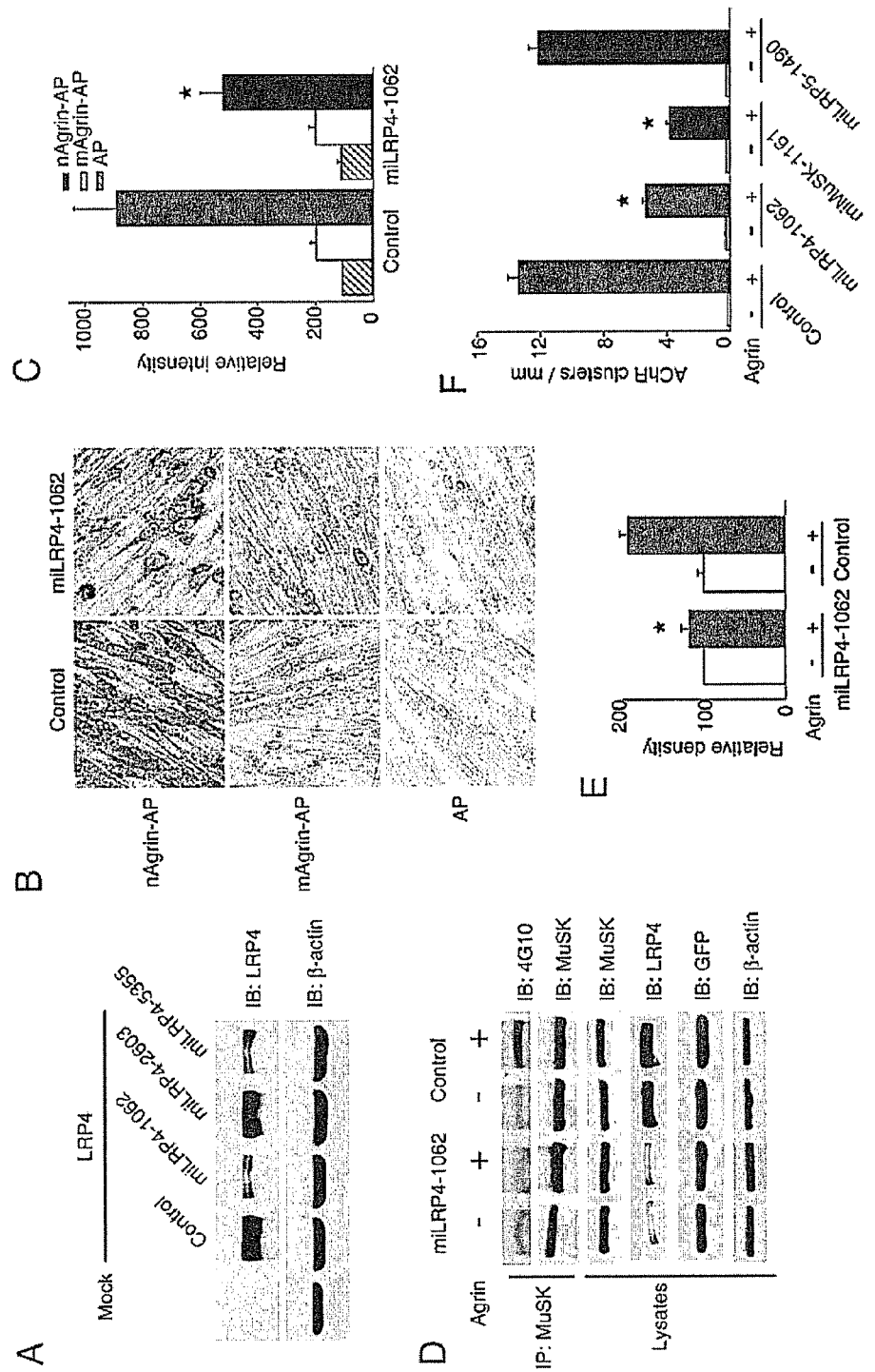
FIG. 5. Suppression of LRP4 expression attenuates neuronal agrin binding, MuSK activation, and induced AChR clustering.
Figure 6:
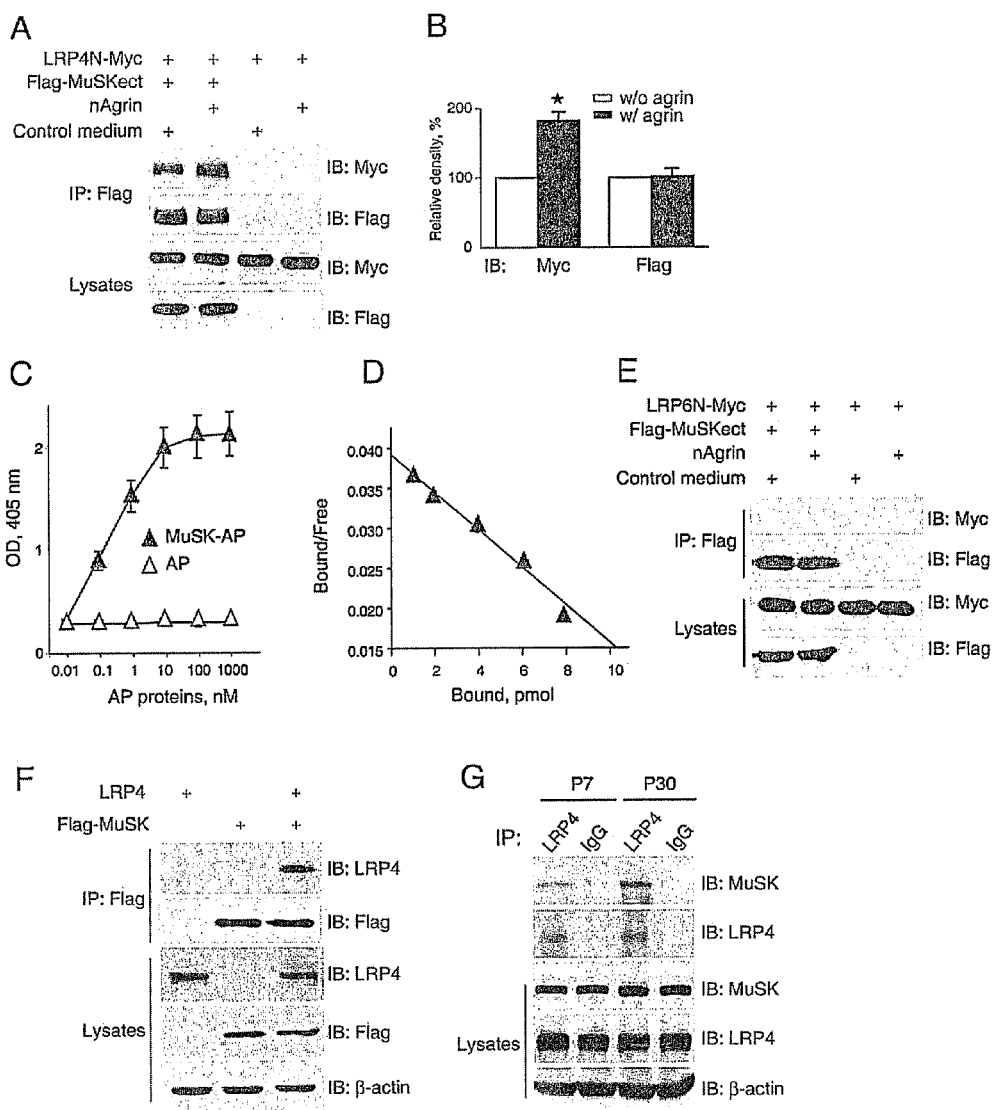
FIG. 6. Direct interaction between LRP4 and MuSK.

This example demonstrates the LRP4 is specifically expressed in myotubes, but not myoblasts and is concentrated at the NMJ (FIG. 1). Further, it is both necessary and sufficient to bind to agrin and to activate MuSK signaling that leads to AChR clustering. Using three different assays (in solution, on solid phase, and in cells), this example demonstrated that neuronal agrin was able to interact directly with the extracellular region of LRP4 (FIG. 2, FIG. 3, and FIG. 4). The binding activity of LRP4 was specific because 1) LRP4 binding to muscle agrin was minimal; 2) the binding is concentration-dependent and of high affinity with a sub-nanomolar Kd; and 3) neuronal agrin did not bind to LRP5 or LRP6, two other members of the LRP family that are highly homologous to LRP4. Further, expression of LRP4 enabled binding activity for neuronal agrin and MuSK signaling in cells that otherwise did not respond to agrin (FIG. 4). And, suppression of LRP4 expression attenuated agrin binding activity and agrin-induced MuSK phosphorylation and AChR clustering in muscle cells (FIG. 5). Further, LRP4 could interact with MuSK in a manner that is increased by agrin (FIG. 6 and FIG. 7). Finally, LRP4 became tyrosine-phosphorylated in muscle cells in response to agrin stimulation (FIG. 7). These observations indicate that LRP4 can bind to agrin and transmit signals to MuSK, suggesting that it may serve as a functional receptor for agrin.

These observations indicate that LRP4 interacts with MuSK at basal levels in the absence of the ligand. Upon agrin stimulation, the interaction was increased to activate MuSK and subsequent downstream signal cascades for AChR clustering (FIG. 7E). Despite the essential role of MuSK in NMJ formation, mechanisms of how it is activated and how it acts to control NMJ formation remain elusive. Recent studies have shed light on intracellular pathways downstream of MuSK. They are thought to involve the adapter protein Dok-7 (Okada et al., 2006, *Science*; 312:1802-1805), and several enzymes including Src-family kinase (Ferns et al., 1996, *J Cell Biol*; 132:937-944; Mittaud et al., 2001, *J Biol Chem*; 276:14505-14513; Mohamed et al., 2001, *J Neurosci*; 21:3806-3818; Qu and Huganir, 1994, *J Neurosci*; 14:6834-6841; Wallace, 1991, *Philos Trans R Soc Lond Biol*; 331:273-280), Abl (Finn et al., 2003, *Nat Neurosci*; 6:717-723), casein kinase 2 (Cheusova et al., 2006, *Genes Dev*; 20:1800-1816), geranylgeranyl transferase I (GGT) (Luo et al., 2003, *Neuron*; 40:703-717), GTPases of the Rho family (Weston et al., 2003, *J Biol Chem*; 278:6450-6455; Weston et al., 2000, *J Cell Biol*; 150:205-212), and Pak1, a serine/threonine kinase that is activated by Rho GTPases (Luo et al., 2002, *Neuron*; 35:489-505).

Although agrin is known to activate MuSK, the two proteins, however, do not interact directly. The MASC co-receptor was hypothesized that has to be myotubes specific and is able to transmit signal from agrin to MuSK (Glass et al., 1996, *Cell*; 85:513-523). Remarkably, LRP4 is a protein specifically expressed in myotubes, not in myoblasts (FIG. 1), fulfilling a requirement of MASC. Second, LRP4 is able to reconstitute agrin binding and MuSK signaling in cells that otherwise do not respond to agrin (FIG. 4). Third, LRP4 is required for agrin binding and induced MuSK signaling and AChR clustering in muscle cells (FIG. 5). Fourth, genetic studies have demonstrated that phenotypes of LRP4 mutant mice are similar to those in MuSK mutant (Weatherbee et al., 2006, *Development*; 133:4993-5000). LRP4 mutants die at birth with defects in both pre- and post-synaptic differentiation and in particular, the rapsyn-dependent scaffold fails to assemble in LRP4 mutants.

These results provide strong evidence that LRP4 satisfies essential criteria of serving a functional co-receptor of agrin. The identification of LRP4 as a co-receptor for agrin could provide insight into mechanisms of how agrin stimulation leads to AChR clustering. First, bridging agrin and MuSK, LRP4 could transmit signal to MuSK and thus activate intracellular cascades that have been identified, leading to AChR clustering. Second, LRP4 may regulate MuSK activity. MuSK and LRP4 co-precipitate in vitro and in muscle cells in the absence of agrin (FIG. 6 and FIG. 7), and tyrosine phosphorylation of MuSK is increased in cells co-expressing LRP4 (FIGS. 4E and 4G). These observations may suggest that LRP4 promotes MuSK auto-activation, presumably by regulating MuSK dimerization. Exactly how LRP4 regulates MuSK function and the stoichiometry of the LRP4-MuSK interaction warrant further investigation. Third and alternatively, LRP4 itself may function as a signal transducer. The juxtamembrane cytoplasmic region of LRP4 contains a NPXY motif. This motif in LDLR, LRP1 and LRP2 has been shown to serve as a docking site for cytoplasmic adaptor proteins through a phosphotyrosine binding (PTB) domain (Herz and Bock, 2002, *Ann Rev Biochem*; 71:405-434). Intriguingly, LRP4 becomes tyrosine phosphorylated upon agrin stimulation (FIGS. 7C and 7D).

It would be interesting to investigate whether tyrosine phosphorylation of LRP4 is necessary for agrin signaling and AChR clustering and whether phosphorylated LRP4 binds to PTB domain-containing proteins. One such protein is Dok7, which is essential for NMJ formation (Okada et al., 2006, *Science*; 312:1802-1805). Wnt signaling is implicated in synapse formation (Clani and Salinas, 2005, *Nat Rev Neurosci*; 6:351-362). Wnt-7a released from granule cells induces axon and growth cone remodeling in mossy fibers (Hall et al., 2000, *Cell*; 100:525-535). In *C. elegans*, Wnt signaling positions NMJs by inhibiting synaptogenesis (Klassen and Shen, 2007, *Cell*; 130:704-716). NMJ formation in *Drosophila* revives Wnt signaling (Mathew et al., 2005, *Science*; 310:1344-1347; Packard et al., 2002, *Cell*; 111:319-330). However, it remains unclear whether Wnt signaling regulates mammalian NMJ formation. Wnt ligands act by binding to the receptor complex of Frizzled and LRP5/6 (Cadigan and Liu, 2006, *J Cell Sci*; 119:395-402; He et al., 2004, *Development*; 131:1663-1677; Malbon and Wang, 2006, *Curr Top Dev Biol*; 72:153-166; Schulte and Bryja, 2007, *Trends Pharmacol Sci*; 28:518-525)

Subsequently, signal is believed to be transmitted to the adapter protein Dishevelled (Dvl), which interacts with Frizzled, to initiate intracellular canonical and non-canonical pathways. Intriguingly, MuSK, like Frizzled, interacts with both a LRP protein (i.e., LRP4) and Dvl (Luo et al., 2002, *Neuron*; 35:489-505). In addition, MuSK contains an extracellular CRD domain that is highly homologous to that in Frizzled that interacts with Wnt (Glass et al., 1996, *Cell*; 85:513-523; Valenzuela et al., 1995, *Neuron (USA)*; 15:573-584). Moreover, a number of Wnt signaling molecules including APC and β-catenin have been implicated in MuSK cascades (Li et al., 2008, *Nat Neurosci*; 11:262-268; Wang et al., 2003, *Nat Neurosci*; 6:1017-1018; Zhang et al., 2007, *J Neurosci*; 27:3968-3973). These observations raise a question whether the agrin-LRP4-MuSK signaling is regulated by a Wnt ligand that may interact with LRP4 and/or MuSK. This example showed that LRP4 does not bind Wnt-1 (FIG. 2E). This, however, does not exclude possible involvement of one of the 18 other Wnt proteins in mouse (Clevers, 2006, *Cell;* 127:469-480) (see the Wnt Homepage on the worldwide web at stanford.edu/~musse/wntwindow).

On the other hand, the "Wnt signaling" molecules (including Dvl, APC, and β-catenin) may simply function in a manner independent of Wnt signaling in mammalian NMJ formation. It is of interest to note that the phenotypes of MuSK and LRP4 mutant mice are more severe than those of agrin mutant. In LRP4 or MuSK mutants, but not agrin mutants, AChR clusters are absent when clusters begin to assemble at E13.5 and the rapsyn-dependent scaffold fails to assemble (Lin et al., 2001, *Nature;* 410:1057-1064; Weatherbee et al., 2006, *Development;* 133:4993-5000).

These observations could suggest the existence of a signaling pathway that requires MuSK and/or LRP4, but not agrin. This pathway may regulate the formation of aneuronal AChR clusters prior to the arrival of motoneuron terminals or assembly of rapsyn-dependent scaffold. It may be regulated by a ligand that could interact with MuSK and/or LRP4. In light of the above discussion, such ligand may be a Wnt protein. Agrin is expressed in the brain (Cohen et al., 1997, *Neuroscience;* 76:581-596; Mann and Kroger, 1996, *Mol Cell Neurosci;* 8:1-13; O'Connor et al., 1994, *J Neurosci;* 14:1141-1152). Suppression of its expression impairs dendritic development and synapse formation in cultured hippocampal neurons (Bose et al., 2000, *J Neurosci;* 20:9086-9095; Ferreira, 1999, *J Cell Sci;* 112(Pt 24):4729-4738). Agrin-deficient neurons appear to be resistant to excitotoxic injury and agrin heterozygous mice are less sensitive to kainic acid-induced seizure and mortality (Hilgenberg et al., 2002). Agrin is thought to bind to the a3 subunit of Na+/K+-ATPase in neurons and thus regulates their function (Hilgenberg et al., 2006, *Cell;* 125: 359-369). LRP4 expression is enriched in the brain and could interact with postsynaptic scaffold proteins including PSD-95 and SAP97 (Lu et al., 2007, *Brain Res;* 1177:19-28; Tian et al., 2006, *Eur J Neurosci;* 23:2864-2876; Weatherbee et al., 2006, *Development;* 133:4993-5000). The identification of LRP4 as a co-receptor of neuronal agrin may shed light on molecular mechanisms of how agrin and LRP4 work in the brain.

Example 1 has also published as "LRP4 serves as a coreceptor of agrin," Zhang B, Luo S, Wang Q, Suzuki T, Xiong WC, and Mei L, *Neuron.* 2008 Oct. 23; 60(2):285-97 published online with Oct. 22, 2008.

Example 2

Autoantibodies to LRP4 in Double Seronegative Myasthenia Gravis Patients

With this example, it was determined that patients with myasthenia gravis (MG) have serum antibodies to LRP4, a newly identified receptor for agrin essential for neuromuscular junction (NMJ) formation. Briefly, serum from patients with MG with known status of serum antibodies to acetylcholine receptor (AChR) and muscle specific kinase (MuSK) and from control subjects (normal individuals and individuals with other diseases) were tested for antibodies to LRP4. Sera with such antibodies were tested for ability to inhibit two different functions of LRP4 at the NMJ. 217 patients with MG, 74 patients with other neurological diseases or psychiatric diseases and 45 normal individuals. Anti-LRP4 antibodies were detected in 11 of 120 MG patients without detectable anti-AChR (AChR+) or anti-MuSK (MuSK+) antibodies (double seronegative) and in 1 of 36 AChR−/MuSK+ patients, but not in any of 61 AChR+ patients. None of the healthy controls and only 2 of the 74 control neurological patients had anti-LRP4 antibodies. Sera from MG patients with anti-LRP4 were able to inhibit the LRP4-agrin interaction and/or alter AChR clustering in muscle cells. Anti-LRP4 antibodies were detected in serum of approximately 9.2% of double seronegative patients with MG, indicating that LRP4 is another autoantigen in patients with MG and anti-LRP4 autoantibodies may be pathogenic through different immunopathogenic processes.

Introduction

MG affects about 20 per 100,000 people (Phillips, 2003, *Ann NY Acad Sci;* 998:407-412). MG patients show characteristic fatiguable weakness of voluntary muscles including ocular, oral-facial, bulbar and limb muscles, and in more severe cases respiratory difficulty. In the majority of MG patients, the disease appears to stem from an autoimmune response against muscle nicotinic AChR. Autoantibodies against AChRs can be detected in approximately 85% of patients with generalized MG (Richman et al., 1998, *Ann NY Acad Sci;* 841:450-465). Evidence from classic experiments indicates anti-AChR antibodies are pathogenic (Patrick and Lindstrom, 1973, *Science;* 180(88):871-872; Christadoss et al., 1981, *Ann NY Acad Sci;* 377:258-277; and Toyka et al., 21977, *N Engl J Med;* 296(3):125-131). About 40% of the anti-AChR seronegative patients have antibodies against MuSK (Hoch et al., 2001, *Nat Med;* 7(3):365-368; and Sanders et al., 2003, *Neurology;* 60(12):1978-1980), a muscle tyrosine kinase critical for NMJ formation and agrin-induced AChR clustering (Wu et al., 2010, *Development;* 137(7): 1017-1033). MuSK antibodies have been also shown to be pathogenic. They inhibit AChR clustering (Hoch et al., 2001, *Nat Med;* 7(3):365-368). Immunization with the extracellular domain of MuSK causes experimental autoimmune MG (EAMG) in rodents (Shigemoto et al., 2006, *J Clin Invest;* 116(4):1016-1024; Jha et al., 2006, *J Neuroimmunol;* 175(1-2):107-117; and Punga et al., 2011, *Exp Neurol;* 230(2):207-217). Moreover, passive transfer of IgG from anti-MuSK-positive MG patients causes EAMG (Cole et al., 2010, *J Physiol;* 588(Pt 17):3217-3229; and ter Beek et al., 2009, *Am J Pathol;* 175(4):1536-1544). The nature of the target antigen or antigens in double seronegative MG (i.e., without anti-AChR or anti-MuSK antibodies) was unclear although the NMJ impairment appears to be involved. Recently it has been reported that some of these individuals have anti-AChR antibodies of low avidity and can be demonstrated in vitro by binding to AChR clusters (Leite et al., 2008, *Brain;* 131(Pt 7):1940-1952).

LRP4 is a member of the low-density lipoprotein receptor (LDLR) family, and contains a large extracellular N-terminal region that possesses multiple epidermal growth factor (EGF) repeats and LDLR repeats, a transmembrane domain and a short C-terminal region without an identifiable catalytic motif (Johnson et al., 2005, *Hum Mol Genet;* 14(22):3523-3538; and Tian et al., 2006, *Eur J Neurosci;* 23(11):2864-2876). Recent studies indicate that LRP4 serves as a receptor of agrin (Zhang et al., 2008, *Neuron;* 60(2):285-297; and Kim N et al., 2008, *Cell;* 135(2):334-342) and is required for agrin-induced activation of MuSK and AChR clustering, and for NMJ formation (Weatherbee et al., 2006, *Development;* 133(24): 4993-5000). Moreover, heterologous expression of LRP4 in non-muscle cells enables agrin binding activity and reconstitutes agrin signaling including MuSK activation and Abl (Abelson murine leukemia viral oncogene homolog 1) phosphorylation (Zhang et al., 2008, *Neuron;* 60(2):285-297; and Kim N et al., 2008, *Cell;* 135(2):334-342). Evidence indicates that LRP4 interacts directly with agrin and MuSK (Zhang et al., 2008, *Neuron;* 60(2):285-297; and Kim N et al., 2008, *Cell;* 135(2):334-342). In a working model, agrin binds to LRP4 and thus increases its interaction with MuSK to activate the kinase and to initiate downstream signaling cascades for AChR clustering (Zhang et al., 2008, *Neuron;* 60(2): 285-297).

Considering the critical role of LRP4 in NMJ formation and the fact that many agrin signaling components have been implicated in muscular dystrophies, this example determined the role of LRP4 as an autoantigen in MG patients without antibodies to previously identified components of the NMJ. While this work was in progress, others reported that 2% of double seronegative Japanese MG patients have anti-LRP4 antibodies (Higuchi et al., 2011, *Ann Neurol;* 69(2):418-422) and that 6 of 13 tested double seronegative MG patients were positive for anti-LRP4 versus 0/4 healthy controls (Pevzner et al., 2012, *J Neurol;* 259(3):427-35 (Epub 2011 Aug. 5, 2011)). This example reports that LRP4 autoantibodies were detected in 9.2% of double seronegative MG patients, but not those with anti-AChR or anti-MuSK autoantibodies. Further, this example found high specificity of anti-LRP4 autoantibodies for MG, exploring sera of many neurological and psychiatric diseases. And, this example explored mechanisms by which LRP4 autoantibodies may alter the agrin signaling pathway, indicating pathophysiologic effects of LRP4 autoantibodies on AChR clustering and the agrin-LRP4 interaction. These results will provide insight into pathological mechanisms of double seronegative MG.

Methods

Patient sera. Serum samples were collected for diagnostic purposes or as part of approved research studies and had previously been tested for anti-AChR and anti-MuSK autoantibodies. Patients and healthy volunteers gave their written informed consent. Anti-AChR and anti-MuSK antibody titers were determined one of two methods. In the first method, anti-AChR and anti-MuSK antibody were determined by radioimmunoprecipitation assay (RIPA) kits (RSR Ltd, Cardiff, UK) according to the manufacturer's instructions with slight modifications, as previously described (Pevzner et al., 2012, *J Neurol;* 259(3):427-35 (Epub Aug. 5, 2011)). Anti-AChR titers below 0.2 nM/L and above 0.5 nM/L are considered negative and positive respectively, whereas values between 0.2-0.5 nM are considered ambiguous. Similarly, anti-MuSK titers below 0.02 and above 0.05 nM/L are considered negative and positive, respectively, whereas values between 0.02 and 0.05 nM/L are considered ambiguous. In the second method, anti-AChR binding antibodies were assayed at ARUP Laboratories (Salt Lake City, Utah; positive z 5 nM/L) or at the Mayo Clinic (Rochester, Minn.; positive >0.02 nM/L). Anti-MuSK was either done through Athena Laboratories (MuSK antibody test or Quantitative MuSK antibody titers) or by Dr. Angela Vincent as part of a multi-institutional study of serum from MG patients (positives as defined in Hoch et al., 2001, *Nat Med;* 7(3):365-368). Seropositive MG was defined as anti-AChR or anti-MuSK positive. Only definitely positive or definitely negative serum samples were examined for anti-LRP4 antibodies. Double seronegative MG was defined by the documented MG symptoms, findings on neurological examination, pharmacologic response to anticholinesterase agents and/or clinical neurophysiologic testing and the concurrent absence of both types of antibodies. Normal control sera were obtained from age matched volunteers serving as controls for other studies on MG.

In addition, sera from patients with the following other diseases were examined: amyotrophic lateral sclerosis (ALS) (n=9); chronic inflammatory demyelinating polyneuropathy (CLDP) (n=3); CNS primary Sjogrens syndrome (n=2); Guillain-Barre syndrome (GBS; acute inflammatory demyelinating polyneuropathy/AIDP) (n=6); acute motor axonal neuropathy (AMAN) (n=1); GBS with concomitant Isaac's syndrome (n=1); CNS Lyme disease (n=1); multiple sclerosis (MS) (n=18); paraneoplastic neuropathies (n=2); polymyositis in a patient with primary Sjogrens syndrome (n=1); polychondritis with CNS vasculitis (n=1); NMO (n=16); inflammatory myelopathies (not transverse myelitis or NMO; n=3); peripheral neuropathy of unknown etiology (n=1); schizophrenia (n=10); and neuroscarcoisis (n=1). Overall, we tested sera from 120 double-seronegative (AChR−/MuSK−) patients together with AChR+ (n=61) and AChR−/MuSK+ (n=36) MG sera and sera from normal (n=45) and other disease controls (n=76) as indicated above.

Recombinant protein production and purification. Constructs encoding full length LRP4 and ecto-LRP4 in pcDNA3.1-Myc/H is and alkaline phosphatase/Myc/His-tagged agrin (Agrin-AP) in pAP5 were prepared as described in Example 1 (see also Zhang et al., 2008, *Neuron;* 60(2):285-297).

ELISA detection of antibodies to LRP4. Maxi-Sorp Immuno 96-well Plates (Nunc) were coated with 50 µl of 1 µg/ml ecto-LRP4 in the coating buffer containing 50 mM carbonate (pH 9.6) at 40° C. overnight, washed six times with TBST (0.1% Tween 20 in 50 mM Tris, 150 mM NaCl, pH 7.6) and incubated with the blocking buffer containing 5% nonfat milk in TBST to block non-specific binding. Sera were diluted 1:10 in the blocking buffer (100 µl per well) and incubated for 1 hr at 37° C. After wash with TBST, the wells were incubated with alkaline phosphatase (AP)-goat anti-human IgG+IgM+IgA secondary antibody (Abcam), diluted 1:30,000 in TBST, at 37° C. for 1 hr. Activity of immobilized AP was measured by optical density (OD) assay (at 405 nm) following incubation in the substrate buffer containing 0.5 mM $MgCl_2$, 3 mg/ml p-nitrophenyl phosphate (pNPP) and 1M diethanolamine (DEA), at room temperature for 30 min. Each sample was assayed in duplicate and repeated more than three times. Nonspecific signal was determined by OD reading of wells coated with the coating buffer alone followed by incubation of secondary antibody and substrate. Intra-assay and inter-assay coefficient of variability were 8.3% and 12.4%, respectively. All samples were examined blindly without previous information of the patients' condition or diagnosis. Cut-off value was set as mean+4 standard deviation (SD) of control normal human sera, representing confidence of 99.99% (Kenney J F, Keeping E S. The Standard Deviation and Calculation of the Standard Deviation. Mathematics of statistics. 3rd ed. Princeton, N.J.: Van Nostrand; 1962:77-80).

Immunoprecipitation of LRP4 by autoantibodies. HEK293 cells were transfected by PEI (polyethylenimine) with Myc-tagged full length LRP4, as described in Example 1 (see also, Zhang et al., 2008, *Neuron;* 60(2):285-297; and Luo et al., 2008, *Neuron;* 60(1):97-110). Lysates (500 µl, 1 mg/ml protein, in RIPA buffer) were incubated with 10 µl of sera (sera 21321, 22212, 23437 and 23473) at 4° C. overnight with agitation, followed by 2-hr incubation with 50 µl Protein-G beads at 4° C. Bead-immobilized proteins were subjected to SDS-PAGE and western blotting with anti-Myc antibody.

Effects of LRP4 positive sera on agrin/LRP4 interaction. Maxi-Sorp Immuno plates were coated with ecto-LRP4 as described above, and incubated with 100 µl of 0.5 µM AP-agrin, a fusion protein of AP and agrin (as described in Example 1; see also Zhang et al., 2008, *Neuron;* 60(2):285-297), together with 10 µl of LRP4+ sera (sera 21321, 22212, 23437 and 23473) or control normal serum, at 37° C. for 1 hr. After wash, activity of immobilized AP was measured as described above with pNPP as substrate.

Effects of LRP4 positive sera on AChR clustering. AChR clustering was assayed as previously described with minor modifications (see Example 1; Zhang et al., 2008, *Neuron;* 60(2):285-297; Luo et al., 2008, *Neuron;* 60(1):97-110; and Zhang et al., 2007, *J Neurosci;* 27(15):3968-3973). C2C12 myotubes were treated with neural agrin (10 ng/ml) together with LRP4 positive sera (1:150 dilution) (sera 21321, 22212, 23437 and 23473) for 16 hr, fixed in 4% paraformaldehyde, and incubated with 50 nM rhodamine-conjugated-bungarotoxin (R-BTX) (Invitrogen) to label AChR clusters. Myotubes were viewed under a Zeiss epifluoresence microscope and AChR clusters with diameters or a longer axis ≥4 μm were scored. At least 10 views per dish and at least 2 dishes were scored in each of three independent experiments.

Results

Figure 10:
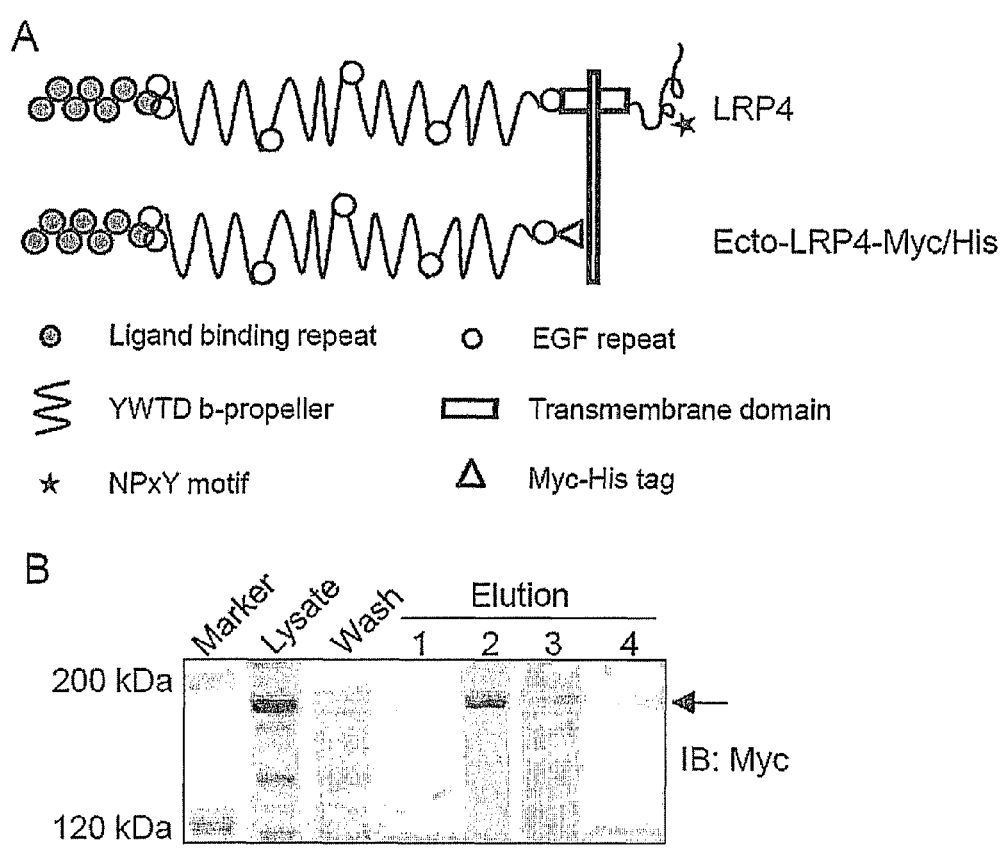
FIGS. 10A and 10B show preparation of ecto-LRP4.
Figure 11:
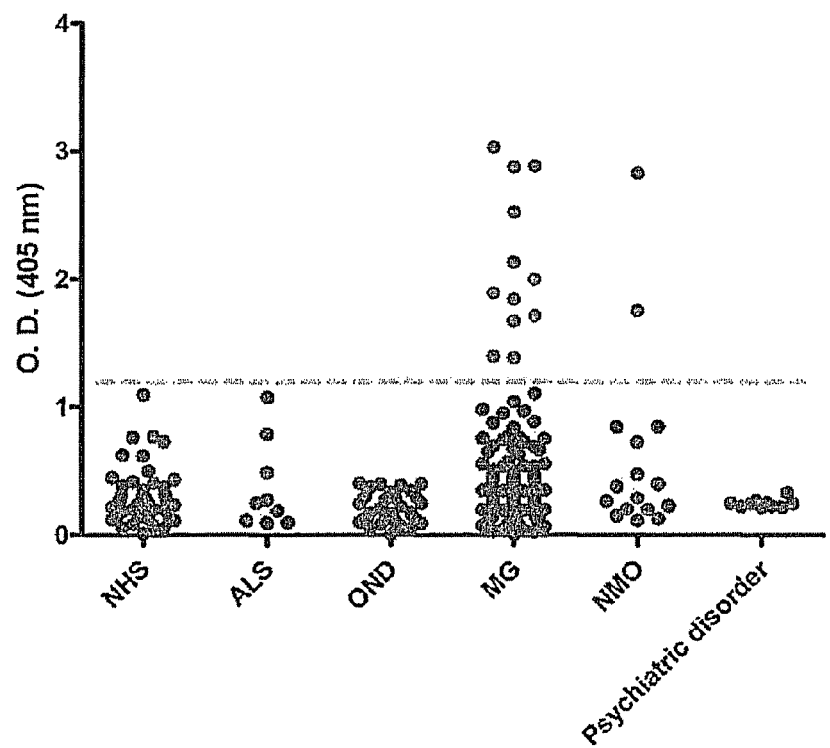
FIG. 11 shows ELISA of anti-LRP4 autoantibodies. OD readings of NHS (control) were 0.31 (0.22) (n=45). The cut-off is indicated by the dotted line.
Figure 12:
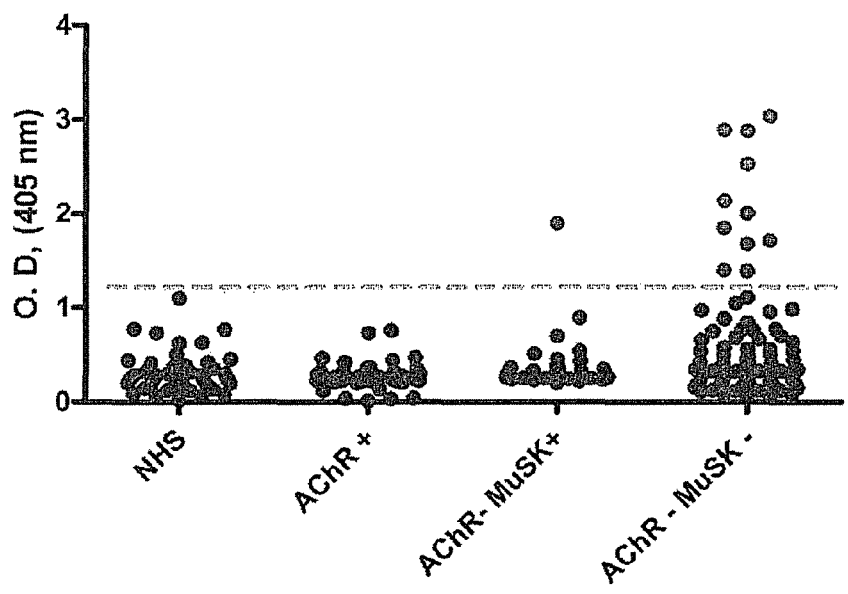
FIG. 12 shows distribution of anti-LRP4 autoantibodies among MG patients. Of 217 MG samples, 61 were AChR+; 36 were AChR–/MuSK+; and 120 were double seronegative (AChR–/MuSK–). The cut-off (the dotted line) was set as mean±4 SD.

Detection of anti-LRP4 autoantibodies in sera of MG patients. To determine whether "seronegative" MG patients produce anti-LRP4 autoantibodies, a generated Myc/His-tagged rat ecto-LRP4 was generated, as described in Example 1 (see also, Zhang et al., 2008, *Neuron;* 60(2):285-297). The purified protein resolved around 200 kDa on SDS-PAGE, in agreement with the predicted molecular weight (190 kDa). Moreover, it could be detected by a commercial antibody against the Myc epitope that is located at the C-terminus (FIG. 10B), indicating that ecto-LRP4 contained the entire extracellular region of LRP4. The ecto-LRP4 protein was used in ELISA assays for autoantibodies in sera from double seronegative MG patients as well as various groups of individuals. With the mean plus 4 SD of normal sera as cut-off, none of normal serum samples were positive for LRP4 autoantibodies. No positive was detected in sera from patients with psychiatric disorders or non-MG neurological disorders as defined in methods with the exception of 2 of 16 sera of NMO patients (see Discussion) (FIG. 11). Of 217 MG patients, 12 were positive for LRP4 antibodies (FIG. 11): 11 were among 120 double seronegative patients and 1 from 36 AChR−, but MuSK+ patients. None of the AChR+ patients generated detectable LRP4 antibodies (FIG. 12).

Figure 13:
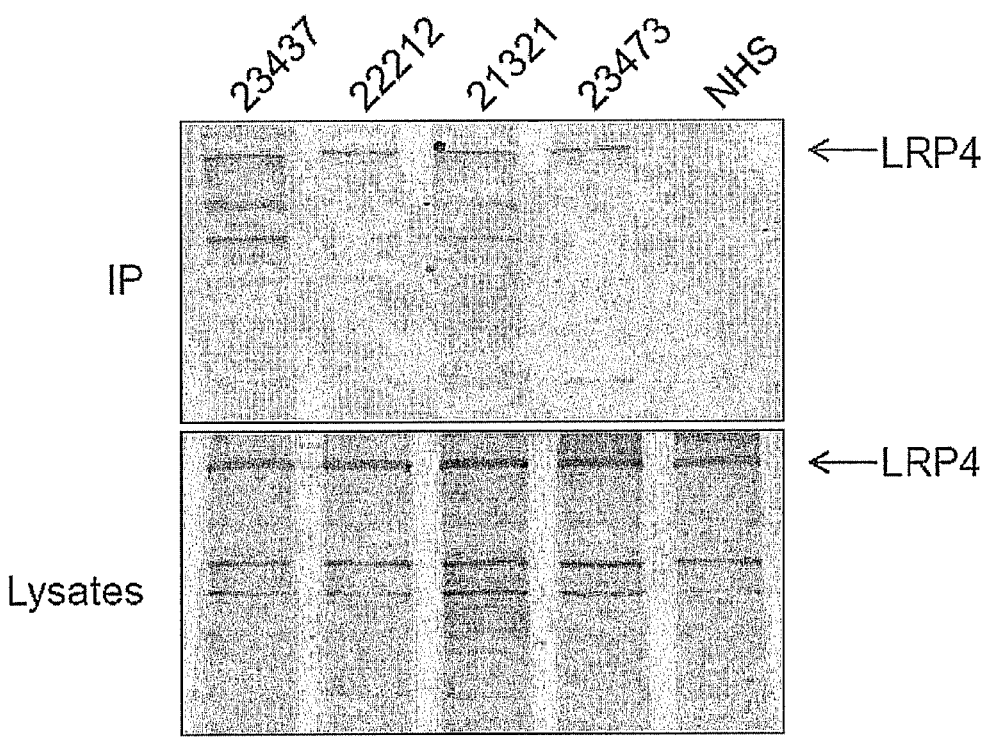
FIG. 13 shows recognition of full length LRP4 by LRP4+ sera. Lysates of LRP4-transfected HEK293 cells were incubated with LRP4+ sera or NHS. Resulting immunocomplex and lysates (to indicate equal amounts of input) were subjected to Western blotting with anti-Myc antibody.

To confirm that the target antigen of these sera was full length LRP4, rather than any contaminant in the ecto-LRP4 preparation, four LRP4+ sera (three from the AChR−/MuSK− group (21321, 22212, and 23437) and one from the AChR−/MuSK+ group (23473)) were incubated with lysates of HEK293 cells expressing Myc-tagged full length LRP4. The immunocomplex was purified by protein G immobilized on beads, resolved by SDS-PAGE and subjected to western blot analysis with anti-Myc antibody. As expected, full length LRP4 was not detectable in the immunocomplex by normal human serum. However, Myc-tagged LRP4 was detected in the precipitates by four LRP4+ sera, indicating that LRP4 autoantibodies were able to recognize full length LRP4 expressed in transfected cells (FIG. 13).

Figure 14:
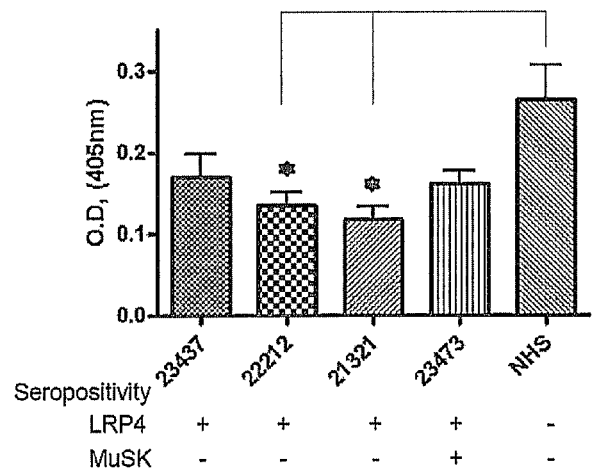
FIG. 14 shows inhibition of agrin-LRP4 interaction by LRP4+ sera. The interaction was assayed by ELISA, in the presence of control or LRP4+ sera. Data shown were mean±SD (n=3). *P<0.05, compared with normal human serum (NHS).

LRP4 autoantibody-mediated disruption of the agrin-LRP4 interaction. LRP4 interacts directly via its extracellular domain with agrin. Knowing that LRP4 autoantibodies interact with full length LRP4, it was assayed whether they interfere with the agrin-LRP4 interaction. The interaction was assayed by ELISA by coating plates with ecto-LRP4, followed by incubation with AP-agrin, in the presence of normal or LRP4+ sera (1:10 dilution). As shown in FIG. 14, the OD readings in the ELISA were reduced at least in the presence of sera 21321 and 22212, compared to readings in the presence of normal human serum, suggesting that LRP4 autoantibodies may inhibit the agrin-LRP4 interaction.

Figure 15:
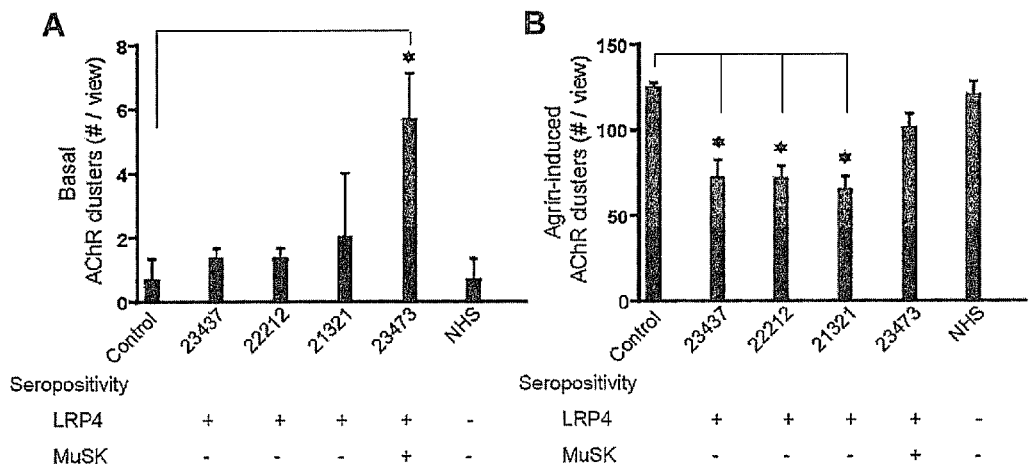
FIGS. 15A to 15B show serum samples with LRP4+ antibodies alter AChR clustering in myotubes. Quantitative data of basal (FIG. 15A) and induced AChR clusters (FIG. 15B). Data shown as mean (SD). *P<0.05 compared with control.

Alteration of basal and agrin-induced AChR clustering by patient LRP4 autoantibodies. LRP4 is a component of the agrin receptor complex and critical for NMJ formation and agrin-induced AChR clustering. Being able to recognize full length LRP4 (FIG. 13) and to interfere with agrin-LRP4 interaction (FIG. 14), the autoantibodies may change agrin-induced AChR clustering. To test this hypothesis, C2C12 myotubes were treated with neural agrin alone or together with control or LRP4+ sera, and examined for AChR clusters. As shown in FIG. 15, induced AChR clusters were not altered by nouual human sera, but were inhibited by sera 21321, 22212, and 23437. Serum 23473 had no significant effect on agrin-induced AChR clustering. These results suggest that LRP4 autoantibodies may have differential effect on AChR clustering induced by agrin.

Antibodies interacting with a transmembrane protein may cause its dimerization or oligomerization which may result in its activation (Spaargaren et al., 1991, *J Biol Chem;* 266(3):1733-1739). Antibodies against the extracellular domain of MuSK were shown to activate MuSK, leading to AChR clustering in cultured myotubes in the absence of agrin (Hopf and Hoch, 1998, *J Biol Chem;* 273(11):6467-6473). Moreover, MuSK autoantibodies from MG patients also induced AChR clustering (Hoch et al., 2001, *Nat Med;* 7(3):365-368). As shown in Example 1, overexpressed LRP4 enhances MuSK activity in the absence of agrin (see also Zhang et al., 2008, *Neuron;* 60(2):285-297). Thus, it was assayed whether LRP4 autoantibodies were able to induce AChR clustering in the absence of agrin because aggregated LRP4 may promote MuSK dimerization and/or activation. For this assay, C2C12 myotubes were treated without (control) or with LRP4+ sera and assayed for spontaneous AChR clusters. No apparent effect was observed with sera 21321, 22212, and 23437 or the normal human serum NHS2. However, the musk+/LRP4+ serum 23473, which did not inhibit agrin-induced AChR clustering (FIG. 15B), was able to increase the number of spontaneous AChR clusters.

Discussion

About 85% of MG patients have detectable serum antibodies against AChRs with 20-40% of the remaining patients being positive for anti-MuSK antibodies (Hoch et al., 2001, *Nat Med;* 7(3):365-368; and Meriggioli and Sanders, 2009, *Lancet Neurol;* 8(5):475-490). This would leave about 10% of the MG patients double seronegative, i.e., without detectable antibodies against any known autoantigen. This example presents evidence that anti-LRP4 autoantibodies exist in sera of the double seronegative MG patients. In a cohort of 120 AChR−/Musk− patients, 11 were found positive for anti-LRP4 antibodies, accounting for 9.2%. Additional studies have identified LRP4 autoantibodies in double seronegative MG patients (Higuchi et al., 2011, *Ann Neurol;* 69(2):418-422; and Pevzner et al., 2012, *J Neurol;* 259(3):427-35 (Epub 2011 Aug. 5, 2011). Together, these data suggest that LRP4 may be a novel antigen in many double seronegative MG patients. It is worth noting that in agreement with the Higuchi study (Higuchi et al., 2011, *Ann Neurol;* 69(2):418-422), this example failed to detect LRP4 autoantibodies in the cohort of 61 patients with AChR antibodies. This example found one LRP4+ serum in the cohort of 36 patients with MuSK antibodies whereas 3 of 28 patients with MuSK antibodies in the Higuchi cohort were positive for LRP4. In the rare MG patients who are positive for both anti-LRP4 and anti-MuSK the relative role of these two different antibodies in disease pathogenesis is unknown. Interestingly, of a cohort of 272 double seronegative patients of Higuchi et al., (Higuchi et al., 2011, *Ann Neurol;* 69(2):418-422) only 6 patients were positive for LRP4 antibodies, accounting for ~2% of the double seronegative sera differing with the 9.2% reported in this study. Pnezner reported about 50% (6/13) of the tested double negative MG patients had anti-LRP4 antibodies (Pevzner et al., 2012, *J Neurol;* 259(3):427-35 (Epub 2011 Aug. 5, 2011). The reason for the difference between the three studies is unclear. It may result from the difference of patient ethnicity and countries of origin. Indeed a similar geographic difference was also observed in MG patients with MuSK autoantibodies; the reported percentage of MuSK positive patients in all AChR negative MG patients varies from 0 to 50% (Guptill et al., 2011, *Muscle Nerve;* 44(1):36-40). Intriguingly, LRP4 autoantibodies were detected in two of sixteen NMO patients. It is known that several patients have both anti-AChR and NMO antibodies (anti-aquaporin-4) (McKeon et al., 2009, *Muscle Nerve;* 39(1):87-90), while many NMO patients often have other autoantibodies such as anti-nuclear antibodies (ANA) and anti-ENA (extractable nuclear antigens) antibodies without having systemic lupus erythematosus or Sjogren's syndrome (Hamnik et al., 2008, *Semin Ophthalmol;* 23(3):191-200; and Pittock et al., 2008, *Arch Neurol;* 65(1):78-83). In addition NMO and/or transverse myelitis have been reported in the same individuals and the onset of the two diseases may occur years apart (see, for example, Gotkine et al., 2006, *Neurology;* 67(5):881-883).

Pathogenic mechanisms of anti-AChR antibodies have been well studied. In rabbit, mouse, and rat models of EAMG, anti-AChR antibodies block the activity of the ActR (Green et al., 1975, *Proc R Soc Lond B Biol Sci;* 189(1094):57-68; Bevan et al., 1976, *Nature;* 260(5550):438-439; and Lambert et al., 1976, *Ann NY Acad Sci;* 274:300-318), accelerate the internalization and degradation of AchR5 (Lindstrom and Einarson, 1979, *Muscle Nerve;* 2(3):173-179; Tronconi et al., 1981, *Neurology;* 31(11):1440-1444; and Tzartos et al., 1985, *J Immunol;* 134(4):2343-2349)38-40) and fix complement, which could mediate NMJ destruction and AChR loss (Lambert et al., 1976, *Ann NY Acad Sci;* 274:300-318; Aharonov et al., 1975, *Lancet;* 2(7930):340-342; and Engel et al., 1976, *J Neuropathol Exp Neurol;* 35(5):569-587). The AChR deficiency decreases the amplitude of miniature EP potentials (mEPPs) and hence that of EP potentials (EPPs), which consequently reduces the safety margin of neuromuscular transmission (Kao and Drachman, 1977, *Science;* 196(4289):527-529; and Lindstrom et al., 1976, *Neurology;* 26(11):1054-1059). On the other hand, anti-MuSK antibodies seem to inhibit the activity of MuSK, leading to attenuation of agrin-induced AChR clustering thus reducing AChR levels at the junctional folds (Jha et al., 2006, *J Neuroimmunol;* 175(1-2):107-117; Punga et al., 2011, *Exp Neurol;* 230(2):207-217; ter Beek et al., 2009, *Am J Pathol;* 175(4):1536-1544; Shigemoto et al., 2008, *Ann NY Acad Sci;* 1132:93-98; and Cole et al., 2008, *Ann Neurol;* 63(6):782-789). In addition, NMJs and AChR scaffolds are disrupted in anti-MuSK induced EAMG. However, anti-MuSK antibodies in MG patients are predominantly of the IgG4 subclass (McConville et al., 2004, *Ann Neurol;* 55(4):580-584; and Tsiamalos et al., 2009, *Eur J Neurol;* 16(8):925-930), which do not bind and activate complement. Thus, it seems that anti-MuSK antibody-associated MG may have different etiological and pathological mechanisms from those of the anti-AChR associated MG. In addition, anti-MuSK patients do not appear to have thymic hyperplasia or thymoma (Zhou et al., 2004, *Muscle Nerve;* 30(1):55-60; Lavrnic et al., 2005, *J Neurol Neurosurg Psychiatry;* 76(8):1099-1102; Leite et al., 2005, *Ann Neurol;* 57(3):444-448; Saka et al., 2005, *Neurology;* 65(5):782-783 (and author reply 782-783); and Suhail et al., 2010, *Int J Neurosci;* 120(2):115-119).

Whether and how LRP4 autoantibodies are pathogenic requires further study. This example demonstrates that some LRP4+ (but AChR– and MuSK–) sera were able to disrupt the agrin-LRP4 interaction and inhibit agrin-induced AChR clustering. Serum 23473, which was also MuSK+, had no effect on the agrin-LRP4 interaction nor did it inhibit agrin-induced AChR clustering. It increased basal AChR clusters which may be due to anti-MuSK antibodies, instead of those directed against LRP4. Considering the large size of the extracellular domain of LRP4, it is likely that the pathogenic mechanisms of LRP4 antibodies could be complex. For example, LRP4 also interacts with MuSK in addition to agrin (Zhang et al., 2008, *Neuron;* 60(2):285-297; and Kim N et al., 2008, *Cell;* 135(2):334-342). Therefore, the anti-LRP4 antibodies might prevent LRP4 from interacting with MuSK. They may also cause its internalization and subsequent degradation. Finally, the majority of LRP4 autoantibodies appeared to be IgG1 (Higuchi et al., 2011, *Ann Neurol;* 69(2):418-422), similar to those against of AChR, which are able to activate complement (Lennon et al., 1978, *J Exp Med;* 147(4):973-983). Therefore, it is possible that complement may be involved in the pathogenesis of MG in some patients with LRP4 autoantibodies. If so this would differ from the presumed mechanism of action of the anti-MuSK autoantibodies.

Example 2 has also published as "Autoantibodies to Lipo-protein-Related Protein 4 in Patients With Double-Seronegative Myasthenia Gravis;" Zhang B, Tzartos J S, Belimezi M, Ragheb S, Bealmear B, Lewis R A, Xiong W C, Lisak R P, Tzartos S J, and Mei L; *Arch Neurol;* 2012 April 69(4):445-51 [Epub 2011 Dec. 12].

Example 3

Generation of a Mouse Model of Myasthenia Gravis by Immunizing Mice with LRP4

It is important to determine whether LRP4 is a target antigen in MG and whether LRP4 autoantibodies are pathogenic. To address these important questions, with this example a LRP4 model of myasthenia gravis was generated by immunizing with ecto-LRP4. A/J female mice were chosen because this strain and sex was most responsive to immunization with ecto-Musk. Ecto-LRP4 in PBS was emulsified with equal volume of CFA and injected subcutaneously into 8-weeks-old female A/J mice at three subcutaneous locations on the back. Experimental mice (n=9) were injected with ecto-LRP4/CFA (65 µl in volume for each location, total 20 µg of ecto-LRP4 for each mouse) whereas control mice (n=3) were injected with PBS/CFA. Mice received a boost injection on Day 28, and were characterized on Day 35 (i.e., 7 days after first boost).

Figure 16:
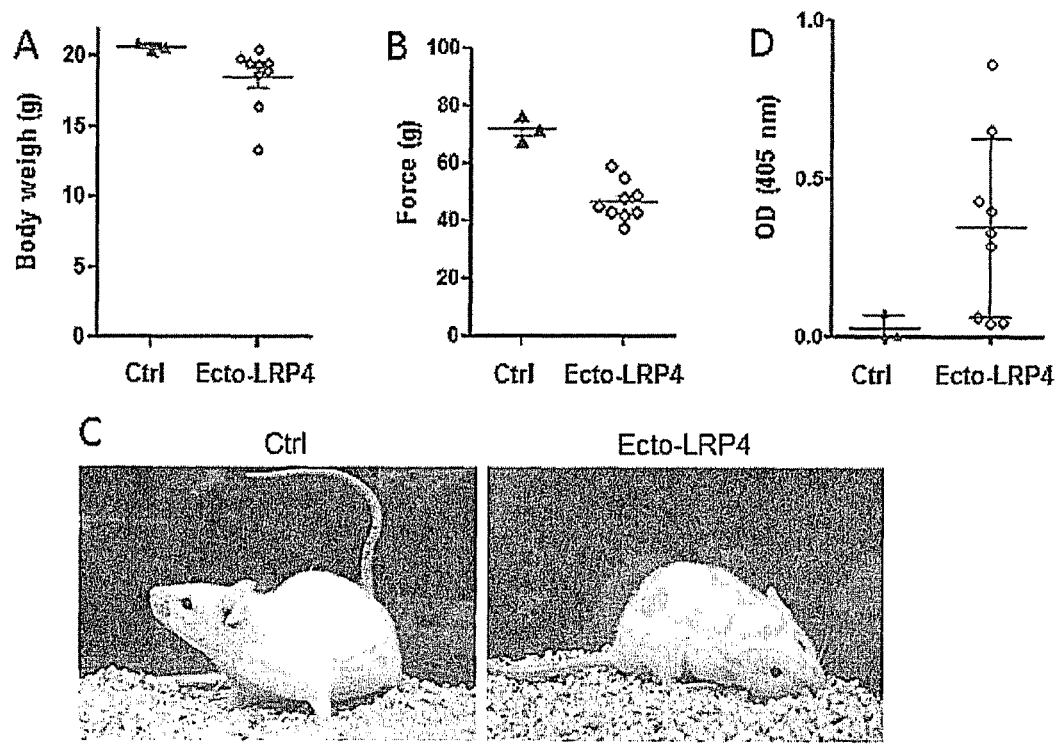
FIG. 16A-16D shows the development of EAMG after immunization with recombinant LRP4.

FIG. 16A-16D shows the development of EAMG after immunization with recombinant LRP4. FIG. 16A shows reduced body weight in ecto-LRP4-injected mice (p=0.02). FIG. 16B shows reduced grip strength in ecto-LRP4-injected mice (p=0.004). FIG. 16C shows one mouse, representative of most severely affected LRP4 EAMG mice, with chin down and flaccid tail. Notice the two images were in different scales, and did not indicate body size. FIG. 16D shows LRP4 immunoreactivity in LRP4-injected mice was increased. Assay was done, as in FIGS. 12 and 13 (p=0.04). In FIGS. 16A, 16B, and 16D, data shown were shown as mean±SD. Ctrl (control), n=3; Ecto-LRP4 (ecto-LRP4-injected), n=9. t-test was used; long bar, mean; short bar, SD.

Intriguingly, ecto-LRP4-injected mice showed significant weight loss (FIG. 16A). Muscle grip strength was reduced in ecto-LRP4-injected mice (FIG. 16B). Some of them showed signs of muscle weakness including chin down, flaccid tail, and unwillingness to move when handled, in contrast to control mice (FIG. 16C). Remarkably, LRP4 immunoreactivity was significantly higher in ecto-LRP4-injected mice, compared to controls (FIG. 16D), suggesting that they generated LRP4 antibodies. These results suggest that LRP4 autoantibodies are pathogenic. This model may be useful to study pathological mechanisms of LRP4 autoantibodies and to develop and evaluate therapeutic strategies or methods.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified. The terms "comprises" and variations thereof do not have a limiting meaning where these terms appear in the description and claims. Unless otherwise specified, "a," "an," "the," and "at least one" are used interchangeably and mean one or more than one.

SEQUENCE LISTING FREE TEXT

SEQ ID NO:1-10 Synthetic oligonucleotide sequences for miRNA constructs
SEQ ID NO:11 Amino acid sequence of human low density lipoprotein receptor-related protein 4 (LRP4) precursor.

What is claimed is:

1. An assay kit for detecting autoantibodies to the low density lipoprotein receptor-related protein 4 (LRP4) polypeptide in a bodily fluid of a subject, the kit comprising an isolated LRP4 polypeptide or isolated fragment thereof;
   wherein the fragment thereof comprises the extracellular domain of the LRP4 polypeptide, the intracellular domain of the LRP4 polypeptide, one or more of the epidermal growth factor (EGF) repeats of the LRP4 polypeptide, and/or one or more of the low density lipoprotein receptor (LDLR) repeats of the LRP4 polypeptide; and
   wherein the isolated LRP4 polypeptide or isolated fragment thereof is immobilized on a solid surface, wherein the solid surface comprises a bead or biochip.

2. The assay kit of claim 1 further comprising an isolated muscle specific tyrosine kinase (MuSK) polypeptide or isolated fragment thereof, wherein a MuSK polypeptide fragment thereof comprises the extracellular domain of the MuSK polypeptide.

3. The assay kit of claim 2, wherein the MuSK polypeptide or fragment thereof is immobilized on a solid surface.

4. The assay kit of claim 3, wherein the MuSK polypeptide or fragment thereof is immobilized on a bead or biochip.

5. The assay kit of claim 1 further comprising
   a secondary anti-human immunoglobulin antibody.

6. The assay kit of claim 5, wherein the secondary anti-human immunoglobulin antibody comprises a detectable label attached to the secondary anti-human immunoglobulin antibody.

7. The assay kit of claim 1 further comprising
   an isolated muscle nicotinic acetylcholine receptor (AChR) polypeptide or an isolated fragment thereof;
   and wherein a muscle nicotinic AChR polypeptide fragment thereof comprises the extracellular domain of the muscle nicotinic AChR polypeptide and/or a subunit of the muscle nicotinic AChR polypeptide.

8. The assay kit of claim 7, wherein muscle nicotinic AChR or fragment thereof is immobilized on a solid surface.

9. The assay kit of claim 8 wherein muscle nicotinic AChR polypeptide or fragment thereof is immobilized on a bead or biochip.

10. The assay kit of claim 7 further comprising an isolated muscle specific tyrosine kinase (MuSK) polypeptide or isolated fragment thereof, wherein a MuSK polypeptide fragment thereof comprises the extracellular domain of the MuSK polypeptide.

11. The assay kit of claim 1, wherein the LRP4 polypeptide or fragment thereof comprises a detectable label attached to the LRP4 polypeptide or fragment thereof.

12. The assay kit of claim 1, wherein the LRP4 polypeptide comprises at least about 95% sequence identity to SEQ ID NO:11.

13. The assay kit of claim 1, wherein the LRP4 polypeptide comprises SEQ ID NO:11.

14. An assay kit for detecting autoantibodies to the low density lipoprotein receptor-related protein 4 (LRP4) polypeptide in bodily fluid of a subject, the assay kit comprising an isolated LRP4 polypeptide or isolated fragment thereof;
   wherein the fragment thereof comprises the extracellular domain of the LRP4 polypeptide, the intracellular domain of the LRP4 polypeptide, one or more of the epidermal growth factor (EGF) repeats of the LRP4 polypeptide, and/or one or more of the low density lipoprotein receptor (LDLR) repeats of the LRP4 polypeptide;
   wherein the isolated LRP4 polypeptide or isolated fragment thereof is immobilized on a solid surface, wherein the solid surface comprises a bead or biochip; and
   wherein the LRP4 polypeptide or fragment thereof comprises a detectable label attached to the LRP4 polypeptide or fragment thereof.

15. The assay kit of claim 14 further comprising an isolated muscle nicotinic acetylcholine receptor (AChR) polypeptide or isolated fragment thereof, wherein a muscle nicotinic AChR fragment thereof comprises the extracellular domain of the muscle nicotinic AChR polypeptide and/or a subunit of the muscle nicotinic AChR polypeptide.

16. The assay kit of claim 15 further comprising an isolated muscle specific tyrosine kinase (MuSK) polypeptide or isolated fragment thereof, wherein a MuSK polypeptide fragment thereof comprises the extracellular domain of the MuSK polypeptide.

17. An assay kit according to claim 14, further comprising a secondary anti-human immunoglobulin antibody.

18. The assay kit of claim 17, wherein the secondary anti-human immunoglobulin antibody comprises a detectable label attached to the secondary anti-human immunoglobulin antibody.

19. The assay kit of claim 14, wherein the LRP4 polypeptide comprises SEQ ID NO:11.

20. The assay kit of claim 14, wherein the LRP4 polypeptide comprises at least about 95% sequence identity to SEQ ID NO:11.

* * * * *

SEQUENCE LISTING

```
<160> NUMBER OF SEQ ID NOS: 11

<210> SEQ ID NO 1
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 1
tgctgtaaca cagcagagcc tcagcagttt tggccactga ctgactgctg aggctgctgt    60
gtta                                                                 64

<210> SEQ ID NO 2
<211> LENGTH: 63
<212> TYPE: DNA
<213> ORGANISM: artificial
<220> FEATURE:
<223> OTHER INFORMATION: Synthetic oligonucleotide sequence for miRNA
      constructs

<400> SEQUENCE: 2
ctgtaacaca gcagcctcag cagtcagtca gtggccaaaa ctgctgaggc tctgctgtgt    60
tac                                                                  63

<210> SEQ ID NO 3
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 3
tgctgatcac agggtgcaac acaatggttt tggccactga ctgaccattg tgtcaccctg    60
tgat                                                                 64

<210> SEQ ID NO 4
<211> LENGTH: 64
<212> TYPE: DNA
<213> ORGANISM: artificial
<220> FEATURE:
<223> OTHER INFORMATION: Synthetic oligonucleotide sequence for miRNA
      constructs
```

```
<400> SEQUENCE: 4
cctgatcaca gggtgacaca atggtcagtc agtggccaaa accattgtgt tgcaccctgt      60
gatc                                                                  64

<210> SEQ ID NO 5
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 5
tgctgttaac attgcagttc tcctcagttt tggccactga ctgactgagg agatgcaatg      60
ttaa                                                                  64

<210> SEQ ID NO 6
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 6
cctgttaaca ttgcatctcc tcagtcagtc agtggccaaa actgaggaga actgcaatgt      60
taac                                                                  64

<210> SEQ ID NO 7
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 7
tgctgaatac atgtacccgc ccatgggttt tggccactga ctgacccatg ggcgtacatg      60
tatt                                                                  64

<210> SEQ ID NO 8
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 8
cctgaataca tgtacgccca tgggtcagtc agtggccaaa acccatgggc gggtacatgt      60
attc                                                                  64

<210> SEQ ID NO 9
<211> LENGTH: 63
<212> TYPE: DNA
<213> ORGANISM: artificial
<220> FEATURE:
<223> OTHER INFORMATION: Synthetic oligonucleotide sequence for miRNA
      constructs
```

```
<400> SEQUENCE: 9
gctgtagcac agctgattat acacggtttt ggccactgac tgaccgtgta tacagctgtg    60
cta                                                                   63

<210> SEQ ID NO 10
<211> LENGTH: 64
<212> TYPE: DNA
<213> ORGANISM: artificial
<220> FEATURE:
<223> OTHER INFORMATION: Synthetic oligonucleotide sequence for miRNA
      constructs

<400> SEQUENCE: 10
cctgtagcac agctgtatac acggtcagtc agtggccaaa accgtgtata atcagctgtg    60
ctac                                                                  64

<210> SEQ ID NO 11
<211> LENGTH: 1905
<212> TYPE: PRT
<213> ORGANISM: Homo sapiens

<400> SEQUENCE: 11
```

| | | | | | | | | | | | | | | |
|---|---|---|---|---|---|---|---|---|---|---|---|---|---|---|
| Met | Arg | Arg | Gln | Trp | Gly | Ala | Leu | Leu | Gly | Ala | Leu | Leu | Cys | Ala |
| 1 | | | | 5 | | | | | 10 | | | | | 15 |
| His | Gly | Leu | Ala | Ser | Ser | Pro | Glu | Cys | Ala | Cys | Gly | Arg | Ser | His Phe |
| | | | 20 | | | | | 25 | | | | | 30 | |
| Thr | Cys | Ala | Val | Ser | Ala | Leu | Gly | Glu | Cys | Thr | Cys | Ile | Pro | Ala Gln |
| | | | 35 | | | | 40 | | | | | 45 | | |
| Trp | Gln | Cys | Asp | Gly | Asp | Asn | Asp | Cys | Gly | Asp | His | Ser | Asp | Glu Asp |
| 50 | | | | | 55 | | | | | 60 | | | | |
| Gly | Cys | Ile | Leu | Pro | Thr | Cys | Ser | Pro | Leu | Asp | Phe | His | Cys | Asp Asn |
| 65 | | | | 70 | | | | | 75 | | | | | 80 |
| Gly | Lys | Cys | Ile | Arg | Arg | Ser | Trp | Val | Cys | Asp | Gly | Asp | Asn | Asp Cys |
| | | | | 85 | | | | | 90 | | | | | 95 |
| Glu | Asp | Asp | Ser | Asp | Glu | Gln | Asp | Cys | Pro | Pro | Arg | Glu | Cys | Glu Glu |
| | | | | 100 | | | | | 105 | | | | 110 | |
| Asp | Glu | Phe | Pro | Cys | Gln | Asn | Gly | Tyr | Cys | Ile | Arg | Ser | Leu | Trp His |
| | | | 115 | | | | | 120 | | | | | 125 | |
| Cys | Asp | Gly | Asp | Asn | Asp | Cys | Gly | Asp | Asn | Ser | Asp | Glu | Gln | Cys Asp |
| | | 130 | | | | | 135 | | | | | 140 | | |
| Met | Arg | Lys | Cys | Ser | Asp | Lys | Glu | Phe | Arg | Cys | Ser | Asp | Gly | Ser Cys |
| 145 | | | | | 150 | | | | | 155 | | | | | 160 |
| Ile | Ala | Glu | His | Trp | Tyr | Cys | Asp | Gly | Asp | Thr | Asp | Cys | Lys | Asp Gly |
| | | | | 165 | | | | | 170 | | | | | 175 |
| Ser | Asp | Glu | Glu | Asn | Cys | Pro | Ser | Ala | Val | Pro | Ala | Pro | Pro | Cys Asn |
| | | | | 180 | | | | | 185 | | | | 190 | |
| Leu | Glu | Glu | Phe | Gln | Cys | Ala | Tyr | Gly | Arg | Cys | Ile | Leu | Asp | Ile Tyr |
| | | | 195 | | | | | 200 | | | | | 205 | |
| His | Cys | Asp | Gly | Asp | Asp | Asp | Cys | Gly | Asp | Trp | Ser | Asp | Glu | Ser Asp |
| | | 210 | | | | | 215 | | | | | 220 | | |
| Cys | Ser | Ser | His | Gln | Pro | Cys | Arg | Ser | Gly | Glu | Phe | Met | Cys | Asp Ser |
| 225 | | | | | 230 | | | | | 235 | | | | | 240 |
| Gly | Leu | Cys | Ile | Asn | Ala | Gly | Trp | Arg | Cys | Asp | Gly | Asp | Ala | Asp Cys |
| | | | | 245 | | | | | 250 | | | | | 255 |
| Asp | Asp | Gln | Ser | Asp | Glu | Arg | Asn | Cys | Thr | Thr | Ser | Met | Cys | Thr Ala |
| | | | | 260 | | | | | 265 | | | | | 270 |

-continued

```
Glu Gln Phe Arg Cys His Ser Gly Arg Cys Val Arg Leu Ser Trp Arg
        275                 280                 285
Cys Asp Gly Glu Asp Cys Ala Asp Asn Ser Asp Glu Glu Asn Cys
        290                 295                 300
Glu Asn Thr Gly Ser Pro Gln Cys Ala Leu Asp Gln Phe Leu Cys Trp
305                 310                 315                 320
Asn Gly Arg Cys Ile Gly Gln Arg Lys Leu Cys Asn Gly Val Asn Asp
                325                 330                 335
Cys Gly Asp Ser Asp Glu Ser Pro Gln Gln Asn Cys Arg Pro Arg
        340                 345                 350
Thr Gly Glu Glu Asn Cys Asn Val Asn Asn Gly Gly Cys Ala Gln Lys
        355                 360                 365
Cys Gln Met Val Arg Gly Ala Val Gln Cys Thr Cys His Thr Gly Tyr
        370                 375                 380
Arg Leu Thr Glu Asp Gly His Thr Cys Gln Asp Val Asn Glu Cys Ala
385                 390                 395                 400
Glu Glu Gly Tyr Cys Ser Gln Gly Cys Thr Asn Ser Glu Gly Ala Phe
                405                 410                 415
Gln Cys Trp Cys Glu Thr Gly Tyr Glu Leu Arg Pro Asp Arg Arg Ser
        420                 425                 430
Cys Lys Ala Leu Gly Pro Glu Pro Val Leu Leu Phe Ala Asn Arg Ile
        435                 440                 445
Asp Ile Arg Gln Val Leu Pro His Arg Ser Glu Tyr Thr Leu Leu Leu
        450                 455                 460
Asn Asn Leu Glu Asn Ala Ile Ala Leu Asp Phe His His Arg Arg Glu
465                 470                 475                 480
Leu Val Phe Trp Ser Asp Val Thr Leu Asp Arg Ile Leu Arg Ala Asn
                485                 490                 495
Leu Asn Gly Ser Asn Val Glu Glu Val Val Ser Thr Gly Leu Glu Ser
                500                 505                 510
Pro Gly Gly Leu Ala Val Asp Trp Val His Asp Lys Leu Tyr Trp Thr
        515                 520                 525
Asp Ser Gly Thr Ser Arg Ile Glu Val Ala Asn Leu Asp Gly Ala His
        530                 535                 540
Arg Lys Val Leu Leu Trp Gln Asn Leu Glu Lys Pro Arg Ala Ile Ala
545                 550                 555                 560
Leu His Pro Met Glu Gly Thr Ile Tyr Trp Thr Asp Trp Gly Asn Thr
                565                 570                 575
Pro Arg Ile Glu Ala Ser Ser Met Asp Gly Ser Gly Arg Arg Ile Ile
        580                 585                 590
Ala Asp Thr His Leu Phe Trp Pro Asn Gly Leu Thr Ile Asp Tyr Ala
        595                 600                 605
Gly Arg Arg Met Tyr Trp Val Asp Ala Lys His His Val Ile Glu Arg
        610                 615                 620
Ala Asn Leu Asp Gly Ser His Arg Lys Ala Val Ile Ser Gln Gly Leu
625                 630                 635                 640
Pro His Pro Phe Ala Ile Thr Val Phe Glu Asp Ser Leu Tyr Trp Thr
                645                 650                 655
Asp Trp His Thr Lys Ser Ile Asn Ser Ala Asn Lys Phe Thr Gly Lys
                660                 665                 670
Asn Gln Glu Ile Ile Arg Asn Lys Leu His Phe Pro Met Asp Ile His
        675                 680                 685
```

```
Thr Leu His Pro Gln Arg Gln Pro Ala Gly Lys Asn Arg Cys Gly Asp
    690             695                 700

Asn Asn Gly Gly Cys Thr His Leu Cys Leu Pro Ser Gly Gln Asn Tyr
705             710                 715                 720

Thr Cys Ala Cys Pro Thr Gly Phe Arg Lys Ile Ser His Ala Cys
                725                 730                 735

Ala Gln Ser Leu Asp Lys Phe Leu Leu Phe Ala Arg Arg Met Asp Ile
            740                 745                 750

Arg Arg Ile Ser Phe Asp Thr Glu Asp Leu Ser Asp Val Ile Pro
        755                 760                 765

Leu Ala Asp Val Arg Ser Ala Val Ala Leu Asp Trp Asp Ser Arg Asp
    770                 775                 780

Asp His Val Tyr Trp Thr Asp Val Ser Thr Thr Ile Ser Arg Ala
785             790                 795                 800

Lys Trp Asp Gly Thr Gly Gln Glu Val Val Val Asp Thr Ser Leu Glu
                805                 810                 815

Ser Pro Ala Gly Leu Ala Ile Asp Trp Val Thr Asn Lys Leu Tyr Trp
            820                 825                 830

Thr Asp Ala Gly Thr Asp Arg Ile Glu Val Ala Asn Thr Asp Gly Ser
        835                 840                 845

Met Arg Thr Val Leu Ile Trp Glu Asn Leu Asp Arg Pro Arg Asp Ile
    850                 855                 860

Val Val Glu Pro Met Gly Gly Tyr Met Tyr Trp Thr Asp Trp Gly Ala
865                 870                 875                 880

Ser Pro Lys Ile Glu Arg Ala Gly Met Asp Ala Ser Gly Arg Gln Val
                885                 890                 895

Ile Ile Ser Ser Asn Leu Thr Trp Pro Asn Gly Leu Ala Ile Asp Tyr
            900                 905                 910

Gly Ser Gln Arg Leu Tyr Trp Ala Asp Ala Gly Met Lys Thr Ile Glu
        915                 920                 925

Phe Ala Gly Leu Asp Gly Ser Lys Arg Lys Val Leu Ile Gly Ser Gln
    930                 935                 940

Leu Pro His Pro Phe Gly Leu Thr Leu Tyr Gly Glu Arg Ile Tyr Trp
945                 950                 955                 960

Thr Asp Trp Gln Thr Lys Ser Ile Gln Ser Ala Asp Arg Leu Thr Gly
                965                 970                 975

Leu Asp Arg Glu Thr Leu Gln Glu Asn Leu Glu Asn Leu Met Asp Ile
            980                 985                 990

His Val Phe His Arg Arg Pro  Pro Val Ser Thr Pro  Cys Ala Met
            995                 1000                1005

Glu Asn  Gly Gly Cys Ser  His  Leu Cys Leu Arg Ser  Pro Asn Pro
    1010                  1015                 1020

Ser Gly  Phe Ser Cys Thr  Cys  Pro Thr Gly Ile Asn  Leu Leu Ser
    1025                  1030                 1035

Asp Gly  Lys Thr Cys Ser  Pro  Gly Met Asn Ser Phe  Leu Ile Phe
    1040                  1045                 1050

Ala Arg  Arg Ile Asp Ile  Arg  Met Val Ser Leu Asp  Ile Pro Tyr
    1055                  1060                 1065

Phe Ala  Asp Val Val Pro  Ile  Asn Ile Thr Met  Lys Asn Thr
    1070                  1075                 1080

Ile Ala  Ile Gly Val Asp  Pro  Gln Glu Gly Lys Val  Tyr Trp Ser
    1085                  1090                 1095
```

-continued

Asp Ser Thr Leu His Arg Ile Ser Arg Ala Asn Leu Asp Gly Ser
1100                1105                1110

Gln His Glu Asp Ile Ile Thr Thr Gly Leu Gln Thr Thr Asp Gly
1115                1120                1125

Leu Ala Val Asp Ala Ile Gly Arg Lys Val Tyr Trp Thr Asp Thr
1130                1135                1140

Gly Thr Asn Arg Ile Glu Val Gly Asn Leu Asp Gly Ser Met Arg
1145                1150                1155

Lys Val Leu Val Trp Gln Asn Leu Asp Ser Pro Arg Ala Ile Val
1160                1165                1170

Leu Tyr His Glu Met Gly Phe Met Tyr Trp Thr Asp Trp Gly Glu
1175                1180                1185

Asn Ala Lys Leu Glu Arg Ser Gly Met Asp Gly Ser Asp Arg Ala
1190                1195                1200

Val Leu Ile Asn Asn Asn Leu Gly Trp Pro Asn Gly Leu Thr Val
1205                1210                1215

Asp Lys Ala Ser Ser Gln Leu Leu Trp Ala Asp Ala His Thr Glu
1220                1225                1230

Arg Ile Glu Ala Ala Asp Leu Asn Gly Ala Asn Arg His Thr Leu
1235                1240                1245

Val Ser Pro Val Gln His Pro Tyr Gly Leu Thr Leu Leu Asp Ser
1250                1255                1260

Tyr Ile Tyr Trp Thr Asp Trp Gln Thr Arg Ser Ile His Arg Ala
1265                1270                1275

Asp Lys Gly Thr Gly Ser Asn Val Ile Leu Val Arg Ser Asn Leu
1280                1285                1290

Pro Gly Leu Met Asp Met Gln Ala Val Asp Arg Ala Gln Pro Leu
1295                1300                1305

Gly Phe Asn Lys Cys Gly Ser Arg Asn Gly Gly Cys Ser His Leu
1310                1315                1320

Cys Leu Pro Arg Pro Ser Gly Phe Ser Cys Ala Cys Pro Thr Gly
1325                1330                1335

Ile Gln Leu Lys Gly Asp Gly Lys Thr Cys Asp Pro Ser Pro Glu
1340                1345                1350

Thr Tyr Leu Leu Phe Ser Ser Arg Gly Ser Ile Arg Arg Ile Ser
1355                1360                1365

Leu Asp Thr Ser Asp His Thr Asp Val His Val Pro Val Pro Glu
1370                1375                1380

Leu Asn Asn Val Ile Ser Leu Asp Tyr Asp Ser Val Asp Gly Lys
1385                1390                1395

Val Tyr Tyr Thr Asp Val Phe Leu Asp Val Ile Arg Arg Ala Asp
1400                1405                1410

Leu Asn Gly Ser Asn Met Glu Thr Val Ile Gly Arg Gly Leu Lys
1415                1420                1425

Thr Thr Asp Gly Leu Ala Val Asp Trp Val Ala Arg Asn Leu Tyr
1430                1435                1440

Trp Thr Asp Thr Gly Arg Asn Thr Ile Glu Ala Ser Arg Leu Asp
1445                1450                1455

Gly Ser Cys Arg Lys Val Leu Ile Asn Asn Ser Leu Asp Glu Pro
1460                1465                1470

Arg Ala Ile Ala Val Phe Pro Arg Lys Gly Tyr Leu Phe Trp Thr
1475                1480                1485

-continued

```
Asp Trp Gly His Ile Ala Lys Ile Glu Arg Ala Asn Leu Asp Gly
    1490            1495                1500

Ser Glu Arg Lys Val Leu Ile Asn Thr Asp Leu Gly Trp Pro Asn
    1505                1510                1515

Gly Leu Thr Leu Asp Tyr Asp Thr Arg Arg Ile Tyr Trp Val Asp
    1520                1525                1530

Ala His Leu Asp Arg Ile Glu Ser Ala Asp Leu Asn Gly Lys Leu
    1535                1540                1545

Arg Gln Val Leu Val Ser His Val Ser His Pro Phe Ala Leu Thr
    1550                1555                1560

Gln Gln Asp Arg Trp Ile Tyr Trp Thr Asp Trp Gln Thr Lys Ser
    1565                1570                1575

Ile Gln Arg Val Asp Lys Tyr Ser Gly Arg Asn Lys Glu Thr Val
    1580                1585                1590

Leu Ala Asn Val Glu Gly Leu Met Asp Ile Ile Val Val Ser Pro
    1595                1600                1605

Gln Arg Gln Thr Gly Thr Asn Ala Cys Gly Val Asn Asn Gly Gly
    1610                1615                1620

Cys Thr His Leu Cys Phe Ala Arg Ala Ser Asp Phe Val Cys Ala
    1625                1630                1635

Cys Pro Asp Glu Pro Asp Ser Arg Pro Cys Ser Leu Val Pro Gly
    1640                1645                1650

Leu Val Pro Pro Ala Pro Arg Ala Thr Gly Met Ser Glu Lys Ser
    1655                1660                1665

Pro Val Leu Pro Asn Thr Pro Pro Thr Thr Leu Tyr Ser Ser Thr
    1670                1675                1680

Thr Arg Thr Arg Thr Ser Leu Glu Glu Val Glu Gly Arg Cys Ser
    1685                1690                1695

Glu Arg Asp Ala Arg Leu Gly Leu Cys Ala Arg Ser Asn Asp Ala
    1700                1705                1710

Val Pro Ala Ala Pro Gly Glu Gly Leu His Ile Ser Tyr Ala Ile
    1715                1720                1725

Gly Gly Leu Leu Ser Ile Leu Leu Ile Leu Val Val Ile Ala Ala
    1730                1735                1740

Leu Met Leu Tyr Arg His Lys Lys Ser Lys Phe Thr Asp Pro Gly
    1745                1750                1755

Met Gly Asn Leu Thr Tyr Ser Asn Pro Ser Tyr Arg Thr Ser Thr
    1760                1765                1770

Gln Glu Val Lys Ile Glu Ala Ile Pro Lys Pro Ala Met Tyr Asn
    1775                1780                1785

Gln Leu Cys Tyr Lys Lys Glu Gly Gly Pro Asp His Asn Tyr Thr
    1790                1795                1800

Lys Glu Lys Ile Lys Ile Val Glu Gly Ile Cys Leu Leu Ser Gly
    1805                1810                1815

Asp Asp Ala Glu Trp Asp Asp Leu Lys Gln Leu Arg Ser Ser Arg
    1820                1825                1830

Gly Gly Leu Leu Arg Asp His Val Cys Met Lys Thr Asp Thr Val
    1835                1840                1845

Ser Ile Gln Ala Ser Ser Gly Ser Leu Asp Asp Thr Glu Thr Glu
    1850                1855                1860

Gln Leu Leu Gln Glu Glu Gln Ser Glu Cys Ser Ser Val His Thr
    1865                1870                1875
```

-continued

```
Ala Ala  Thr Pro Glu Arg Arg  Gly Ser Leu Pro Asp  Thr Gly Trp
    1880             1885              1890

Lys His  Glu Arg Lys Leu Ser  Ser Glu Ser Gln Val
    1895             1900              1905
```